United States Patent
Hartman

(10) Patent No.: US 12,129,251 B2
(45) Date of Patent: Oct. 29, 2024

(54) N-OXIDE INHIBITORS OF NLRP3 INFLAMMASOME

(71) Applicant: BioAge Labs, Inc., Richmond, CA (US)

(72) Inventor: George Hartman, Lansdale, PA (US)

(73) Assignee: BioAge Labs, Inc., Richmond, CA (US)

( * ) Notice: Subject to any disclaimer, the term of this patent is extended or adjusted under 35 U.S.C. 154(b) by 0 days.

(21) Appl. No.: 18/462,015

(22) Filed: Sep. 6, 2023

(65) Prior Publication Data

US 2024/0067648 A1  Feb. 29, 2024

Related U.S. Application Data

(62) Division of application No. 18/160,594, filed on Jan. 27, 2023, now Pat. No. 11,787,805.

(60) Provisional application No. 63/383,573, filed on Nov. 14, 2022, provisional application No. 63/377,248, filed on Sep. 27, 2022, provisional application No. 63/304,164, filed on Jan. 28, 2022.

(51) Int. Cl.
C07D 471/04 (2006.01)

(52) U.S. Cl.
CPC .................. C07D 471/04 (2013.01)

(58) Field of Classification Search
CPC .................................. C07D 471/04
USPC ........................................ 514/303
See application file for complete search history.

(56) References Cited

U.S. PATENT DOCUMENTS

| 7,511,062 B2 * | 3/2009 | Kuang | A61P 25/28 546/159 |
|---|---|---|---|
| 2022/0324812 A1 | 10/2022 | Hartman et al. | |

FOREIGN PATENT DOCUMENTS

| CN | 111 329 993 A | 6/2020 |
|---|---|---|
| EP | 2 269 990 A1 | 1/2011 |
| EP | 3 660 003 A1 | 6/2020 |
| WO | WO 2004/099143 A1 | 11/2004 |
| WO | WO 2008/006561 A1 | 1/2008 |
| WO | WO 2012/101453 A1 | 8/2012 |
| WO | WO 2013/126856 A1 | 8/2013 |
| WO | WO 2016/081290 A1 | 5/2016 |
| WO | WO 2019/001416 A1 | 1/2019 |
| WO | WO 2019/193342 A1 | 10/2019 |
| WO | WO 2020/097389 A1 | 5/2020 |

OTHER PUBLICATIONS

U.S. Appl. No. 17/701,856 / 2022-0324812 A1 / U.S. Pat. No. 11,702,391, filed Mar. 23, 2022 / Oct. 13, 2022 / Jul. 18, 2023, George Hartman.
U.S. Appl. No. 17/930,895 / 2023-0051130 A1 / U.S. Pat. No. 11,708,334, filed Sep. 9, 2022 / Feb. 16, 2023 / Jul. 25, 2023, George Hartman.
U.S. Appl. No. 18/323,939, filed May 25, 2023, George Hartman.
U.S. Appl. No. 18/353,410, filed Jul. 17, 2023, George Hartman.
U.S. Appl. No. 18/353,422, filed Jul. 17, 2023, George Hartman.
U.S. Appl. No. 18/353,370, filed Jul. 17, 2023, George Hartman.
U.S. Appl. No. 18/160,594 / 2023-0242528 A1, filed Jan. 27, 2023 / Aug. 3, 2023, George Hartman.
U.S. Appl. No. 18/462,015, filed Sep. 6, 2023, George Hartman.
Fischer et al., "Age-Dependent Changes in the Cochlea", *Gerontology* 1-7 (2019).
Franceshi et al., "Inflamm-aging: An Evolutionary Perspective on Immunosenescence", *Annals of the New York Academy of Sciences* 908(1):244-254 (2000).
Hubbard et al., "Frailty, inflammation and the elderly" *Biogerontology* 11(5):635-641 (2010).
International Search Report and Written Opinion for International Application No. PCT/US2022/021461, mailed Jun. 14, 2022, 15 pages.
Kang et al., "Synthesis and structure-activity relationships of novel fused ring analogues of Q203 as antitubercular agents", *European Journal of Medicinal Chemistry* 136(1):420-427 (2017), doi:10.1016/j.ejmech.2017.05.021.
Le Prell et al., "Noise-induced hearing loss and its prevention: current issues in mammalian hearing" *Current Opinion in Physiology* 18:32-36 (2020).
Montalvao et al., "Synthesis and Biological Evaluation of 2-Aminobenzothiazole and Benzimidazole Analogs Based on the Clathrodin Structure", *Arch. Pharm. Chem. Life Sci.* 349(2):137-149 (2016); doi:10.1002/ardp.201500365.
Nakanishi et al., "NLRP3 mutation and cochlear autoinflammation cause syndromic and nonsyndromic hearing loss DFNA34 responsive to anakinra therapy", *PNAS* 114(37):E7766-E7775 (2017).
Nakanishi et al., "Genetic Hearing Loss Associated With Autoinflammation", *Frontiers in Neurology* 11(Art. 141):1-7 (2020).
Schwaid et al., "Strategies for Targeting the NLRP3 Inflammasome in the Clinical and Preclinical Space", *Journal of Medicinal Chemistry* 64(1):101-122 (2021).
Yao et al., "Inflammation and Immune Systems Alterations in Frailty", *Clinics in Geriatric Medicine* 27(1):79-87 (2011).
Yee et al., "Zika virus infection causes widespread damage to the inner ear", *Hearing Research* 395:1-15 (2020).
Zahid et al., "Pharmacological Inhibitors of the MLRP3 Inflammasome", Frontiers in Immunology vol. 10, Article 2538 (2019); doi: 10.3389/fimmu.2019.02538.

* cited by examiner

*Primary Examiner* — Niloofar Rahmani
(74) *Attorney, Agent, or Firm* — LATHROP GPM LLP; Brian C. Trinque; Nicole Sassu

(57) ABSTRACT

The present disclosure relates to compounds that act as inhibitors of NLRP3 inflammasomes; pharmaceutical compositions comprising the compounds; and methods of treating disorders associated with inflammation and inflammaging, including hearing loss and other diseases associated with aging.

25 Claims, No Drawings

N-OXIDE INHIBITORS OF NLRP3 INFLAMMASOME

RELATED APPLICATIONS

This application claims priority to U.S. Provisional Application No. 63/304,164 filed on Jan. 28, 2022, U.S. Provisional Application No. 63/377,248 filed on Sep. 27, 2022, and U.S. Provisional Application No. 63/383,573 filed on Nov. 14, 2022, the contents of which are hereby incorporated by reference in their entirety.

BACKGROUND

Aging frailty poses a very concerning problem for the overall health and well-being of individuals and is characterized as a syndrome of multisystem physiological dysregulation. Aging frailty is a geriatric syndrome characterized by weakness, low physical activity, slowed motor performance, exhaustion, and unintentional weight loss (Yao, X. et al., Clinics in Geriatric Medicine 27(1):79-87 (2011)). Furthermore, there are many studies showing a direct correlation between aging frailty and inflammation (Hubbard, R. E., et al., Biogerontology 11(5):635-641 (2010)). Immunosenescence is characterized by a low grade, chronic systemic inflammatory state known as inflammaging (Franceshi, C. et al., Annals of the New York Academy of Sciences 908:244-254 (2000)). This heightened inflammatory state or chronic inflammation found in aging and aging frailty leads to immune dysregulation and a complex remodeling of both innate and adaptive immunity.

Inhibiting the NLRP3 inflammasome, an oligomeric protein complex that includes ASC and caspase-1, mediates inflammation in an extensive number of preclinical models (Schwaid, A. G., J. Med. Chem. 2021, 64(1), 101-122). At the same time, the NLRP3 inflammasome is part of a larger pro-inflammatory pathway, whose modulation is also being explored. NLRP3 is an inflammasome sensor protein that has been well studied in a number of disease contexts. Many different indications are associated with the NLRP3 inflammasome including diseases related to aging, cryopyrin-associated periodic syndrome (CAPS), nonalcoholic steatohepatitis (NASH), gout, coronary artery disease, Crohn's disease, osteoarthritis, rheumatoid arthritis, Alzheimer's disease, Parkinson's disease, intestinal disorders, acute respiratory distress syndrome (ARDS), amyotrophic lateral sclerosis (ALS), cancer, and dermatological diseases.

Inflammation, as well as activation of the NLRP3 inflammasome, have also been shown to result in hearing loss (Nakanishi, H., et al., Frontiers in Neurology, 2020, 11, 1-7; Nakanishi, H., et al., PNAS, 2017, E7766-E7775). The inflammation-related hearing loss can be age-dependent (Fischer, N., et al., Gerontology, 2019, 1-7), noise-induced (Le Prell, C. G., et al. Current Opinion in Physiology, 2020, 18, 32-36), and the result of a viral infection such as Zika virus and coronavirus (Yee, K. T., et al., Hearing Research, 2020, 395, 1-15).

The NLRP3 inflammasome is therefore a promising drug target. The breadth of the indications it is implicated in speak to the need for therapeutics that target the NLRP3 inflammasome.

SUMMARY

Provided here are compounds that inhibit the NLRP3 inflammasome. As such, these compounds are useful in the treatment of a variety of indications, including inflammaging and inflammation.

In an aspect, provided herein is a compound of Formula I:

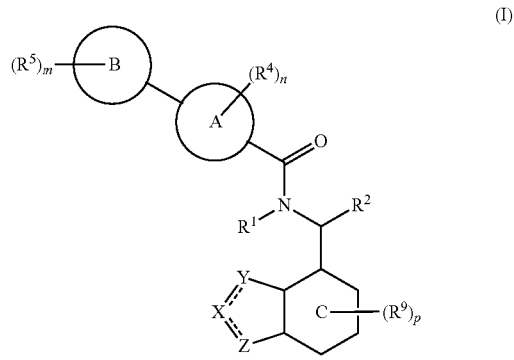

or a pharmaceutically acceptable salt thereof, wherein Ring C is pyridine N-oxide.

In yet another aspect, provided herein is a pharmaceutical composition comprising a compound described herein, or a pharmaceutically acceptable salt thereof, and a pharmaceutically acceptable carrier.

In yet another aspect, provided herein is a method of inhibiting NLRP3 inflammasome in a subject in need thereof comprising administering to the subject a therapeutically effective amount of a compound described herein.

DETAILED DESCRIPTION

Provided here are compounds that inhibit the NLRP3 inflammasome. As such, these compounds, as well as pharmaceutical compositions that comprise these compounds, are useful in the treatment of a variety of indications, including inflammaging, inflammation, and other age-related diseases.

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In certain embodiments, the treatment comprises alleviating the symptoms of inflammaging and age-related disorders.

As used herein, the term "contacting" refers to the bringing together of indicated moieties in an in vitro system or an in vivo system. For example, "contacting" a cell with a compound includes the administration of a compound of the present invention to an individual, subject, or patient, such as a human, as well as, for example, introducing a compound into a sample containing a purified preparation containing the cell.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "cell" is meant to refer to a cell that is in vitro, ex vivo, or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

As used herein, "inflammaging" is defined as chronic sterile inflammation that is associated with numerous age-related diseases.

As used herein, "age-related disorder" refers to disorders that are associated with the aging processStated alternatively, age-related disorders are diseases associated with the elderly. Non-limiting examples of age-related diseases include atherosclerosis and cardiovascular disease, cancer, arthritis, cataracts, osteoporosis, type 2 diabetes, hypertension, and Alzheimer's disease. The incidence of all of these diseases increases exponentially with age.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$ alkyl include ethyl, methyl, isopropyl, isobutyl, n-pentyl, and n-hexyl.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In an embodiment, "cycloalkyl" is $C_{3-10}$ cycloalkyl. In another embodiment, "cycloalkyl" is $C_{3-6}$ cycloalkyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydro-furanyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]-hexanyl, 6-azabicyclo[3.1.1] heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In an embodiment, "heterocycloalkyl" refers to 3-10 membered heterocycloalkyl. In another embodiment, "heterocycloalkyl" refers to 4-10 membered heterocycloalkyl. In yet another embodiment, "heterocycloalkyl" refers to 3-, 4-, 5-, or 6-membered heterocycloalkyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta-[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

Compounds

Provided herein are compounds that are inhibitors of the NLRP3 inflammasome and are thus useful in the treatment of inflammatory disorders, including cancer and other proliferation diseases.

In an aspect, provided herein is a compound of Formula I:

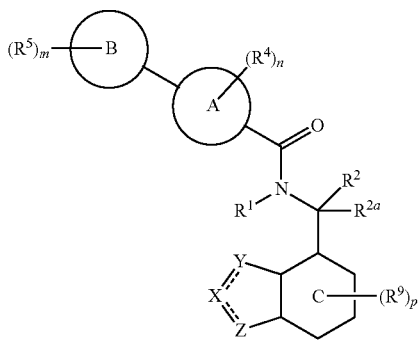

(I)

or a pharmaceutically acceptable salt thereof;
wherein
 ═ is an optional double bond;
 X, Y, and Z are each independently selected from the group consisting of NH, NR$^3$, N, CH, and CR$^3$, provided at least one of X, Y, or Z are CH or CR$^3$;
 Ring A is selected from the group consisting of C$_{6-10}$ aryl, 5-6 membered heteroaryl, C$_{3-10}$ cycloalkyl, and 4-10 membered heterocycloalkyl;
 Ring B is selected from the group consisting of phenyl, 5-6 membered heteroaryl, C$_{3-6}$ cycloalkyl, and 3-6 membered heterocycloalkyl;
 Ring C is pyridine N-oxide;
 R$^1$ is selected from the group consisting of H, C$_{3-6}$ cycloalkyl, and C$_{1-6}$ alkyl;
 R$^2$ and R$^{2a}$ are each independently selected from the group consisting of H, C$_{1-6}$ alkyl, C$_{1-6}$ alkoxy, and C$_{3-6}$ cycloalkyl;
 each R$^3$ is independently C$_{1-6}$ alkyl and C$_{3-6}$ cycloalkyl;
 each R$^4$ is independently selected from the group consisting of C$_{1-6}$ alkyl, halo, OH, OR$^6$, NH$_2$, NH(C$_{1-6}$ alkyl), N(C$_{1-6}$ alkyl)$_2$, NHCOR$^6$, CN, C$_{1-6}$ haloalkyl, C$_{3-7}$ cycloalkyl, 3-7 membered heterocycloalkyl, and COR$^6$;
 each R$^5$ is independently selected from the group consisting of C$_{1-6}$ alkyl, C$_{1-6}$ haloalkyl, halo, OH, OR$^7$, NH$_2$, NH(C$_{1-6}$ alkyl), N(C$_{1-6}$ alkyl)$_2$, NHCOR$^7$, CN, C$_{3-7}$ cycloalkyl, 3-7 membered heterocycloalkyl, COR$^7$, and SO$_2$R$^7$;
 each R$^6$ is independently selected from the group consisting of C$_{1-6}$ alkyl, C$_{1-6}$ haloalkyl, C$_{0-6}$ alkyl-C$_{6-10}$ aryl, C$_{0-6}$ alkyl-5-10 membered heteroaryl, C$_{1-6}$ alkoxy, C$_{3-6}$ cycloalkyl, 3-10 membered heterocycloalkyl, halo, NH$_2$, NH(C$_{1-6}$ alkyl), and N(C$_{1-6}$ alkyl)$_2$;
 each R$^7$ is independently selected from the group consisting of C$_{1-6}$ alkyl, C$_{1-6}$ haloalkyl, C$_{0-6}$ alkyl-C$_{6-10}$ aryl, C$_{0-6}$ alkyl-5-10 membered heteroaryl, C$_{1-6}$ alkoxy, C$_{3-6}$ cycloalkyl, halo, NH$_2$, NH(C$_{1-6}$ alkyl), and N(C$_{1-6}$ alkyl)$_2$;
 each R$^9$ is independently selected from the group consisting of C$_{1-6}$ alkyl, C$_{1-6}$ haloalkyl, C$_{1-6}$ alkoxy, C$_{1-6}$ alkyl-OH, C$_{3-6}$ cycloalkyl, halo, CN, OH, NH$_2$, NH(C$_{1-6}$ alkyl), and N(C$_{1-6}$ alkyl)$_2$;
 m is 0, 1, 2, or 3;
 n is 1, 2, or 3; and
 p is 0, 1, 2, or 3.
In an aspect of Formula I,
 ═ is an optional double bond;
 X, Y, and Z are each independently selected from the group consisting of NH, NR$^3$, N, CH, and CR$^3$, provided at least one of X, Y, or Z are CH or CR$^3$;
 Ring A is selected from the group consisting of C$_{6-10}$ aryl, 5-6 membered heteroaryl, C$_{3-10}$ cycloalkyl, and 4-10 membered heterocycloalkyl;
 Ring B is selected from the group consisting of phenyl, 5-6 membered heteroaryl, C$_{3-6}$ cycloalkyl, and 3-6 membered heterocycloalkyl;
 alternatively, Ring B is absent and m is 0;
 Ring C is pyridine N-oxide;
 R$^1$ is selected from the group consisting of H, C$_{3-6}$ cycloalkyl, and C$_{1-6}$ alkyl;
 R$^2$ and R$^{2a}$ are each independently selected from the group consisting of H, C$_{1-6}$ alkyl, C$_{1-6}$ alkoxy, and C$_{3-6}$ cycloalkyl;
 alternatively, R$^2$ and R$^{2a}$, together with the atom to which they are attached form C$_{3-6}$ cycloalkyl or 3-6 membered heterocycloalkyl;
 each R$^3$ is independently C$_{1-6}$ alkyl and C$_{3-6}$ cycloalkyl;
 each R$^4$ is independently selected from the group consisting of C$_{1-6}$ alkyl, C$_{2-6}$ alkynyl, halo, OH, OR$^6$, NH$_2$, NH(C$_{1-6}$ alkyl), N(C$_{1-6}$ alkyl)$_2$, NHCOR$^6$, CN, C$_{1-6}$ haloalkyl, C$_{3-7}$ cycloalkyl, 3-7 membered heterocycloalkyl, and COR$^6$;
 each R$^5$ is independently selected from the group consisting of C$_{1-6}$ alkyl, C$_{1-6}$ haloalkyl, C$_{1-6}$ alkyl-OH, C$_{2-6}$ alkynyl, halo, OH, OR$^7$, NH$_2$, NH(C$_{1-6}$ alkyl), N(C$_{1-6}$ alkyl)$_2$, NHCOR$^7$, CN, C$_{3-7}$ cycloalkyl, 3-7 membered heterocycloalkyl, COR$^7$, and SO$_2$R$^7$; each R$^6$ is independently selected from the group consisting of C$_{1-6}$ alkyl, C$_{1-6}$ haloalkyl, C$_{0-6}$ alkyl-C$_{6-10}$ aryl, C$_{0-6}$ alkyl-5-10 membered heteroaryl, C$_{1-6}$ alkoxy, C$_{0-6}$ alkyl-C$_{3-6}$ cycloalkyl, C$_{0-6}$ alkyl-3-10 membered heterocycloalkyl, halo, NH$_2$, NH(C$_{1-6}$ alkyl), and N(C$_{1-6}$ alkyl)$_2$;
 each R$^7$ is independently selected from the group consisting of C$_{1-6}$ alkyl, C$_{1-6}$ haloalkyl, C$_{0-6}$ alkyl-C$_{6-10}$ aryl, C$_{0-6}$ alkyl-5-10 membered heteroaryl, C$_{1-6}$ alkoxy, C$_{3-6}$ cycloalkyl, halo, NH$_2$, NH(C$_{1-6}$ alkyl), and N(C$_{1-6}$ alkyl)$_2$;
 each R$^9$ is independently selected from the group consisting of C$_{1-6}$ alkyl, C$_{1-6}$ haloalkyl, C$_{1-6}$ alkoxy, C$_{1-6}$ alkyl-OH, C$_{3-6}$ cycloalkyl, halo, CN, OH, NH$_2$, NH(C$_{1-6}$ alkyl), and N(C$_{1-6}$ alkyl)$_2$;
 m is 0, 1, 2, or 3;
 n is 1, 2, or 3; and
 p is 0, 1, 2, or 3.
In an embodiment, the compound of Formula I is a compound of Formula Ia:

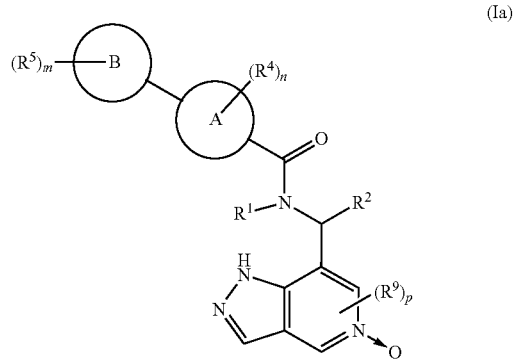

(Ia)

or a pharmaceutically acceptable salt thereof.

In another embodiment, the compound of Formula I is a compound of Formula Ib:

(Ib)

or a pharmaceutically acceptable salt thereof.

In yet another embodiment, the compound of Formula I is a compound of Formula Ic:

(Ic)

or a pharmaceutically acceptable salt thereof.

In yet another embodiment, Ring A is $C_{6-10}$ aryl. In still another embodiment, Ring A is phenyl.

In an embodiment, Ring B is phenyl or 5-6 membered heteroaryl. In another embodiment, Ring B is phenyl. In yet another embodiment, Ring B is thienyl.

In still another embodiment, $R^1$ is $C_{1-6}$ alkyl;
$R^2$ is selected from the group consisting of H, $C_{1-6}$ alkyl, $C_{1-6}$ alkoxy, and $C_{3-6}$ cycloalkyl;
$R^{2a}$ is H;
each $R^4$ is independently selected from the group consisting of $C_{1-6}$ alkyl, halo, and $OR^6$;
each $R^5$ is independently selected from the group consisting of $C_{1-6}$ haloalkyl, halo, CN, and $COR^7$;
each $R^6$ is independently selected from the group consisting of $C_{1-6}$ alkyl, $C_{1-6}$ haloalkyl, $C_{3-6}$ cycloalkyl, and 3-6 membered heterocycloalkyl;
each $R^7$ is independently selected from the group consisting of $C_{1-6}$ alkyl, $C_{1-6}$ haloalkyl, $C_{3-6}$ cycloalkyl, and $NH(C_{1-6}$ alkyl);
each $R^9$ is independently selected from the group consisting of $C_{1-6}$ alkyl, $C_{1-6}$ haloalkyl, $C_{1-6}$ alkoxy, $C_{1-6}$ alkyl-OH, $C_{3-6}$ cycloalkyl, and CN;
m is 0, 1, or 2; and
n is 1 or 2.

In an embodiment, $R^1$ is $C_{1-3}$ alkyl.

In another embodiment, $R^2$ is H. In another embodiment, $R^{2a}$ is H.

In yet another embodiment, each $R^4$ is independently selected from the group consisting of $C_{1-6}$ alkyl, halo, and $OR^6$. In still another embodiment, $R^4$ is independently selected from the group consisting of O(ethyl), O(cyclopropyl), O(oxetanyl), and $O(C_{1-3}$ haloalkyl).

In an embodiment, each $R^5$ is independently selected from the group consisting of $C_{1-6}$ haloalkyl, halo, CN, and $COR^7$. In another embodiment, each $R^5$ is independently selected from the group consisting of $C_{1-6}$ haloalkyl, halo, CN, and $CONH(C_{1-6}$ alkyl).

In an embodiment, each $R^6$ is independently selected from the group consisting of $C_{1-6}$ alkyl, $C_{1-6}$ haloalkyl, $C_{3-6}$ cycloalkyl, and 3-6 membered heterocycloalkyl.

In another embodiment, each $R^7$ is independently selected from the group consisting of $C_{1-6}$ alkyl, $C_{1-6}$ haloalkyl, $C_{3-6}$ cycloalkyl, and $NH(C_{1-6}$ alkyl).

In another embodiment, each $R^9$ is independently selected from the group consisting of $C_{1-6}$ alkyl, $C_{1-6}$ haloalkyl, $C_{1-6}$ alkoxy, $C_{1-6}$ alkyl-OH, $C_{3-6}$ cycloalkyl, and CN. In yet another embodiment, each $R^9$ is independently $C_{1-6}$ alkyl.

In still another embodiment, m is 1 or 2. In an embodiment, m is 1. In another embodiment, m is 2. In yet another embodiment, m is 0.

In an embodiment, n is 1 or 2. In another embodiment, n is 1. In yet another embodiment, n is 2. In still another embodiment, n is 0.

In another embodiment, p is 0 or 1. In yet another embodiment, p is 0. In still another embodiment, p is 1. In an embodiment, p is 2.

In another embodiment,
Ring A is phenyl;
Ring B is phenyl or thienyl;
$R^1$ is $C_{1-3}$ alkyl;
$R^2$ is selected from the group consisting of H, $C_{1-6}$ alkyl, $C_{1-6}$ alkoxy, and $C_{3-6}$ cycloalkyl;
each $R^4$ is independently selected from the group consisting of $C_{1-6}$ alkyl, halo, and $OR^6$;
each $R^5$ is independently selected from the group consisting of $C_{1-6}$ haloalkyl, halo, CN, and $COR^7$;
each $R^6$ is independently selected from the group consisting of $C_{1-3}$ alkyl, $C_{1-3}$ haloalkyl, $C_{3-6}$ cycloalkyl, and 3-6 membered heterocycloalkyl;
each $R^7$ is independently selected from the group consisting of $C_{1-6}$ alkyl, $C_{1-6}$ haloalkyl, $C_{3-6}$ cycloalkyl, and $NH(C_{1-6}$ alkyl);
each $R^9$ is independently selected from the group consisting of $C_{1-3}$ alkyl, $C_{1-3}$ haloalkyl, $C_{1-3}$ alkoxy, $C_{1-6}$ alkyl-OH, $C_{3-6}$ cycloalkyl, and CN;
m is 1 or 2;
n is 1 or 2; and
p is 0 or 1.

In yet another embodiment,
X is N;
Y and Z are each independently selected from the group consisting of NH and CH.

In still another embodiment, the compound of Formula I has one of the following core structures:

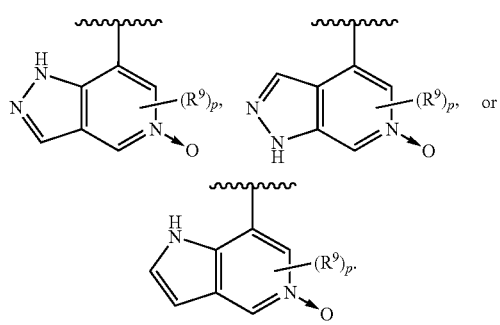
In an embodiment, the compound of Formula I has the following core structure:
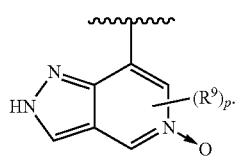
In another embodiment, the compound of Formula I is selected from the group consisting of a compound in Table 1.
TABLE 1
| Structure | No. |
|---|---|
| 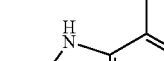 | 001 |
| 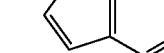 | 002 |
TABLE 1-continued
| Structure | No. |
|---|---|
| 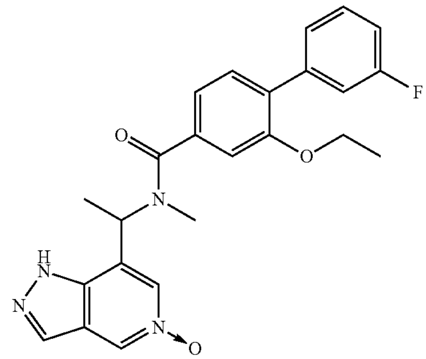 [SMILES: CCOc1cc(C(=O)N(C)C(C)c2c[n+]([O-])cc3cn[nH]c23)ccc1-c1cccc(F)c1] | 003 |
| 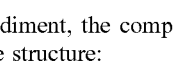 | 004 |
| 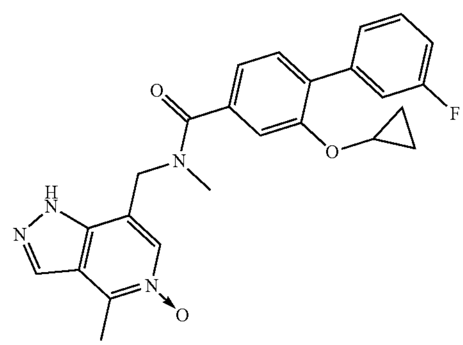 [SMILES: Cc1c2cn[nH]c2c(CN(C)C(=O)c2ccc(-c3cccc(F)c3)c(OC3CC3)c2)c[n+]1[O-]] | 005 |
| 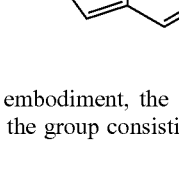 | 006 |

TABLE 1-continued

| Structure | No. |
|---|---|
| (structure) | 007 |
| (structure) | 008 |
| (structure) | 009 |
| (structure) | 010 |
| (structure) | 011 |
| (structure) | 012 |
| (structure) | 013 |
| (structure) | 014 |

TABLE 1-continued
| Structure | No. |
|---|---|
| 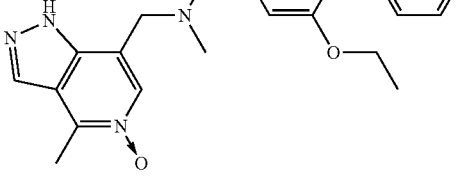 | 015 |
| 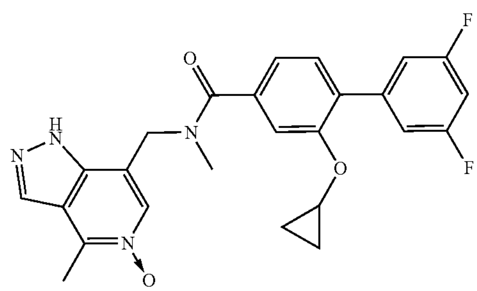 [SMILES: Cc1c2cn[nH]c2c(CN(C)C(=O)c2ccc(-c3cc(F)cc(F)c3)c(OC3CC3)c2)c[n+]1[O-]] | 016 |
| 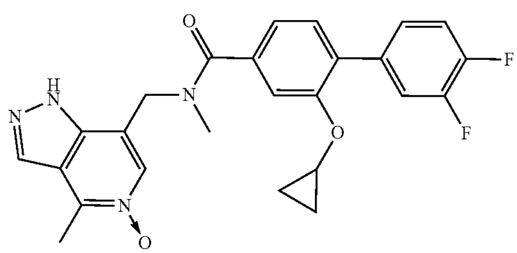 [SMILES: Cc1c2cn[nH]c2c(CN(C)C(=O)c2ccc(-c3ccc(F)c(F)c3)c(OC3CC3)c2)c[n+]1[O-]] | 017 |
| 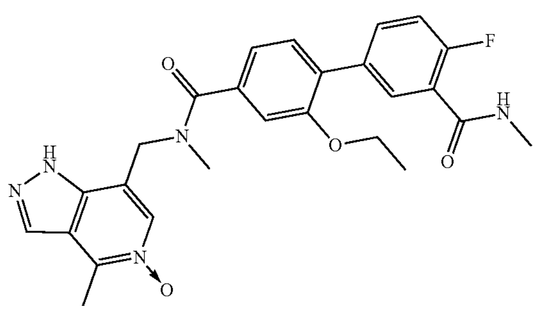 [SMILES: CCOc1cc(C(=O)N(C)Cc2c[n+]([O-])c(C)c3cn[nH]c23)ccc1-c1ccc(F)c(C(=O)NC)c1] | 018 |
| 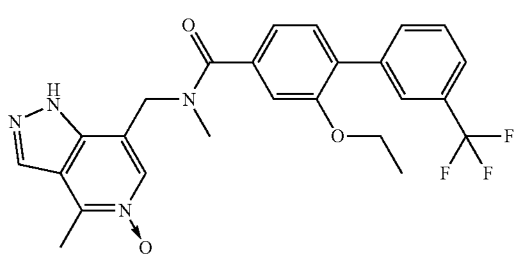 [SMILES: CCOc1cc(C(=O)N(C)Cc2c[n+]([O-])c(C)c3cn[nH]c23)ccc1-c1cccc(C(F)(F)F)c1] | 019 |
| | 020 |
| | 021 |
| | 022 |
| | 023 |
| | 024 |

TABLE 1-continued

| Structure | No. |
|---|---|
| (structure) | 025 |
| (structure) | 026 |
| (structure) | 027 |
| (structure) | 028 |
| (structure) | 029 |
| (structure) | 030 |
| (structure) | 031 |
| (structure) | 032 |
| (structure) | 033 | or a pharmaceutically acceptable salt thereof.

In yet another embodiment, the compound of Formula I is selected from the group consisting of a compound in Table 2.

TABLE 2

| Structure | No. |
|---|---|
| 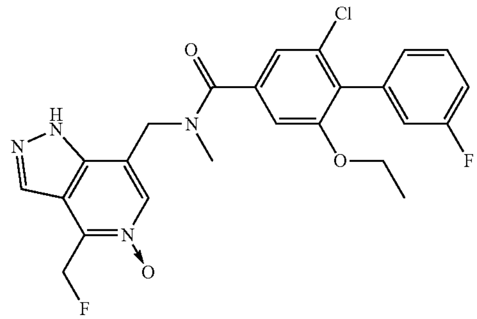 [SMILES: CCOc1cc(C(=O)N(C)Cc2c[n+]([O-])c(CF)c3cn[nH]c23)cc(Cl)c1-c1cccc(F)c1] | 034 |
| 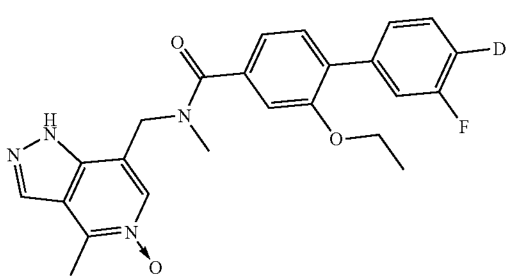 [SMILES: [2H]c1ccc(-c2ccc(C(=O)N(C)Cc3c[n+]([O-])c(C)c4cn[nH]c34)cc2OCC)cc1F] | 035 |
| 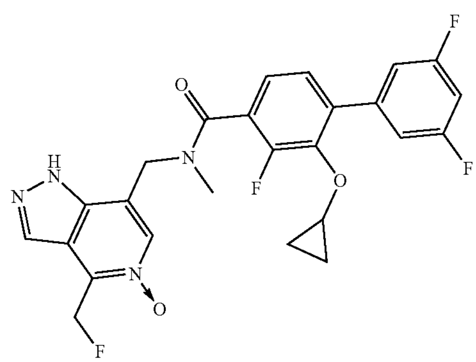 [SMILES: CN(Cc1c[n+]([O-])c(CF)c2cn[nH]c12)C(=O)c1ccc(-c2cc(F)cc(F)c2)c(OC2CC2)c1F] | 036 |
| 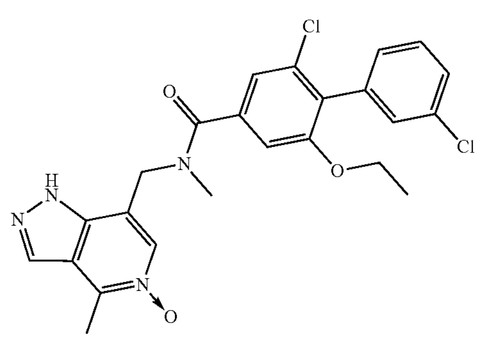 [SMILES: CCOc1cc(C(=O)N(C)Cc2c[n+]([O-])c(C)c3cn[nH]c23)cc(Cl)c1-c1cccc(Cl)c1] | 037 |
| 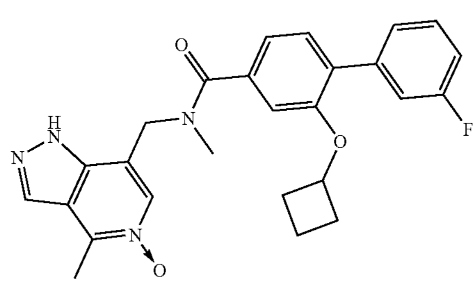 [SMILES: Cc1c2cn[nH]c2c(CN(C)C(=O)c2ccc(-c3cccc(F)c3)c(OC3CCC3)c2)c[n+]1[O-]] | 038 |

TABLE 2-continued

| Structure | No. |
|---|---|
| 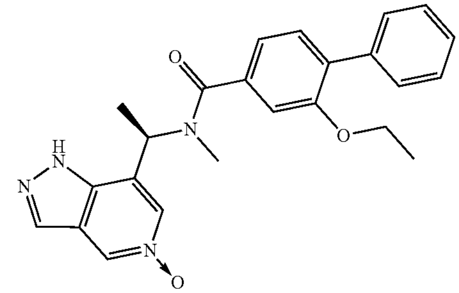 [SMILES: CCOc1cc(C(=O)N(C)[C@H](C)c2c[n+]([O-])cc3cn[nH]c23)ccc1-c1ccccc1] | 039 |
| 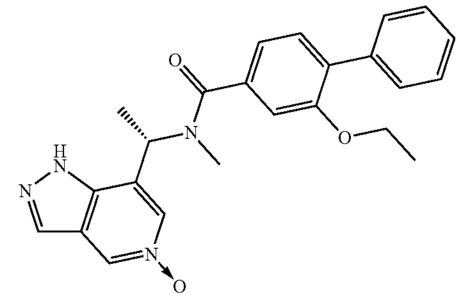 [SMILES: CCOc1cc(C(=O)N(C)[C@@H](C)c2c[n+]([O-])cc3cn[nH]c23)ccc1-c1ccccc1] | 040 |
| 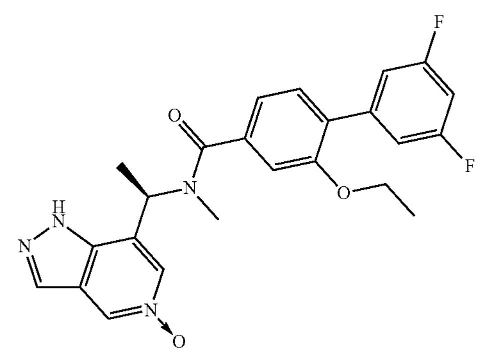 [SMILES: CCOc1cc(C(=O)N(C)[C@H](C)c2c[n+]([O-])cc3cn[nH]c23)ccc1-c1cc(F)cc(F)c1] | 041 |
| 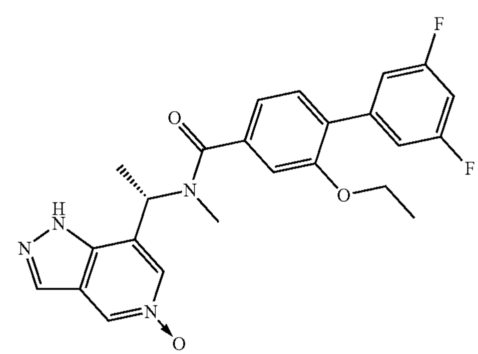 [SMILES: CCOc1cc(C(=O)N(C)[C@@H](C)c2c[n+]([O-])cc3cn[nH]c23)ccc1-c1cc(F)cc(F)c1] | 042 |
| 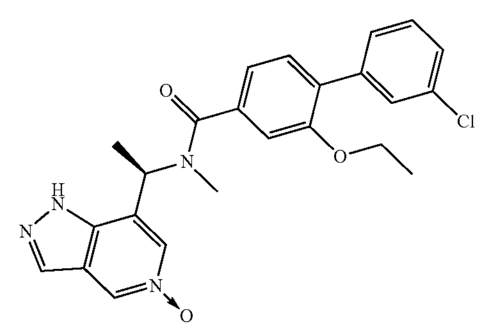 [SMILES: CCOc1cc(C(=O)N(C)[C@H](C)c2c[n+]([O-])cc3cn[nH]c23)ccc1-c1cccc(Cl)c1] | 043 |

TABLE 2-continued
| Structure | No. |
|---|---|
| 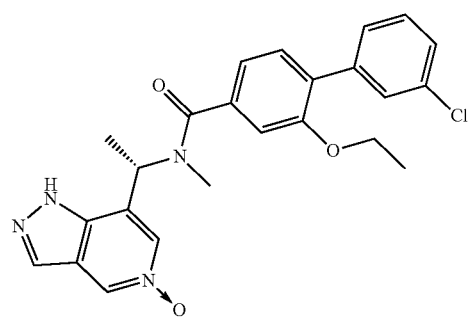 [SMILES: CCOc1cc(C(=O)N(C)[C@@H](C)c2c[n+]([O-])cc3cn[nH]c23)ccc1-c1cccc(Cl)c1] | 044 |
| 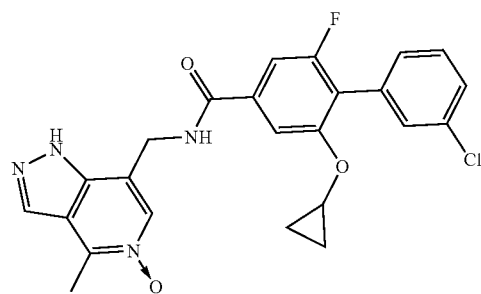 [SMILES: Cc1c2cn[nH]c2c(CNC(=O)c2cc(F)c(-c3cccc(Cl)c3)c(OC3CC3)c2)c[n+]1[O-]] | 045 |
| 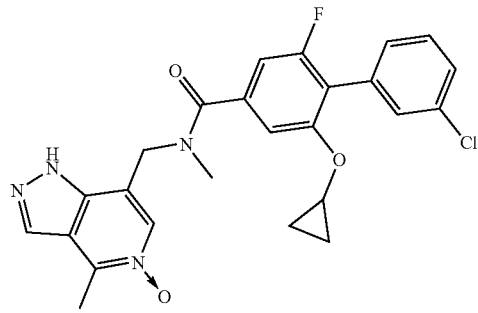 [SMILES: Cc1c2cn[nH]c2c(CN(C)C(=O)c2cc(F)c(-c3cccc(Cl)c3)c(OC3CC3)c2)c[n+]1[O-]] | 046 |
| 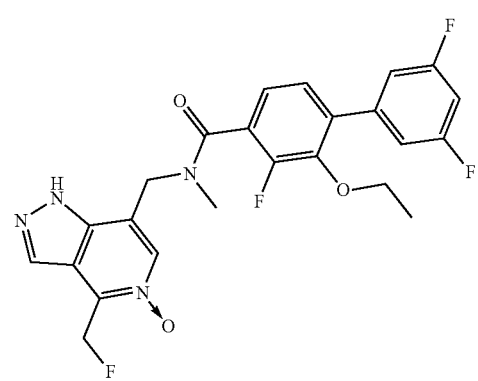 [SMILES: CCOc1c(-c2cc(F)cc(F)c2)ccc(C(=O)N(C)Cc2c[n+]([O-])c(CF)c3cn[nH]c23)c1F] | 047 |
TABLE 2-continued
| Structure | No. |
|---|---|
| 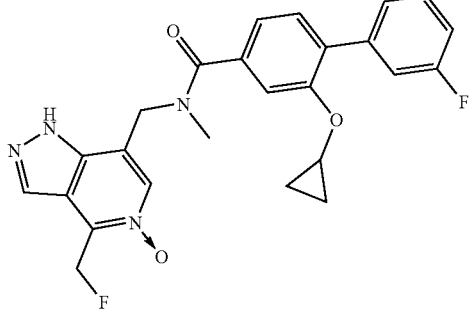 | 048 |
| 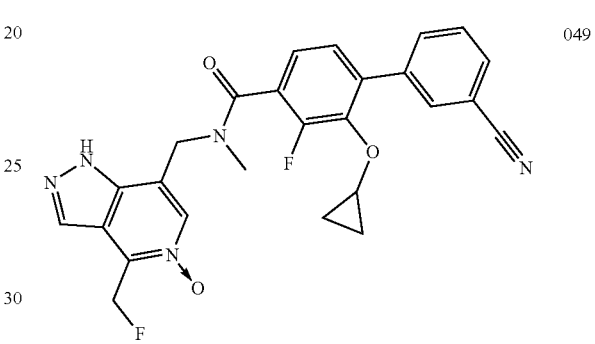 | 049 |
| 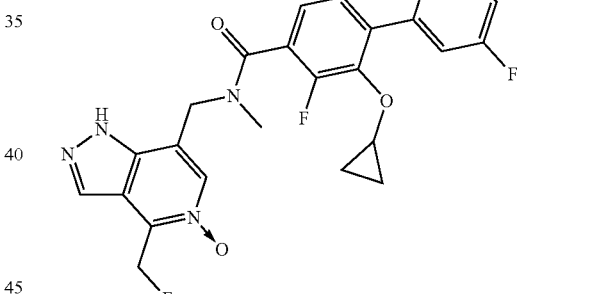 | 050 |
| 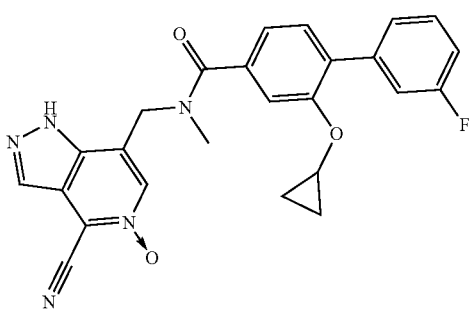 [SMILES: CN(Cc1c[n+]([O-])c(C#N)c2cn[nH]c12)C(=O)c1ccc(-c2cccc(F)c2)c(OC2CC2)c1] | 051 |

TABLE 2-continued

| Structure | No. |
|---|---|
| (structure) | 052 |
| (structure) | 053 |
| (structure) | 054 |
| (structure) | 055 |

TABLE 2-continued

| Structure | No. |
|---|---|
| (structure) | 056 |
| (structure) | 057 |
| (structure) | 058 |
| (structure) | 059 |

TABLE 2-continued

| Structure | No. |
|---|---|
| 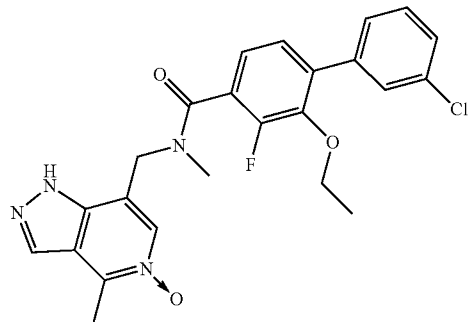 [SMILES: CCOc1c(-c2cccc(Cl)c2)ccc(C(=O)N(C)Cc2c[n+]([O-])c(C)c3cn[nH]c23)c1F] | 060 |
| 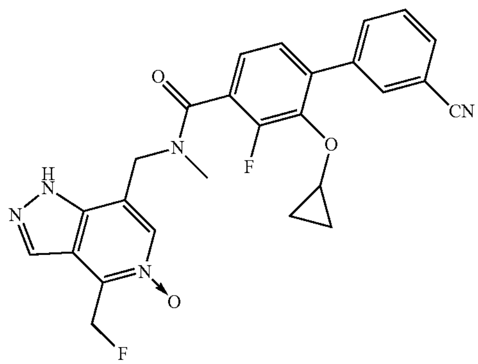 [SMILES: CN(Cc1c[n+]([O-])c(CF)c2cn[nH]c12)C(=O)c1ccc(-c2cccc(C#N)c2)c(OC2CC2)c1F] | 061 |
| 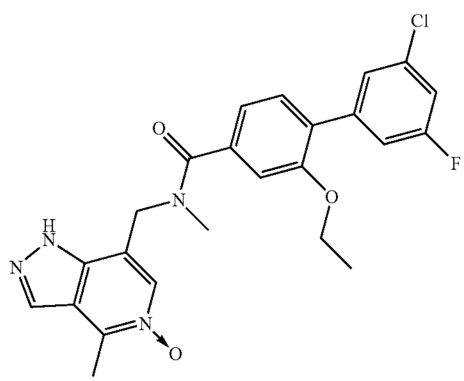 [SMILES: CCOc1cc(C(=O)N(C)Cc2c[n+]([O-])c(C)c3cn[nH]c23)ccc1-c1cc(F)cc(Cl)c1] | 062 |
| 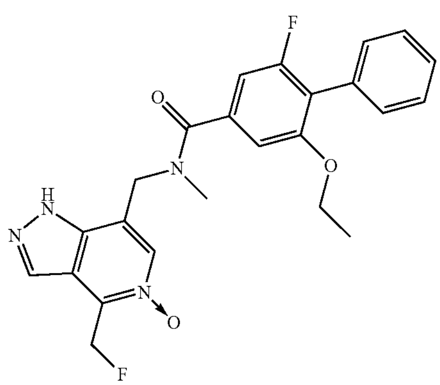 [SMILES: CCOc1cc(C(=O)N(C)Cc2c[n+]([O-])c(CF)c3cn[nH]c23)cc(F)c1-c1ccccc1] | 063 |
| | 064 |
| | 065 |
| | 066 |

TABLE 2-continued
| Structure | No. |
|---|---|
| 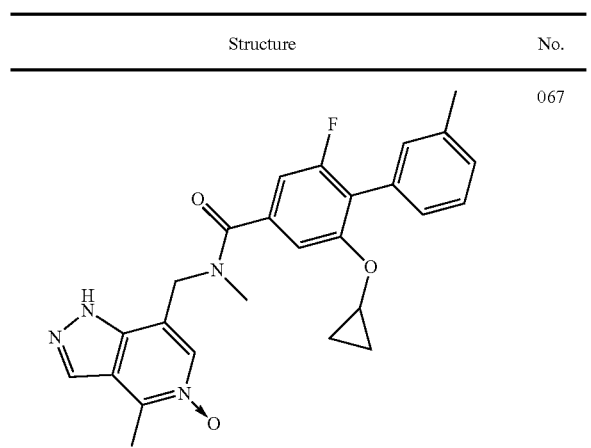 | 067 |
| 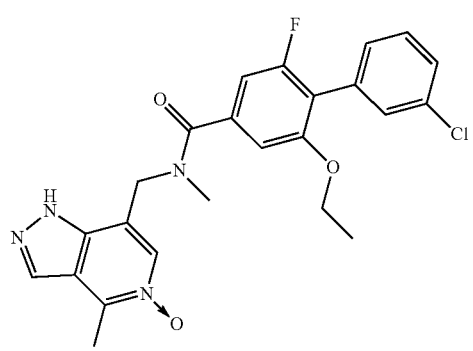 [SMILES: CCOc1cc(C(=O)N(C)Cc2c[n+]([O-])c(C)c3cn[nH]c23)cc(F)c1-c1cccc(Cl)c1] | 068 |
| 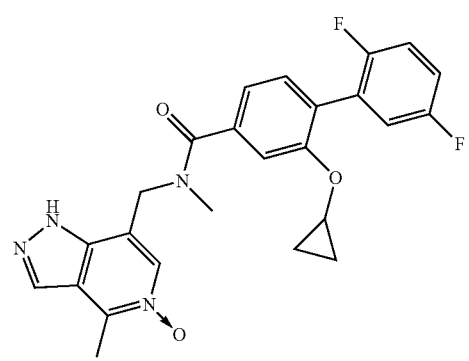 [SMILES: Cc1c2cn[nH]c2c(CN(C)C(=O)c2ccc(-c3cc(F)ccc3F)c(OC3CC3)c2)c[n+]1[O-]] | 069 |
| 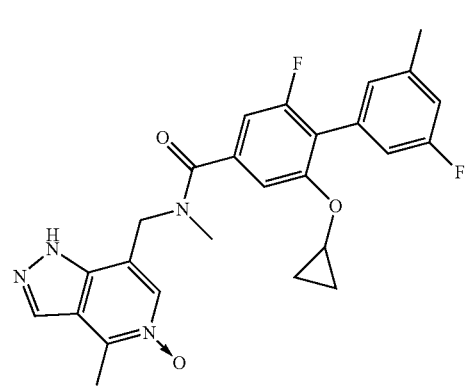 [SMILES: Cc1cc(F)cc(-c2c(F)cc(C(=O)N(C)Cc3c[n+]([O-])c(C)c4cn[nH]c34)cc2OC2CC2)c1] | 070 |
TABLE 2-continued
| Structure | No. |
|---|---|
| 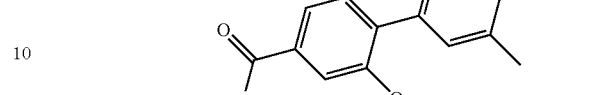 | 071 |
| 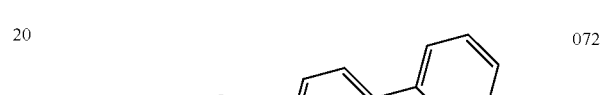 | 072 |
| 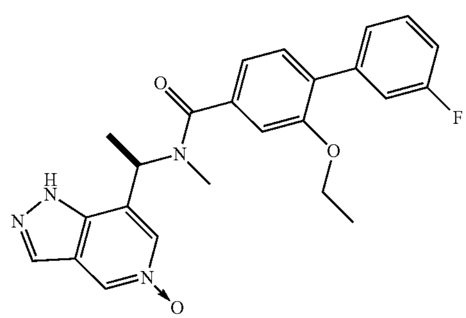 [SMILES: CCOc1cc(C(=O)N(C)[C@H](C)c2c[n+]([O-])cc3cn[nH]c23)ccc1-c1cccc(F)c1] | 073 |
| 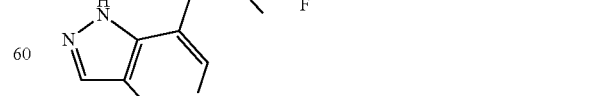 | 074 |

TABLE 2-continued

| Structure | No. |
|---|---|
| (structure) | 075 |
| (structure) | 076 | or a pharmaceutically acceptable salt thereof.

In still another embodiment, the compound of Formula I is selected from the group consisting of a compound in Table 3.

TABLE 3

| Structure | No. |
|---|---|
| (structure) | 077 |
| (structure) | 078 | or a pharmaceutically acceptable salt thereof.

In another aspect, provided herein is a pharmaceutical composition comprising a compound described herein, or a pharmaceutically acceptable salt thereof, and a pharmaceutically acceptable carrier.

The compounds disclosed herein may exist as tautomers and optical isomers (e.g., enantiomers, diastereomers, diastereomeric mixtures, racemic mixtures, and the like).

It is generally well known in the art that any compound that will be converted in vivo to provide a compound disclosed herein is a prodrug within the scope of the present disclosure.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

In embodiments, the compounds provided herein have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Methods of Treatment

In an aspect, provided herein is a method of inhibiting NLRP3 inflammasome in a subject in need thereof, comprising administering to the individual a therapeutically effective amount of a compound disclosed herein.

In another aspect, provided herein is a method of treating inflammation in a subject in need thereof, comprising administering to the individual a therapeutically effective amount of a compound disclosed herein.

In another aspect, provided herein is a method of treating inflammaging in a subject in need thereof, comprising administering to the individual a therapeutically effective amount of a compound disclosed herein.

In another aspect, provided herein is a method of treating cryopyrin-associated periodic syndrome (CAPS) in a subject in need thereof, comprising administering to the individual a therapeutically effective amount of a compound disclosed herein.

In an embodiment, the CAPS is selected from the group consisting of familial cold autoinflammatory syndrome, Muckle-Wells syndrome, and neonatal-onset multisystem inflammatory disease.

In another aspect, provided herein is a method of treating a dermatologic disease in a subject in need thereof, comprising administering to the individual a therapeutically effective amount of a compound disclosed herein.

In an embodiment, the dermatologic disease is selected from the group consisting of psoriasis, urticaria, skin photoaging, and eczema.

Also provided herein is a method of using the compounds provided herein for treatment or amelioration of aging or an aging-related condition negatively impacting longevity or quality of life, wherein the aging-related condition negatively impacting longevity or quality of life is selected from the group consisting of inflammation, anemia, hyperglycemia, dyslipidemia, hyperinsulinemia, insulin resistance, immunosuppression, liver disease, iron overload, hypertriglyceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1.alpha., IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNF.alpha.), vascular cell adhesion molecule (VCAM-1), and vascular endothelial growth factor 2 (VEGFR$^2$), comprising: administering to a subject in need thereof a compound provided herein.

In an aspect, provided herein is a method of reversing a normal aging process in subject comprising administering to the subject a therapeutically effective amount of a compound provided herein or a pharmaceutically acceptable salt thereof.

In another aspect, provided herein is a method of reversing a normal aging process in subject comprising administering to the subject a pharmaceutical composition comprising a therapeutically effective amount of a compound provided herein or a pharmaceutically acceptable salt thereof.

In yet another aspect, provided herein is a method of extending lifespan of a subject comprising administering to the subject a therapeutically effective amount of a compound provided herein or a pharmaceutically acceptable salt thereof.

In still another aspect, provided herein is a method of extending lifespan of a subject comprising administering to the subject a pharmaceutical composition comprising a therapeutically effective amount of a compound provided herein or a pharmaceutically acceptable salt thereof.

In another aspect, provided herein is a method to slow down and mitigate the aging process in a subject comprising administering to the subject a therapeutically effective amount of a compound provided herein or a pharmaceutically acceptable salt thereof.

In another aspect, provided herein is a method of inhibiting or modulating the pro-inflammatory pathway in a cell comprising contacting the cell with a compound provided herein, or a pharmaceutically acceptable salt thereof. In yet another aspect, provided herein is a method of inhibiting or modulating NLRP3 in a cell comprising contacting the cell with a compound provided herein, or a pharmaceutically acceptable salt thereof.

Treatment of a cell (in vitro or in vivo) that expresses a NLRP3 inflammasome with a compound provided herein can result in inhibiting the pro-inflammatory pathway and inhibiting downstream events related to the signaling pathway such as inflammation or inflammaging.

In another aspect, provided herein is a method of treating a neurosensory disease in a subject in need thereof, comprising administering to the individual a therapeutically effective amount of a compound disclosed herein.

In an embodiment, the neurosensory disease is selected from the group consisting of hearing loss, hearing injury, and ocular disease. In an embodiment, the ocular disease is retinal and optic nerve injury.

In yet another aspect, provided herein is a method of treating an inflammatory disorder in a subject in need thereof, comprising administering to the individual a therapeutically effective amount of a compound disclosed herein.

In an embodiment, the inflammatory disorder is selected from the group consisting of allergy, asthma, atopic dermatitis, atherosclerosis, autoimmune diseases, coeliac disease, chronic inflammation, glomerulonephritis, hepatitis, inflammatory bowel disease, preperfusion injury, SARS-CoV-2 infection, transplant rejection, heart disease, diabetes, arthritis, Crohn's disease, ulcerative colitis, non-alcoholic steatohepatitis (NASH), gout, coronary artery disease, rheumatoid arthritis, intestinal disorders, and acute respiratory distress syndrome (ARDS).

In another embodiment, the inflammatory disorder is a neuroinflammatory disease. In yet another embodiment, the inflammatory disorder is inner ear inflammation.

In an embodiment, a chronic inflammation comprises a tissue inflammation. Tissue inflammation is a chronic inflammation that is confined to a particular tissue or organ. In an embodiment, a tissue inflammation comprises, e.g., a skin inflammation, ocular inflammation, a muscle inflammation, a tendon inflammation, a ligament inflammation, a bone inflammation, a cartilage inflammation, a lung inflammation, a heart inflammation, a liver inflammation, a pancreatic inflammation, a kidney inflammation, a bladder inflammation, a stomach inflammation, an intestinal inflammation, a neuron inflammation, and a brain inflammation.

In another embodiment, a chronic inflammation comprises a systemic inflammation. Although the processes involved are identical to tissue inflammation, systemic inflammation is not confined to a particular tissue but in fact overwhelms the body, involving the endothelium and other organ systems. When it is due to infection, the term sepsis is applied, with the terms bacteremia being applied specifically for bacterial sepsis and viremia specifically to viral sepsis. Vasodilation and organ dysfunction are serious problems associated with widespread infection that may lead to septic shock and death.

In yet another embodiment, a chronic inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In still another aspect, provided herein is a method of treating an age-related disorder in a subject in need thereof, comprising administering to the individual a therapeutically effective amount of a compound disclosed herein.

In an embodiment, the age-related disorder is selected from the group consisting of neurodegeneration, cardiovascular disease, insulin resistance, diabetes, osteoporosis, osteoarthritis, cognitive decline, dementia, frailty, cataracts, arthritis, obesity, hypertension, angina, congestive heart failure, dyslipidemia, myocardial infarction, vascular disease, respiratory disease, kidney disease, cerebrovascular disease, peripheral vascular disease, Alzheimer's disease, cardiac diastolic dysfunction, benign prostatic hypertrophy, aortic aneurysm, and emphysema.

In another aspect, provided herein is a method of treating a metabolic condition in a subject in need thereof, comprising administering to the individual a therapeutically effective amount of a compound disclosed herein.

In an embodiment, the metabolic condition is selected from the group consisting of diabetes, obesity, cystic fibrosis, and hyperthyroidism.

In yet another aspect, provided herein is a method of treating a neurodegenerative disease in a subject in need thereof, comprising administering to the individual a therapeutically effective amount of a compound disclosed herein.

In an embodiment, the neurodegenerative disease is selected from the group consisting of Alzheimer's disease, Parkinson's disease, Huntington's disease, multiple sclerosis (MS), amyotrophic lateral sclerosis (ALS), and Batten disease.

In an aspect, provided herein is a method of treating a disease or disorder of the inner ear in a subject in need thereof, comprising administering to the individual a therapeutically effective amount of a compound disclosed herein.

In an embodiment, the disease or disorder of the inner ear is selected from the group consisting of hearing loss, hearing impairment, vertigo, Meniere's disease, and tinnitus. In another embodiment, the disease of the inner ear is hearing loss. In yet another embodiment, the disease of the inner ear is hearing impairment.

In another embodiment, the hearing loss is age-related, noise-induced, or the result of a viral infection. In yet another embodiment, the viral infection is Zika virus or coronavirus.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value.

In an embodiment of the methods, the subject is a human.

In another aspect, the disclosure provides a compound disclosed herein, or a pharmaceutically acceptable salt thereof, for use in the manufacture of a medicament for treating or preventing a disease in which NLRP3 inflammasome plays a role.

In an aspect, provided herein is a method of treating a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer.

Therefore, in an aspect, provided herein is a method of treating cancer in a subject in need thereof comprising administering to the subject a therapeutically effective amount of a compound disclosed herein, or a pharmaceutically acceptable salt thereof.

In an embodiment, the cancer is selected from the group consisting of breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon, rectum, large intestine, rectum, brain and central nervous system, chronic myeloid leukemia (CML), and leukemia.

In another embodiment, the cancer is selected from the group consisting of myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

In an embodiment, the cancer is selected from the group consisting of prostate cancer, colon cancer, lung cancer, squamous cell cancer of the head and neck, esophageal cancer, hepatocellular carcinoma, melanoma, sarcoma, gastric cancer, pancreatic cancer, ovarian cancer, breast cancer.

In an embodiment, the cancer is selected from the group consisting of tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in treating are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In another aspect, provided herein is the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

Administration/Dosages/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present disclosure can be administered intratympanically, wherein a long, narrow, bore needle is passed through the ear canal and through the eardrum to administer medications into the middle ear space where they are absorbed by the inner ear.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting NLRP3 inflammasome activity selected from one or more compounds of disclosed herein, or pharmaceutically acceptable salts thereof, and instructions for use in treating a disorder associated with NLRP3 inflammasomes.

In another aspect, the disclosure provides a kit comprising a compound capable of inhibiting NLRP3 inflammasome activity selected from a compound disclosed herein, or a pharmaceutically acceptable salt thereof.

In yet another aspect, provided herein is a kit comprising a compound disclosed herein, or a pharmaceutically acceptable salt thereof for the treatment of any of the indications disclosed herein.

Those skilled in the art will recognize or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Abbreviations
ACN acetonitrile
AcOH acetic acid
DCM dichloromethane
DMAP 4-dimethylaminopyridine
DMF dimethylformamide
DMSO dimethylsulfoxide
dppf 1,1'-bis(diphenylphosphino)ferrocene
EDCI 1-ethyl-3-(3-dimethylaminopropyl)carbodiimide
EtOAc ethyl acetate
EtOH ethanol
HPLC high-performance liquid chromatography
LAH lithium aluminum hydride
LCMS liquid chromatography-mass spectrometry
m-CPBA meta-chloroperoxybenzoic acid
MeOH methanol
NMR nuclear magnetic resonance
PE petroleum ether
SEM-Cl 2-(trimethylsilyl)ethoxymethyl chloride
TEA triethylamine
TFA trifluoroacetic acid
THF tetrahydrofuran
TLC thin layer chromatography Example 1: Synthetic Procedures

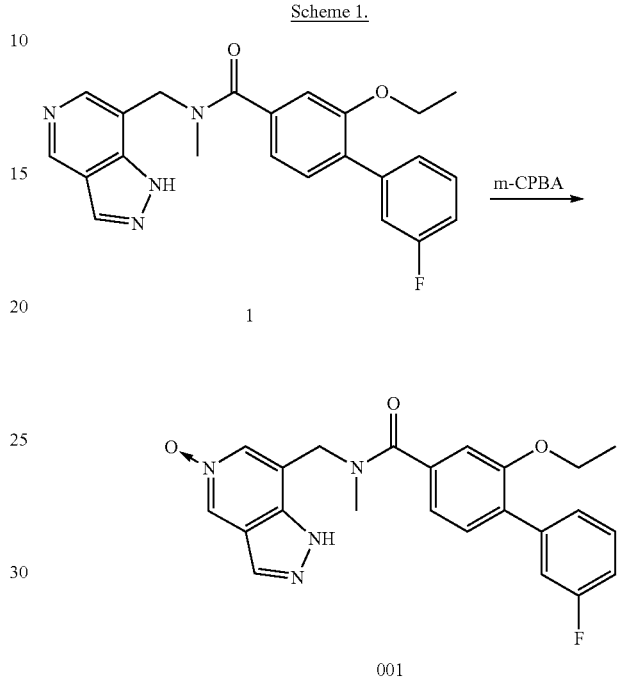

Scheme 1.

To a solution of Compound 1 (20 mg, 49.45 umol, 1 eq) in DCM (1 mL) was added m-CPBA (10.04 mg, 49.45 umol, 85% purity, 1 eq) under 0° C., then the mixture was stirred at 20° C. for 1 hr. The reaction mixture was poured into water (1 mL) and extracted by dichloromethane (3×2 mL), the combined organic phase was dried and concentrated under vacuum to give a residue. The residue was purified by prep-HPLC (column: Phenomenex luna C18 150*25 mm*10 um;mobile phase: [water(FA)-ACN];B %: 26%-56%,9 min), the purified solution was lyophilized to give a white solid. The white solid was purified by prep-HPLC (column: Waters xbridge 150*25 mm 10 um;mobile phase: [water(NH$_4$HCO3)-ACN];B %: 23%-53%,8 min), the purified solution was lyophilized to give a white solid. Compound 001 (16 mg, 36.08 umol, 72.95% yield, 94.8% purity) was obtained as a white solid. LCMS: Rt=0.527 min, m/z=421.2 (M+H)$^+$ $^1$H NMR (400 MHz, CHLOROFORM-d) δ=12.58-12.24 (m, 1H), 8.77 (d, J=1.3 Hz, 1H), 8.19-8.11 (m, 2H), 7.37 (td, J=3.0, 7.8 Hz, 2H), 7.31 (d, J=7.6 Hz, 2H), 7.12-7.01 (m, 3H), 4.89 (s, 2H), 4.08 (q, J=7.0 Hz, 2H), 3.10 (s, 3H), 1.38 (t, J=6.9 Hz, 3H).

Compound 003 was prepared in a similar manner to Scheme 1 and was obtained as brown solid (7.05 mg, 16.18 umol, 22.57% yield, and 99.72% purity). LCMS: Rt=0.482 min, m/z=435.3 (M+H$^+$). $^1$H NMR: (400 MHz, CHLOROFORM-d) δ=12.53-12.36 (m, 1H), 8.80 (s, 1H), 8.27 (s, 1H), 8.20 (s, 1H), 7.42 (s, 1H), 7.40 (s, 1H), 7.38-7.35 (m, 1H), 7.34 (s, 1H), 7.15-7.07 (m, 3H), 6.52-6.42 (m, 1H), 4.21-4.03 (m, 2H), 2.91 (s, 3H), 1.87 (d, J=7.1 Hz, 3H), 1.43 (t, J=6.9 Hz, 3H).

Scheme 2.

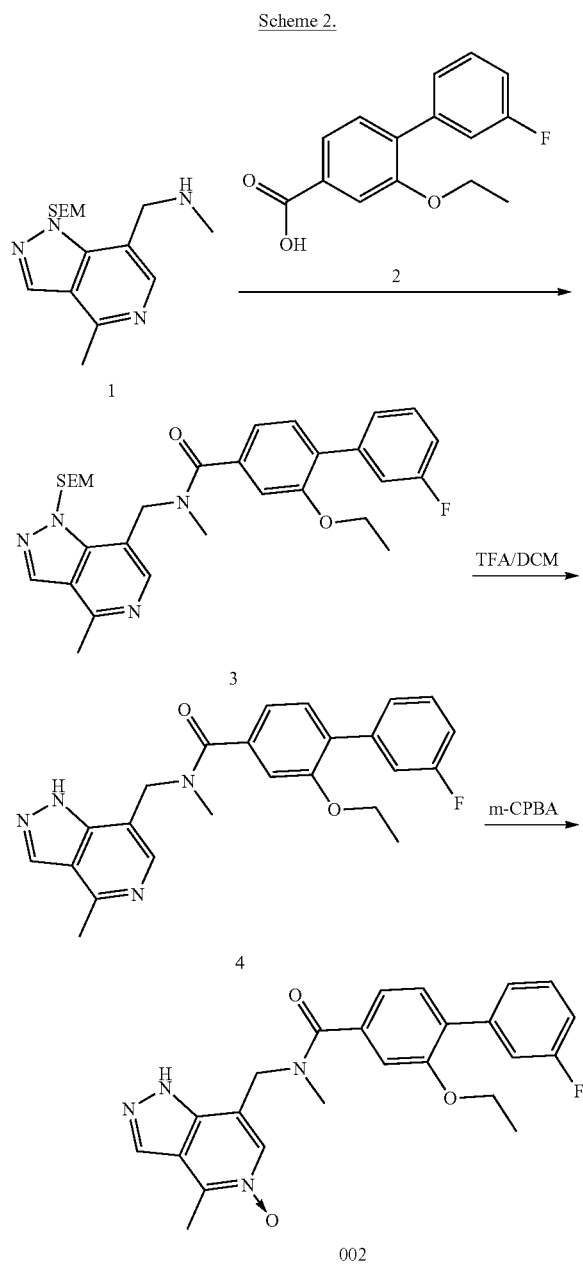

To a solution of compound 1 (260 mg, 848.35 umol, 1.1 eq) and compound 2 (200.72 mg, 771.23 umol, 1 eq) in DCM (5 mL) was added EDCI (221.77 mg, 1.16 mmol, 1.5 eq) and DMAP (9.42 mg, 77.12 umol, 0.1 eq), the mixture was stirred at 20° C. for 12 hr. Evaporate the solution on a water bath under reduced pressure using a rotary evaporator. The residue was purified by prep-TLC (SiO$_2$, Petroleum ether:Ethyl acetate=0:1, Rf=0.4). Compound 3 (341 mg, 576.70 umol, 74.78% yield, 92.8% purity) was obtained as white solid. LCMS: Rt=0.583 min, m/z=549.1 (M+H$^+$)

To a solution of compound 3 (341 mg, 576.70 umol, 92.8% purity, 1 eq) in DCM (3 mL) was added TFA (4.29 g, 37.60 mmol, 2.78 mL, 65.20 eq) at 0° C., the mixture was stirred at 20° C. for 1 hr. The mixture was concentrated to give a crude product, the crude product was dissolved in MeOH (10 mL), and 1 g Na$_2$CO$_3$ was added to the mixture, the mixture was stirred at 20° C. for 0.5 h, then the mixture was filtered and the filtrate was concentrated to give a crude product. The residue was purified by prep-TLC (SiO$_2$, Dichloromethane: Methanol=10:1, Rf=0.4). Compound 4 (146 mg, 348.90 umol, 60.50% yield, N/A purity) was obtained as colourless oil. LCMS: Rt=0.642 min, m/z=419.1 (M+H$^+$)

To a solution of compound 4 (146 mg, 348.90 umol, 1 eq) in DCM (10 mL) was added m-CPBA (184.31 mg, 1.05 mmol, 98% purity, 3 eq) at 0° C., the mixture was stirred at 30° C. for 12 hr. After the reaction was completed, the mixture was filtered and the cake was dissolved in saturated Na$_2$SO$_3$ solution (50 mL) slowly, the filtrate was concentrated to give a crude product. The crude product was purified by Prep-HPLC (NH$_4$.H$_2$O, column: Welch Xtimate C18 150*25 mm*5 um; mobile phase: [water (NH$_3$H$_2$O)-ACN];B %: 25%-55%,8 min), the purified solution was lyophiilized to give a white solid. Compound 002 (46.91 mg, 104.79 umol, 30.03% yield, 97.05% purity) was obtained as white solid. LCMS: Rt=0.665 min, m/z=453.3 (M+Na$^+$). $^1$H NMR (400 MHz, CHLOROFORM-d) δ=12.54-12.22 (m, 1H), 8.45-8.27 (m, 1H), 8.19 (s, 1H), 7.41-7.34 (m, 2H), 7.33-7.28 (m, 2H), 7.11-7.02 (m, 3H), 4.98-4.80 (m, 2H), 4.18-3.93 (m, 2H), 3.09 (s, 3H), 2.95-2.78 (m, 3H), 1.38 (t, J=6.9 Hz, 3H).

Compound 005 was prepared in a similar manner to Scheme 2 (11.9 mg, 26.55 umol, 47.62% yield, 99.6% purity) and was obtained as a white solid. LCMS: Rt=0.384 min, m/z=447.3 (M+H)$^+$1H NMR (400 MHz, CHLOROFORM-d) δ=8.35-8.28 (m, 1H), 8.20-8.13 (m, 1H), 7.47-7.40 (m, 1H), 7.38-7.29 (m, 2H), 7.24-7.20 (m, 1H), 7.20-7.15 (m, 1H), 7.13-7.08 (m, 1H), 7.06-6.99 (m, 1H), 4.93-4.84 (m, 2H), 3.81-3.71 (m, 1H), 3.14-3.05 (m, 3H), 2.89-2.81 (m, 3H), 0.84-0.72 (m, 4H).

Compound 008 was prepared in a similar manner to Scheme 2 (5.7 mg, 12.67 umol, 54.69% yield, 99.5% purity) and was obtained as a white solid, LCMS: Rt =0.401 min, m/z=448.2 (M+H)+1H NMR (400 MHz, CHLOROFORM-d) δppm 12.35-12.60 (m, 1 H) 8.39-8.42 (m, 1 H) 8.24-8.26 (m, 1 H) 7.94-7.96 (m, 1 H) 7.71 (d, J=1.25 Hz, 1 H) 7.67-7.70 (m, 1 H) 7.08-7.11 (m, 2 H) 4.88-4.92 (m, 2 H) 4.19-4.26 (m, 2 H) 3.08-3.11 (m, 3 H) 2.92 (s, 3 H) 1.54-1.59 (m, 3 H).

Compound 013 was prepared in a similar manner to Scheme 2 (11.81 mg, 27.18 umol, 22.75% yield, 100% purity) and was obtained as a white solid. LCMS: Rt=0.529 min, m/z=435.2 (M+H+). 1H NMR: (400 MHz, CHLOROFORM-d) δ=13.39-13.05 (m, 1H), 9.52 (d, J=1.8 Hz, 1H), 8.51 (s, 1H), 7.39 (br dd, J=2.9, 5.5 Hz, 2H), 7.34-7.30 (m, 3H), 7.11-7.05 (m, 2H), 5.19 (br s, 2H), 4.12-4.04 (m, 2H), 3.14 (s, 3H), 3.06 (d, J=2.1 Hz, 3H), 1.39 (br s, 3H).

Compound 018 was prepared in a similar manner to Scheme 2 (14.1 mg, 28.69 umol, 38.97% yield) and was obtained as white solid. LCMS: Rt=0.545 min, m/z=492.3 [M+H$^+$]1H NMR (400 MHz, CHLOROFORM-d) δ=12.59-12.43 (m, 1H), 8.38 (s, 1H), 8.28 (dd, J=2.4, 7.7 Hz, 1H), 8.24 (s, 1H), 7.71-7.65 (m, 1H), 7.38 (d, J=7.8 Hz, 1H), 7.16 (dd, J=8.6, 11.7 Hz, 1H), 7.09 (dd, J=1.4, 7.8 Hz, 1H), 7.06 (s, 1H), 6.83-6.71 (m, 1H), 4.89 (s, 2H), 4.12-4.02 (m, 2H), 3.10 (s, 3H), 3.06 (d, J=4.1 Hz, 3H), 2.92 (s, 3H), 1.37 (t, J=6.9 Hz, 3H).

Compound 034 was prepared in a similar manner to Scheme 2. Compound 034 (9.8 mg, 20.90 umol, 31.55% yield, 100% purity) was isolated as a white solid. LCMS: Rt=0.407 min, m/z=469.2(M+H)+1H NMR (400 MHz, CHLOROFORM-d) δ=12.26-12.12 (m, 1H), 8.23 (s, 1H), 8.15 (s, 1H), 7.43-7.36 (m, 1H), 7.15 (s, 1H), 7.12-7.07 (m, 1H), 7.07-7.02 (m, 1H), 7.01-6.97 (m, 1H), 6.95-6.91 (m, 1H), 4.85 (s, 2H), 3.99 (q, J=6.9 Hz, 2H), 3.12-3.06 (m, 3H), 2.84 (s, 3H), 1.28-1.22 (m, 3H).

Compound 037 was prepared in a similar manner to Scheme 2 and was obtained as a white solid. LCMS: Rt=0.431 min, m/z=485.4(M+H)+1H NMR (400 MHz, CHLOROFORM-d) δ=12.35 (s, 1H), 8.28 (s, 1H), 8.19-8.16 (m, 1H), 7.38-7.37 (m, 1H), 7.36 (s, 1H), 7.28-7.27 (m, 1H), 7.18-7.16 (m, 1H), 7.16-7.14 (m, 1H), 6.94-6.92 (m, 1H), 4.85 (s, 2H), 4.03-3.96 (m, 2H), 3.10 (s, 3H), 2.86 (s, 3H), 1.26 (t, J=6.9 Hz, 3H).

Scheme 3

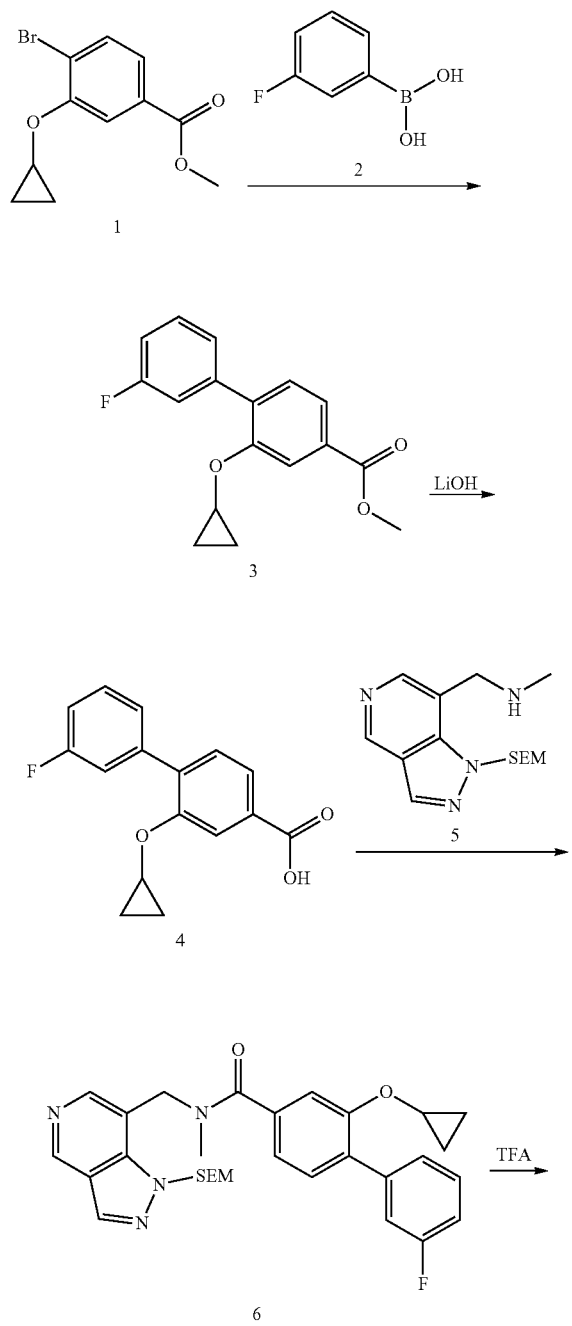

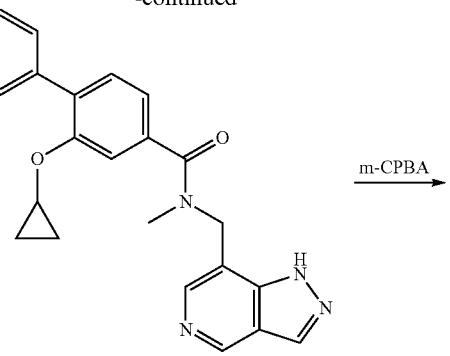

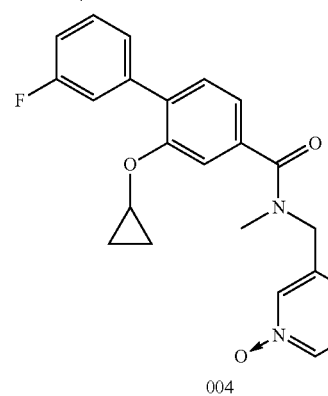

To a solution of compound 1 (400 mg, 1.48 mmol, 1 eq) in dioxane (4 mL) was added compound 2 (412.88 mg, 2.95 mmol, 2 eq), Pd(dppf)Cl₂·CH₂Cl₂ (120.49 mg, 147.54 umol, 0.1 eq) and Cs₂CO₃ (961.45 mg, 2.95 mmol, 2 eq), the reaction mixture was stirred at 100° C. for 12 h under N₂. The reaction mixture was filtered, the filtrate was concentrated to give a crude product. The crude product was purified by column chromatography on silica gel eluted with petroleum ether: ethyl acetate=1:0 to 20/1 (desired compound Rf=0.5). Compound 3 (375 mg, 1.21 mmol, 81.67% yield, 92% purity) was obtained as brown oil. LCMS: Rt=0.642 min, m/z =287.0 (M+H+)

To a solution of compound 3 in H₂O (2 mL) and MeOH (6 mL) was added LiOH·H₂O (153.90 mg, 3.67 mmol, 3 eq), the reaction mixture was stirred at 20° C. for 12 hr. Acidify the reaction mixture by adding 1 mol/L HCl to pH=5. Then the reaction mixture was concentrated to give a crude product. The crude product was used directly to the next step without purification. Compound 4 (319 mg, 1.04 mmol, 84.99% yield, 88.68% purity) was obtained as white solid. LCMS: Rt=0.571 min, m/z=273.0 (M+H+)

To a solution of compound 4 (90 mg, 290.89 umol, 88% purity, 1 eq) in DCM (2 mL) was added compound 5 (102.08 mg, 349.06 umol, 1.2 eq), EDCI (83.65 mg, 436.33 umol, 1.5 eq) and DMAP (3.55 mg, 29.09 umol, 0.1 eq), the reaction mixture was stirred at 20° C. for 12 hr. The reaction mixture was filtered, the filtrate was concentrated to give a crude product. The crude product was purified by prep-TLC (petroleum ether: ethyl acetate=0:1, desired compound Rf=0.5). Compound 6 ((117 mg, 188.33 umol, 64.74% yield, 88% purity) was obtained as colorless oil. LCMS: Rt=0.610 min, m/z=547.1(M−H+)

To a solution of compound 6 (117 mg, 188.33 umol, 88% purity, 1 eq) in DCM (2 mL) was added TFA (3.08 g, 27.01 mmol, 2 mL, 143.43 eq), the reaction mixture was stirred at 20° C. for 2 hr. The reaction mixture was filtered, the filtrate was concentrated to give a crude product. The crude product was purified by prep-TLC (dichloromethane: methanol=10: 1, desired compound Rf=0.5). Compound 7 ((98 mg, crude) was obtained as colorless oil. LCMS: Rt=0.491 min, m/z=417.0(M–H+)

To a solution of compound 7 (98 mg, 235.32 umol, 1 eq) in DCM (2 mL) was added m-CPBA (143.33 mg, 705.97 umol, 85% purity, 3 eq) at 0° C., the reaction mixture was stirred at 20° C. for 2 hr. After the reaction was completed, the mixture was poured into saturated $Na_2SO_3$ solution (25 mL) and extracted with EtOAc (25 mL×3), the combined organic phase was washed with brine (50 ml), dried over anhydrous $Na_2SO_4$, and concentrated to give a crude product. The crude product was purified by prep-HPLC (column: Phenomenex luna C18 150*25 mm*10 um; mobile phase: [water (FA)-ACN]; B %: 38%-68%, 9 min). After prep-HPLC purification, the eluent was concentrated to remove organic solvents. The residual aqueous solution was lyophilized to give white solid. 004 (21.68 mg, 49.13 umol, 20.88% yield, 98% purity) was obtained as white solid. LCMS: Rt=0.503 min, m/z=433.0 (M+H+). $^1$H NMR (400 MHz, CHLOROFORM-d) δ=9.09-8.98 (m, 1H), 8.51-8.42 (m, 1H), 8.38-8.30 (m, 1H), 7.49-7.44 (m, 1H), 7.40-7.34 (m, 2H), 7.27-7.25 (m, 1H), 7.25-7.22 (m, 1H), 7.24-7.18 (m, 2H), 7.17-7.11 (m, 1H), 7.09-7.03 (m, 1H), 5.00 (s, 2H), 3.83-3.76 (m, 1H), 3.21-3.15 (m, 3H), 0.86-0.82 (m, 2H), 0.81-0.76 (m, 2H).

Compound 010 was prepared in a similar manner to Scheme 3 (8.2 mg, 17.84 umol, 38.94% yield, 98.462% purity) and was obtained as white solid. LCMS: Rt=0.637 min, m/z=453.2 (M+H$^+$). $^1$H NMR (400 MHz, CHLOROFORM-d) δ=12.46-12.16 (m, 1H), 8.35 (s, 1H), 8.21 (s, 1H), 7.43-7.36 (m, 1H), 7.19 (d, J=7.6 Hz, 1H), 7.14 (br d, J=9.6 Hz, 1H), 7.11-7.05 (m, 1H), 6.89-6.84 (m, 2H), 4.99-4.77 (m, 2H), 4.11-3.97 (m, 2H), 3.11 (s, 3H), 2.93-2.78 (m, 3H), 1.32 (t, J=6.9 Hz, 3H).

Compound 011 was prepared in a similar manner to Scheme 3 (5.23 mg, 11.38 umol, 16.28% yield, 100% purity) and was obtained as light yellow solid. LCMS: Rt=0.407 min, m/z=460.2 (M+H$^+$) $^1$H NMR: (400 MHz, CHLOROFORM-d) δ=13.17-12.48 (m, 1H), 8.69-8.59 (m, 1H), 8.52-8.39 (m, 1H), 7.78-7.72 (m, 1H), 7.67 (br t, J=6.5 Hz, 2H), 7.58-7.51 (m, 1H), 6.95-6.81 (m, 2H), 4.95 (s, 2H), 4.06 (q, J=7.2 Hz, 2H), 3.17 (s, 3H), 3.09 (s, 3H), 1.33 (t, J=7.0 Hz, 3H).

Compound 014 was prepared in a similar manner to Scheme 3 (14 mg, 29.80 umol, 33.35% yield, 96.312% purity) and was obtained as white solid. LCMS: Rt=0.539 min, m/z=453.1 (M+H$^+$). $^1$H NMR: (400 MHz, CHLOROFORM-d) δ=12.83-12.02 (m, 1H), 8.35 (s, 1H), 8.23 (s, 1H), 7.35 (d, J=7.8 Hz, 1H), 7.13-6.99 (m, 4H), 6.81 (tt, J=2.3, 8.9 Hz, 1H), 4.89 (s, 2H), 4.09 (q, J=7.0 Hz, 2H), 3.09 (s, 3H), 2.91 (s, 3H), 1.40 (t, J=6.9 Hz, 3H).

Compound 017 was prepared in a similar manner to Scheme 3 (7.7 mg, 16.58 umol, 12.39% yield, 100% purity) and was obtained as a white solid. LCMS: Rt=0.440 min, m/z=465.2 (M+H)$^+$1H NMR (400 MHz, CHLOROFORM-d) δppm 8.34-8.44 (m, 1 H) 8.23 (s, 1 H) 7.44 (d, J=1.38 Hz, 1 H) 7.32 (br d, J=1.63 Hz, 1 H) 7.28-7.31 (m, 1 H) 7.18-7.21 (m, 1 H) 7.16-7.18 (m, 1 H) 7.11 (dd, J=7.75, 1.50 Hz, 1 H) 4.89-4.93 (m, 2 H) 3.75-3.80 (m, 1 H) 3.08-3.14 (m, 3 H) 2.90 (s, 3 H) 0.80-0.86 (m, 2 H) 0.73-0.79 (m, 2 H).

Compound 019 was prepared in a similar manner to Scheme 3 (6.9 mg, 14.24 umol, 16.68% yield, 100% purity) and was obtained as white solid. LCMS: Rt=0.567 min, m/z=485.2 (M+H$^+$) $^1$H NMR: (400 MHz, CHLOROFORM-d) δ=8.76-8.37 (m, 1H), 7.87 (s, 1H), 7.72-7.72 (m, 1H), 7.77-7.71 (m, 1H), 7.66-7.61 (m, 1H), 7.59-7.52 (m, 1H), 7.45-7.39 (m, 1H), 7.13 (d, J=7.8 Hz, 1H), 7.10-7.00 (m, 1H), 5.02-4.91 (m, 2H), 4.15-4.05 (m, 2H), 3.23-2.99 (m, 6H), 1.42-1.36 (m, 3H).

Compound 046 was prepared in a similar manner to Scheme 3 and was obtained as a white solid (13.1 mg, 27.13 umol, 63.07% yield, 99.6% purity). LCMS: Rt=0.429 min, m/z=481.3 (M+H)$^+$1H NMR (400 MHz, CHLOROFORM-d) δ=8.29 (s, 1H), 8.17 (s, 1H), 7.37-7.31 (m, 3H), 7.25-7.19 (m, 2H), 6.93-6.86 (m, 1H), 4.87 (s, 2H), 3.77-3.73 (m, 1H), 3.11 (s, 3H), 2.85 (s, 3H), 0.83-0.76 (m, 2H), 0.75-0.69 (m, 2H).

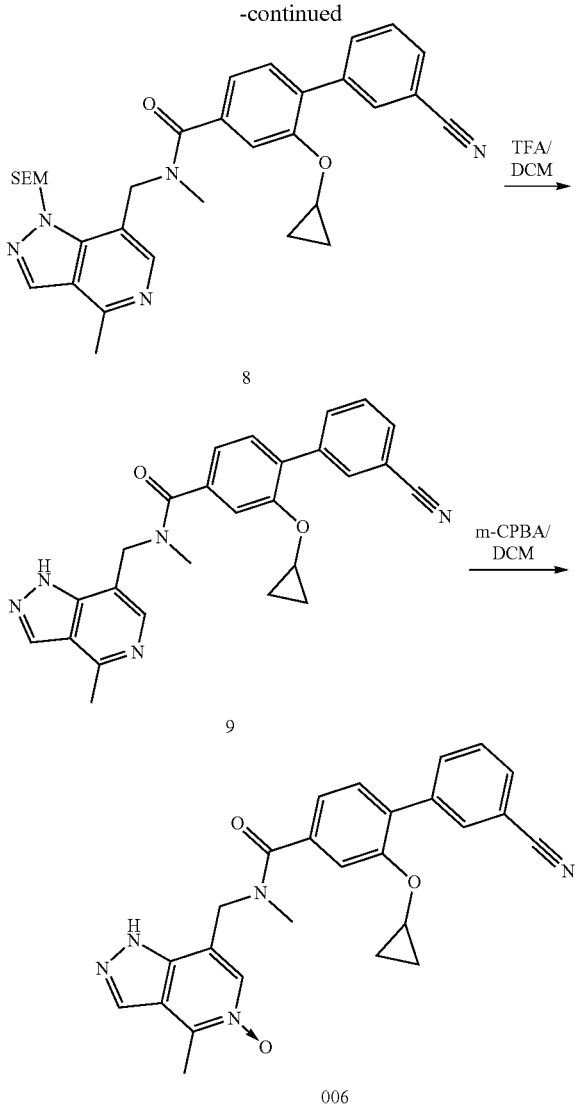

To solution of 1 (2.2 g, 10.38 mmol, 1 eq) in 2-MeTHF (30 mL) was added NaH (622.45 mg, 15.56 mmol, 60% purity, 1.5 eq) at 0° C., the mixture was stirred at 0° C. for 1 hr. Then SEM-Cl (2.08 g, 12.45 mmol, 2.20 mL, 1.2 eq) was added dropwise, the mixture was stirred at 20° C. for 12 hr. The mixture was poured into saturated NH$_4$Cl (200 mL) solution, and extracted with EtOAc (200 mL×3), the combined organic phase was washed with brine (200 mL), dried over anhydrous Na$_2$SO$_4$, and concentrated to give a crude product. The crude product was purified by colunm chromatography (SiO$_2$, Petroleum ether:Ethyl acetate=1:1). 2 (1.55 g, 4.52 mmol, 43.57% yield) was obtained as brown oil. LCMS: Rt=0.533 min, m/z=343.9 (M+H$^+$)

To a solution of 2 (1.55 g, 4.53 mmol, 1 eq) in MeOh (20 mL) was added Pd(OAc)$_2$ (203.32 mg, 905.62 umol, 0.2 eq), DPPF (502.06 mg, 905.62 umol, 0.2 eq) and TEA (2.29 g, 22.64 mmol, 3.15 mL, 5 eq), the mixture was stirred at 80° C. for 12 hr under CO (50 psi). After the reaction was completed, the mixture was filtered under N$_2$ and the filtrated was concentrated to give a crude product. The crude product was purified by colunm chromatography (SiO$_2$, Petroleum ether:Ethyl acetate=40/1 to 60/1). 3 (1.42 g, 4.41 mmol, 97.35% yield) was obtained as brown oil. LCMS: Rt=0.367 min, m/z=322.2 (M+H$^+$)

To a solution of 3 (1.42 g, 4.42 mmol, 1 eq) in 2-MeTHF (15 mL) was added LAH (251.47 mg, 6.63 mmol, 1.5 eq) at 0° C., the mixture was stirred at 0° C. for 1 hr. After the reaction was completed, the resulting mixture was added Na$_2$SO$_4$·10H$_2$O (2 g). Then the mixture was filtered and the filtrate was concentrated to give a crude product. The crude product was used for next step without further purification. 4 (1.1 g, crude) was obtained as yellow oil. LCMS: Rt=0.709 min, m/z=409.0 (M+Na$^+$)

To a solution of 4 (1.1 g, 3.75 mmol, 1 eq) in DCM (15 mL) was added MnO2 (6.52 g, 74.97 mmol, 20 eq), the mixture was stirred at 30° C. for 12 hr. After the reaction was completed, the mixture was filtered and the filtrated was concentrated to give a crude product. The crude product was purified by colunm chromatography (SiO$_2$, Petroleum ether: Ethyl acetate=40/1 to 60/1). 5 (821 mg, 2.82 mmol, 75.23% yield) was obtained as yellow oil. 4 (373 mg, 1.27 mmol, 33.91% yield) was obtained as yellow oil. LCMS: Rt=0.507 min, m/z=292.1 (M+H$^+$). $^1$H NMR: (400 MHz, CHLOROFORM-d) δ=10.20 (s, 1H), 8.79 (s, 1H), 8.27 (s, 1H), 6.23 (s, 2H), 3.52 (dd, J=7.8, 8.8 Hz, 2H), 2.92 (s, 3H), 0.87-0.82 (m, 2H), −0.09 (s, 9H)

To a solution of 5 (821 mg, 2.82 mmol, 1 eq) in MeOH (10 mL) was added MeNH 2 in THF (2 M, 7.04 mL, 5 eq) and AcOH (16.92 mg, 281.72 umol, 16.11 uL, 0.1 eq), the mixture was stirred at 20° C. for 1 hr. Then NaBH4 (319.75 mg, 8.45 mmol, 3 eq) was added to the solution, the mixture was stirred at 20° C. for 1 hr. The reaction mixture was quenched by saturated NH$_4$Cl aqueous (10 mL), the resulting mixture was concentrated under vacuum to give a residue. The crude product was used for next step without further purification. 6 (900 mg, crude) was obtained as yellow oil. LCMS: Rt=0.302 min, m/z=307.1 (M+H$^+$)

To a solution of compound 7 (80 mg, 286.44 umol, 1 eq) and 6 (131.68 mg, 429.66 umol, 1.5 eq) in DCM (2 mL) was added in EDCI (82.37 mg, 429.66 umol, 1.5 eq) and DMAP (3.50 mg, 28.64 umol, 0.1 eq). The mixture was stirred at 20° C. for 12 hr. Evaporate the solution on a water bath under reduced pressure using a rotary evaporator. The residue was purified by prep-TLC (SiO$_2$, EtOAc=1). The compound of 8 (78 mg, 128.23 umol, 44.77% yield, 93.337% purity) was obtained as colourless oil. LCMS: Rt=0.528 min, m/z=568.4 (M+H$^+$)

To a solution of compound 8 in DCM (1 mL) was added in TFA (770.00 mg, 6.75 mmol, 0.5 mL, 49.15 eq). The mixture was stirred at 20° C. for 12 h. Evaporate the solution on a water bath under reduced pressure using a rotary evaporator. The residue was purified by prep-TLC (SiO$_2$, DCM: MeOH=10:1). The compound of 9 (57 mg, 109.44 umol, 79.66% yield, 84% purity) was obtained as colourless oil. LCMS: Rt=0.543 min, m/z=438.2 (M+H$^+$)

To a solution of 4-(3-cyanophenyl)-3-(cyclopropoxy)-N-methyl-N-[(4-methyl-1H-pyrazolo[4,3-c]pyridin-7-yl)methyl]benzamide (57 mg, 130.29 umol, 1 eq) in DCM (2 mL) was added in m-CPBA (79.35 mg, 390.86 umol, 85% purity, 3 eq) at 0° C. The mixture was stirred at 30° C. for 12 h under N$_2$. After the reaction was completed, the mixture was filtered and the cake was dissolved in saturated Na$_2$SO$_3$ solution (10 mL) slowly, the filtrate was concentrated to give a crude product. The crude product was purified by prep-HPLC. Column: Welch Xtimate C18 150*25 mm*5 um;mobile phase: [water(NH$_3$H$_2$O)-ACN];B %: 15%-45%,8 min. lyophilized. The compound 006 (10.88 mg, 23.99 umol, 18.41% yield, 100% purity) was obtained as white solid. LCMS: Rt=0.461 min, m/z=454.2 (M+H$^+$). $^1$H NMR: (400 MHz, CHLOROFORM-d) δ=12.88-12.63 (m, 1H), 8.61-8.52 (m, 1H), 8.36 (br s, 1H), 7.78 (s, 1H), 7.69 (s, 1H), 7.63

(s, 1H), 7.52 (s, 1H), 7.45 (s, 1H), 7.34 (d, J=7.8 Hz, 1H), 7.14 (dd, J=1.4, 7.8 Hz, 1H), 4.96 (br s, 2H), 3.82-3.74 (m, 1H), 3.16 (s, 3H), 3.02 (br s, 3H), 0.85 (br d, J=6.3 Hz, 2H), 0.75 (br d, J=2.0 Hz, 2H).

The compound 007 was prepare in a similar manner to Scheme 4 (10.88 mg, 23.99 umol, 18.41% yield, 100% purity) and was obtained as white solid. LCMS: Rt=0.461 min, m/z=454.2 (M+H$^+$). $^1$H NMR: (400 MHz, CHLOROFORM-d) δ=12.88-12.63 (m, 1H), 8.61-8.52 (m, 1H), 8.36 (br s, 1H), 7.78 (s, 1H), 7.69 (s, 1H), 7.63 (s, 1H), 7.52 (s, 1H), 7.45 (s, 1H), 7.34 (d, J=7.8 Hz, 1H), 7.14 (dd, J=1.4, 7.8 Hz, 1H), 4.96 (br s, 2H), 3.82-3.74 (m, 1H), 3.16 (s, 3H), 3.02 (br s, 3H), 0.85 (br d, J=6.3 Hz, 2H), 0.75 (br d, J=2.0 Hz, 2H).

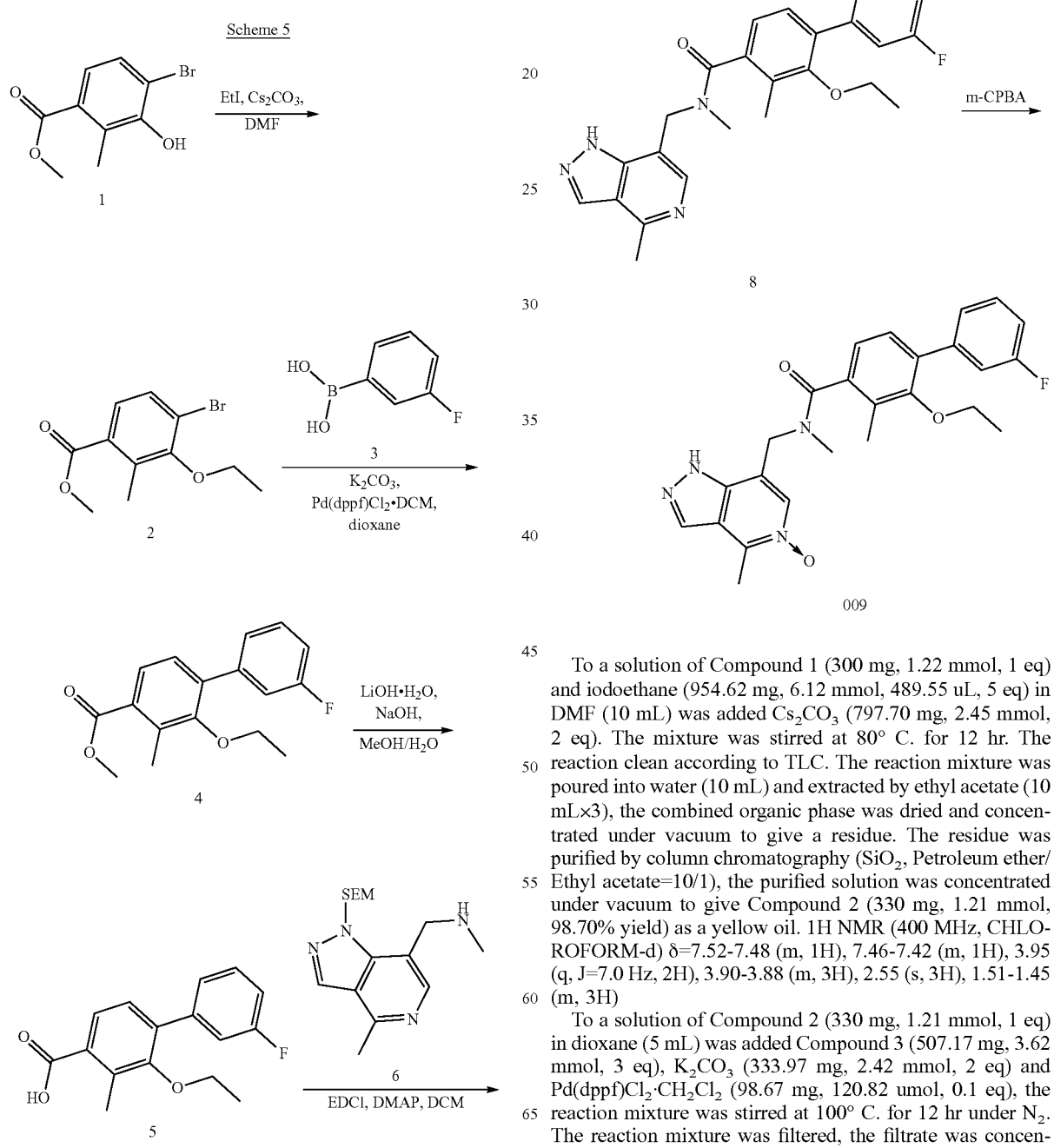

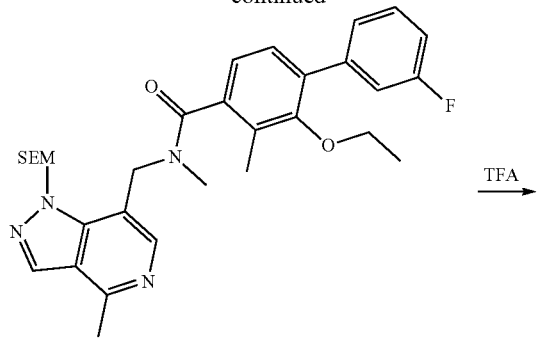

To a solution of Compound 1 (300 mg, 1.22 mmol, 1 eq) and iodoethane (954.62 mg, 6.12 mmol, 489.55 uL, 5 eq) in DMF (10 mL) was added Cs$_2$CO$_3$ (797.70 mg, 2.45 mmol, 2 eq). The mixture was stirred at 80° C. for 12 hr. The reaction clean according to TLC. The reaction mixture was poured into water (10 mL) and extracted by ethyl acetate (10 mL×3), the combined organic phase was dried and concentrated under vacuum to give a residue. The residue was purified by column chromatography (SiO$_2$, Petroleum ether/Ethyl acetate=10/1), the purified solution was concentrated under vacuum to give Compound 2 (330 mg, 1.21 mmol, 98.70% yield) as a yellow oil. 1H NMR (400 MHz, CHLOROFORM-d) δ=7.52-7.48 (m, 1H), 7.46-7.42 (m, 1H), 3.95 (q, J=7.0 Hz, 2H), 3.90-3.88 (m, 3H), 2.55 (s, 3H), 1.51-1.45 (m, 3H)

To a solution of Compound 2 (330 mg, 1.21 mmol, 1 eq) in dioxane (5 mL) was added Compound 3 (507.17 mg, 3.62 mmol, 3 eq), K$_2$CO$_3$ (333.97 mg, 2.42 mmol, 2 eq) and Pd(dppf)Cl$_2$·CH$_2$Cl$_2$ (98.67 mg, 120.82 umol, 0.1 eq), the reaction mixture was stirred at 100° C. for 12 hr under N$_2$. The reaction mixture was filtered, the filtrate was concentrated to give a crude product. The residue was purified by column chromatography (SiO$_2$, Petroleum ether/Ethyl acetate=20/1 to 10/1), the purified solution was concentrated under vacuum to give Compound 4 (270 mg, 936.48 umol, 77.51% yield) was obtained as a colorless oil. LCMS: Rt=0.549 min, m/z=289.0 (M+H)$^+$1H NMR (400 MHz, CHLOROFORM-d) δ=7.71-7.66 (m, 1H), 7.43-7.32 (m, 3H), 7.22 (d, J=8.0 Hz, 1H), 7.10-7.04 (m, 1H), 3.94-3.89 (m, 3H), 3.50 (q, J=7.0 Hz, 2H), 2.59-2.55 (m, 3H), 1.13 (t, J=7.1 Hz, 3H)

To a solution of Compound 4 (270 mg, 936.48 umol, 1 eq) in MeOH (3 mL) and H$_2$O (1 mL) was added LiOH·H$_2$O (117.89 mg, 2.81 mmol, 3 eq), the mixture was stirred at 20° C. for 1 hr. NaOH (112.37 mg, 2.81 mmol, 3 eq) was added the reaction, then the reaction was stirred at 20° C. for 1 hr. The organic solvents was evaporated under vacuum, the resulting mixture was acidified by 1N HCl to pH 4, then the mixture was filtered, and washed by water(10 mL), the filter cake was dried under vacuum to give Compound 5 (200 mg, 729.17 umol, 77.86% yield) as a white solid which was used directly in the next step. LCMS: Rt=0.338 min, m/z=273.1 (M–H)$^+$1H NMR (400 MHz, CHLOROFORM-d) δ=7.79-7.71 (m, 1H), 7.41-7.28 (m, 3H), 7.22-7.15 (m, 1H), 7.09-7.02 (m, 1H), 3.49-3.43 (m, 2H), 2.57 (s, 3H), 1.10 (t, J=7.0 Hz, 3H)

To a solution of Compound 5 (140 mg, 510.42 umol, 1 eq) in DCM (1 mL) was added Compound 6 (156.43 mg, 510.42 umol, 1 eq), EDCI (146.77 mg, 765.62 umol, 1.5 eq) and DMAP (6.24 mg, 51.04 umol, 0.1 eq), then the reaction mixture was stirred at 20° C. for 1 hr. The reaction mixture was concentrated under vacuum to give a residue. The residue was purified by prep-TLC (SiO$_2$, Petroleum ether/Ethyl acetate=0/1), the purified solution was concentrated under vacuum to give Compound 7 (120 mg, 213.24 umol, 41.78% yield) as a colorless oil. LCMS: Rt=0.484 min, m/z=563.3 (M+H)$^+$ To a solution of Compound 7 (140 mg, 248.78 umol, 1 eq) in TFA (1 mL) was stirred at 20° C. for 1 hr. The reaction mixture was basified by saturated NaHCO$_3$ aqueous (10 mL), then the reaction mixture was diluted with H$_2$O (10 mL) and extracted with EA (10 mL×3). The combined organic layers were washed with brine, dried over Na$_2$SO$_4$, filtered and concentrated under reduced pressure to give Compound 8 (100 mg, 231.22 umol, 92.94% yield) as a yellow oil which was used directly in the next step. LCMS: Rt=0.448 min, m/z=433.3 (M+H)$^+$ To a solution of Compound 8 (90 mg, 208.10 umol, 1 eq) in DCM (1 mL) was added m-CPBA (42.25 mg, 208.10 umol, 85% purity, 1 eq), the mixture was stirred at 20° C. for 1 hr. The reaction mixture was quenched by NaHCO$_3$ (50 mg) and the reaction mixture as filtered, the filtrate was concentrated to give a crude product. The residue was purified by prep-HPLC (column: Phenomenex luna C18 150*25 mm*10 um;mobile phase: [water(FA)-ACN];B %: 30%-60%,9 min), the purified solution was lyophilized to give 009 (16.4 mg, 35.03 umol, 16.83% yield, 95.8% purity) as a white solid. LCMS: Rt=0.391 min, m/z=449.3 (M+H)$^+$ 1H NMR (400 MHz, CHLOROFORM-d) δ=8.40 (s, 1H), 8.22-8.20 (m, 1H), 7.42-7.35 (m, 1H), 7.34-7.28 (m, 2H), 7.24-7.19 (m, 1H), 7.09-7.02 (m, 1H), 6.98-6.94 (m, 1H), 5.11-4.73 (m, 2H), 3.48 (q, J=6.8 Hz, 2H), 2.93 (s, 3H), 2.91-2.88 (m, 3H), 2.11-2.06 (m, 3H), 1.10 (t, J=7.0 Hz, 3H).

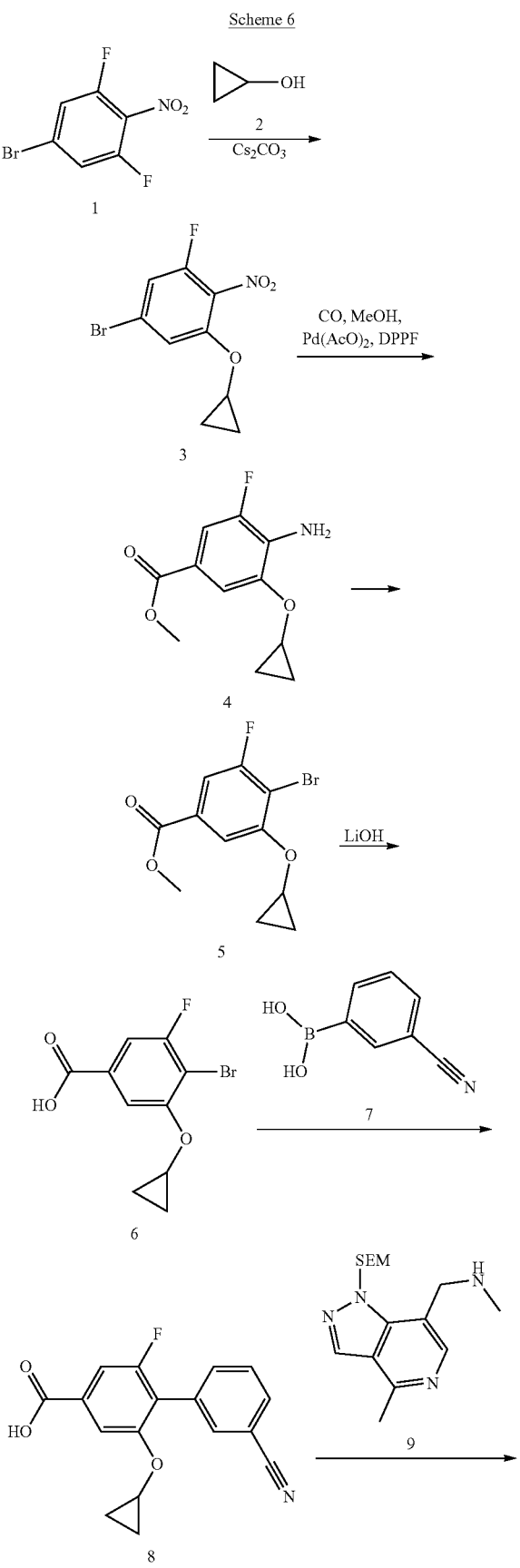

Scheme 6

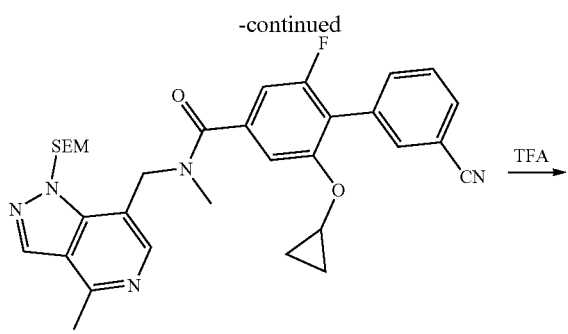

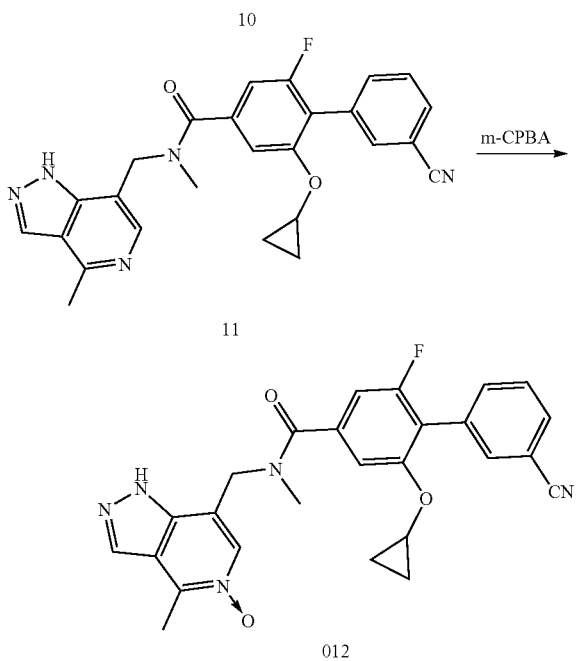

To a solution of compound 1 (6.8 g, 28.57 mmol, 1 eq) and compound 2 (1.66 g, 28.57 mmol, 1 eq) in DMF (120 mL) was added $Cs_2CO_3$ (18.62 g, 57.15 mmol, 2 eq) stirred at 25° C. for 12 hr. TLC (PE:EtOAC=10:1) indicated 20% of compound 1 was remained, and one major new spot with larger polarity was detected. The reaction mixture was poured into $H_2O$ (500 mL), was extracted with EtOAc (300 mL×3). The combined organics were washed with NaCl aq. (500 mL×3), dried with $Na_2SO_4$ and concentrated to give the crude. The residue was purified by column chromatography ($SiO_2$, Petroleum ether/Ethyl acetate=1/0 to 10/1) to give product. Compound 3 (5.42 g, 19.63 mmol, 68.70% yield) was obtained as a yellow oil. 1HNMR (400 MHz, CHLOROFORM-d) δ=7.36-7.33 (m, 1 H), 7.06-7.02 (m, 1H), 3.90-3.84 (m, 1H), 0.89-0.86 (m, 4H)

To a solution of compound 3 (5.4 g, 19.56 mmol, 1 eq) in MeOH (60 mL) was added $Pd(OAc)_2$ (439.16 mg, 1.96 mmol, 0.1 eq), DPPF (2.17 g, 3.91 mmol, 0.2 eq) and TEA (9.90 g, 97.81 mmol, 13.61 mL, 5 eq) stirred at 80° C. for 16 hr under CO (50 psi). The reaction mixture was diluted with $H_2O$ 100 mL and extracted with EtOAc 150 mL (5 mL×3), combined organic layers, dried over $Na_2SO_4$, filtered and concentrated under reduced pressure to give a residue. The residue was purified by column chromatography ($SiO_2$, Petroleum ether/Ethyl acetate=1/0 to 10/1) to give product. Compound 4 (3.43 g, 15.23 mmol, 77.86% yield) was obtained as a light yellow solid. LCMS: Rt=0.457 min, m/z=226.2 $(M+H)^+$ 1H NMR (400 MHz, DMSO-d6) δ=7.54-7.46 (m, 1H), 7.32-7.24 (m, 1H), 5.59-5.47 (m, 2H), 3.98-3.91 (m, 1H), 3.81-3.73 (m, 3H), 0.81-0.69 (m, 4H)

To a solution of compound 4 (3.3 g, 14.65 mmol, 1 eq) in ACN (70 mL) was added CuBr (4.20 g, 29.31 mmol, 892.53 uL, 2 eq) and isoamyl nitrite (3.43 g, 29.31 mmol, 3.95 mL, 2 eq) at 0° C., the mixture was stirred at 20° C. for 1 hr. TLC (PE:EtOAc=10:1) indicated compound 4 was consumed completely and new spots formed. The reaction mixture was poured into $H_2O$ (100 mL), was extracted with EtOAc (100 mL×3). The combined organics were dried with $Na_2SO_4$ and concentrated to give the crude. The residue was purified by column chromatography ($SiO_2$, Petroleum ether/Ethyl acetate=1/0 to 10/1) to give product. Compound 5 (2.72 g, 9.41 mmol, 64.21% yield) was obtained as a white solid. To a solution of compound 5 (2.72 g, 9.41 mmol, 1 eq) in THF (30 mL) and $H_2O$ (10 mL) was added $LiOH·H_2O$ (1.18 g, 28.23 mmol, 3 eq) stirred at 20° C. for 1 hr. The organic solvents were evaporated under vacuum, the resulting mixture was acidified by 1N HCl to pH 4, then the mixture was filtered, and washed by water (10 mL), the filter cake was dried under vacuum to give product. Compound 6 (2.5 g, 9.09 mmol, 96.60% yield) was obtained as a light yellow solid. LCMS: Rt=0.569 min, m/z=272.9 $(M-H)^+$ To a solution of compound 6 (1 g, 3.64 mmol, 1 eq) and compound 7 (801.28 mg, 5.45 mmol, 1.5 eq) in dioxane (10 mL) and $H_2O$ (2 mL) was added $Pd(dppf)Cl_2·CH_2Cl_2$ (148.44 mg, 181.77 umol, 0.05 eq) and $K_2CO_3$ (753.66 mg, 5.45 mmol, 1.5 eq) he mixture was stirred at 100° C. for 12 hr under $N_2$. The reaction mixture was partitioned between EtOAc (50 mL×3) and $H_2O$ (50 mL). The organic phase was separated, dried over $Na_2SO_4$, filtered and concentrated under reduced pressure to give a residue. The residue was purified by prep-HPLC (column: Phenomenex luna C18 250*50 mm*15 um; mobile phase: [water ($NH_4HCO_3$)-ACN]; B %: 17%-47%, 8 min), filtered and concentrated under reduced pressure to give product. Compound 8 (700 mg, 2.35 mmol, 64.77% yield) was obtained as a yellow oil. LCMS: Rt=0.623 min, m/z=296.0 $(M-H)^+$ To a solution of compound 8 (80 mg, 269.11 umol, 1 eq), compound 9 (82.48 mg, 269.11 umol, 1 eq) in DCM (4 mL) was added EDCI (77.38 mg, 403.66 umol, 1.5 eq) and DMAP (16.44 mg, 134.55 umol, 0.5 eq). The mixture was stirred at 20° C. for 1 hr. The reaction mixture was concentrated under vacuum to give a residue. The residue was purified by prep-TLC ($SiO_2$, DCM:MeOH=10:1) to give product. Compound 10 (68 mg, 116.09 umol, 43.14% yield) was obtained as a light yellow oil. LCMS: Rt=0.544 min, m/z=586.5 $(M+H)^+$ To a solution of compound 10 (68 mg, 116.09 umol, 1 eq) in DCM (1 mL) was added TFA (1.54 g, 13.51 mmol, 1 mL, 116.34 eq), the mixture was stirred at 20° C. for 1 hr. The reaction mixture was concentrated under vacuum to give a residue. The residue was purified by prep-TLC ($SiO_2$, DCM:MeOH=10:1) to give product. Compound 11 (29 mg, 63.67 umol, 54.84% yield) was obtained as a colorless oil. LCMS: Rt=0.386 min, m/z=443.2 $(M+H)^+$ To a solution of compound 11 (29 mg, 63.67 umol, 1 eq) in DCM (1 mL) was added m-CPBA (11.21 mg, 63.67 umol, 98% purity, 1 eq), the mixture was stirred at 20° C. for 1 hr. The reaction mixture was quenched by $Na_2SO_3$ (10 mL) and extracted by ethyl acetate (10 mL×3), the combined organic phase was dried and concentrated under vacuum to give a residue. The crude product was purified by prep-HPLC (column: Phenomenex luna C18 150*25 mm*10 um; mobile phase: [water (FA)-ACN];B %: 26%-56%, 9 min), the purified solution was lyophilized to give product. O12 (7.3 mg, 15.48 umol, 24.32% yield, 100% purity) was obtained as a white solid. LCMS: Rt=0.484 min, m/z=472.3 (M+H)+
1H NMR (400 MHz, CHLOROFORM-d) δ=12.44-12.07 (m, 1H), 8.37-8.28 (m, 1H), 8.21-8.13 (m, 1H), 7.68-7.62 (m, 2H), 7.61-7.57 (m, 1H), 7.56-7.50 (m, 1H), 7.26-7.23 (m, 1H), 6.94-6.89 (m, 1H), 4.92-4.86 (m, 2H), 3.79-3.73 (m, 1H), 3.14-3.10 (m, 3H), 2.87 (s, 3H), 0.86-0.78 (m, 2H), 0.74-0.67 (m, 2H).

Compound 038 was prepared in a similar manner to Scheme 6 and was obtained as a white solid (18.2 mg, 39.52 umol, 16.42% yield, 100% purity). LCMS: Rt=0.549 min, m/z=461.0 (M+H+). 1H NMR: (400 MHz, CHLOROFORM-d) δ=12.30 (br s, 1H), 8.22 (br s, 1H), 8.15 (s, 1H), 7.45-7.27 (m, 4H), 7.16-6.98 (m, 2H), 6.90 (s, 1H), 4.85 (br s, 2H), 4.68 (br t, J=6.9 Hz, 1H), 3.07 (s, 3H), 2.84 (br s, 3H), 2.43 (br d, J=5.5 Hz, 2H), 2.23-2.04 (m, 2H), 1.75 (br s, 2H).

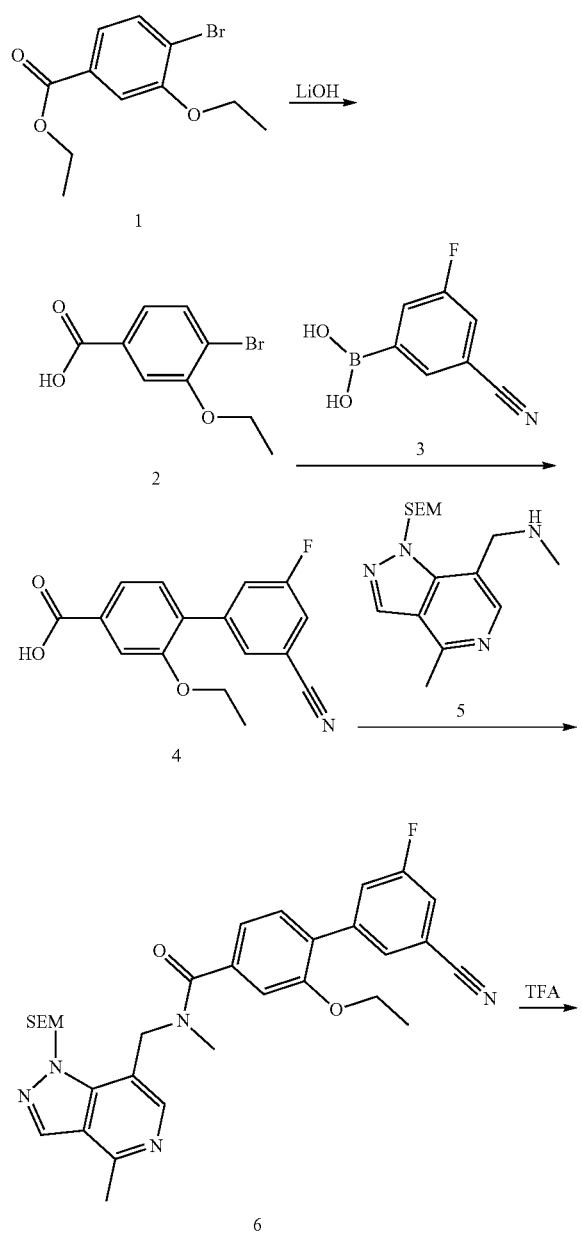

Scheme 7

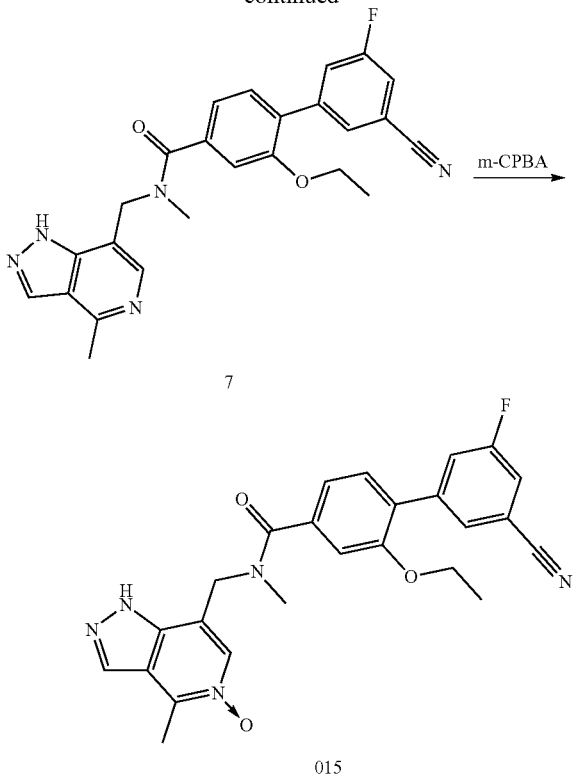

To a solution of Compound 1 in EtOH (6 mL), THF (2 mL) and H2O (2 mL) was added LiOH·H2O (460.93 mg, 10.98 mmol, 3 eq). The mixture was stirred at 20° C. for 1 hr. The reaction mixture was acidified by 1N HCl to pH4 and extracted by EtOAc (15 mL×3), filtered, then concentrated under vacuum to give Compound 2 (490 mg, 2.00 mmol, 54.61% yield) as a white solid which was used in the next step. LCMS: Rt=0.278 min, m/z=245.0 (M−H)+

A mixture of Compound 2 (240 mg, 979.31 umol, 1 eq), Compound 3 (323.04 mg, 1.96 mmol, 2 eq), K2CO3 (270.69 mg, 1.96 mmol, 2 eq), Pd(dppf)Cl2·CH2Cl2 (39.99 mg, 48.97 umol, 0.05 eq) in dioxane (5 mL) and H2O (0.5 mL) then the mixture was stirred at 100° C. for 12 hr under N2 atmosphere. The reaction mixture was poured into water (10 mL) and extracted with EtOAc (10 mL×3). The combined organic layers were over by Na2SO4, filtered and concentrated under reduced pressure to give a residue. The residue was purified by prep-HPLC (column: Welch Xtimate C18 150*25 mm*5 um; mobile phase: [water (NH3H2O)-ACN]; B %: 8%-38%, 8 min), the purified solution was lyophilized to give Compound 4 (90 mg, 309.18 umol, 31.57% yield, 98% purity) as a white solid. LCMS: Rt=0.343 min, m/z=284.1 (M−H)+

To a solution of Compound 4 (60 mg, 210.33 umol, 1 eq) and Compound 5 (96.69 mg, 315.49 umol, 1.5 eq) in DCM (1 mL) was added EDCI (60.48 mg, 315.49 umol, 1.5 eq) and DMAP (2.57 mg, 21.03 umol, 0.1 eq). The mixture was stirred at 20° C. for 12 hr. The reaction mixture was poured into water (5 mL) and extracted by DCM (5 mL×3), the organic phase was dried and concentrated under vacuum to give a residue. The residue was purified by prep-TLC (SiO2, Petroleum ether/Ethyl acetate=0:1), the purified solution was concentrated on vacuum to give Compound 6 (20 mg, 34.86 umol, 16.57% yield) as a colorless oil. LCMS: Rt=0.517 min, m/z=574.3 (M+H)+

To a solution of Compound 6 (20 mg, 34.86 umol, 1 eq) in DCM (1 mL) was added TFA (3.08 g, 27.01 mmol, 2 mL, 774.88 eq). The mixture was stirred at 20° C. for 2 hr. The reaction mixture was concentrated at 20° C. and under reduced pressure to give a residue. The residue was purified by prep-HPLC (column: Phenomenex luna C18 150*25 mm*10 um; mobile phase: [water(FA)-ACN];B %: 17%-47%,9 min), the purified solution was lyophilized to give Compound 7 (10 mg, 22.55 umol, 64.69% yield) as a white solid. LCMS: Rt=0.440 min, m/z=444.2 (M+H)$^+$ To a solution of Compound 7 (10 mg, 22.55 umol, 1 eq) in DCM (2 mL) was added m-CPBA (11.91 mg, 67.65 umol, 98% purity, 3 eq) slowly under 0° C. The mixture was stirred at 20° C. for 1 hr. The reaction mixture was filtered and the cake was dissolved in saturated $Na_2SO_3$ solution (5 mL) slowly, the filtrate was concentrated to give a residue. The residue was purified by prep-HPLC (column: Phenomenex luna C18 150*25 mm*10 um; mobile phase: [water (FA)-ACN]; B %: 27%-57%, 9 min), the purified solution was lyophilized to give 015 (2.3 mg, 5.01 umol, 22.20% yield, 100% purity) as a white solid. LCMS: Rt=0.373 min, m/z=460.2 (M+H)$^+$ 1H NMR (400 MHz, CHLOROFORM-d) δ=12.49-12.32 (m, 1H), 8.41-8.34 (m, 1H), 8.24-8.19 (m, 1H), 7.67-7.63 (m, 1H), 7.54 (dd, J=1.6, 9.6 Hz, 1H), 7.38-7.32 (m, 2H), 7.14-7.06 (m, 2H), 4.95-4.85 (m, 2H), 4.10 (q, J=6.9 Hz, 2H), 3.14-3.06 (m, 3H), 2.94-2.86 (m, 3H), 1.39 (t, J=6.9 Hz, 3H).

Compound 016 was prepared in a similar manner to Scheme 7 (11.8 mg, 25.41 umol, 16.28% yield, 100% purity) and was obtained as a white solid. LCMS: Rt=0.438 min, m/z=465.2 (M+H)$^+$ 1H NMR (400 MHz, CHLOROFORM-d) δppm 8.39-8.44 (m, 1 H) 8.23 (s, 1 H) 7.45 (d, J=1.38 Hz, 1 H) 7.33 (d, J=7.75 Hz, 1 H) 7.11 (dd, J=7.88, 1.50 Hz, 1 H) 6.97-7.04 (m, 2 H) 6.75-6.84 (m, 1 H) 4.91 (s, 2 H) 3.75-3.81 (m, 1 H) 3.12 (s, 3 H) 2.90 (s, 3 H) 0.81-0.87 (m, 2 H) 0.74-0.80 (m, 2 H).

Compound 045 was prepared in a similar manner to Scheme 7 using HCl/dioxane instead of TFA/DCM. Compound 045 was isolated as a white solid (3 mg, 6.30 umol, 18.93% yield, 98.029% purity). LCMS: Rt=0.449 min, m/z=467.2 (M+H)$^+$ 1H NMR: (400 MHz, CHLOROFORM-d) δ=12.69-12.54 (m, 1H), 9.85-9.68 (m, 1H), 8.15-8.11 (m, 2H), 7.88 (s, 1H), 7.61 (br d, J=8.6 Hz, 1H), 7.36-7.32 (m, 3H), 7.23 (br s, 1H), 4.82 (br d, J=6.1 Hz, 2H), 3.88 (dt, J=2.8, 6.0 Hz, 1H), 2.78 (s, 3H), 0.87-0.81 (m, 2H), 0.74-0.69 (m, 2H).

Scheme 8

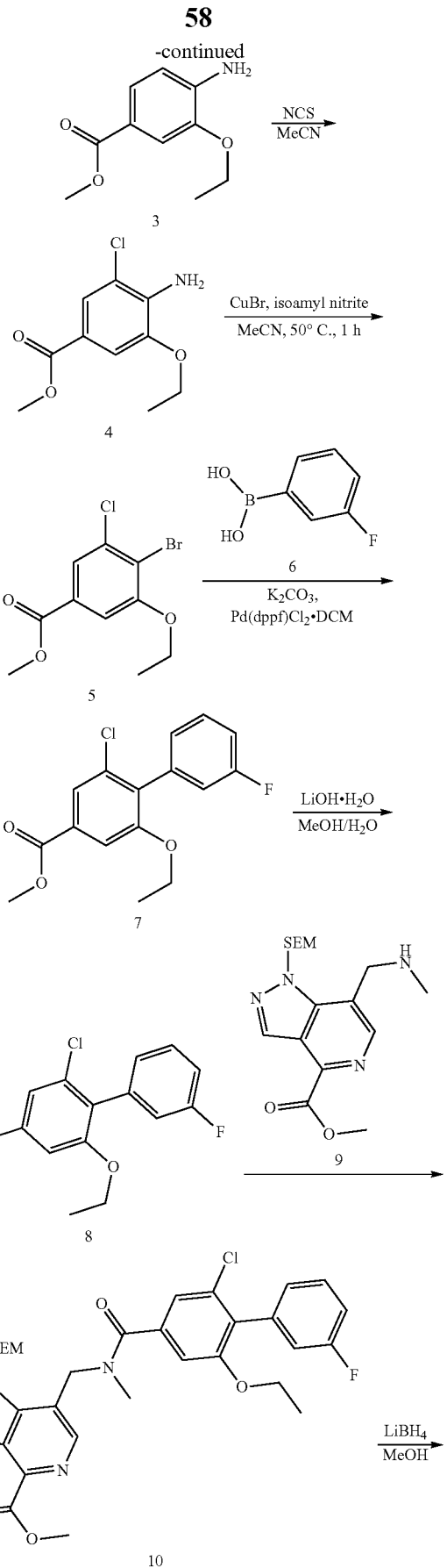

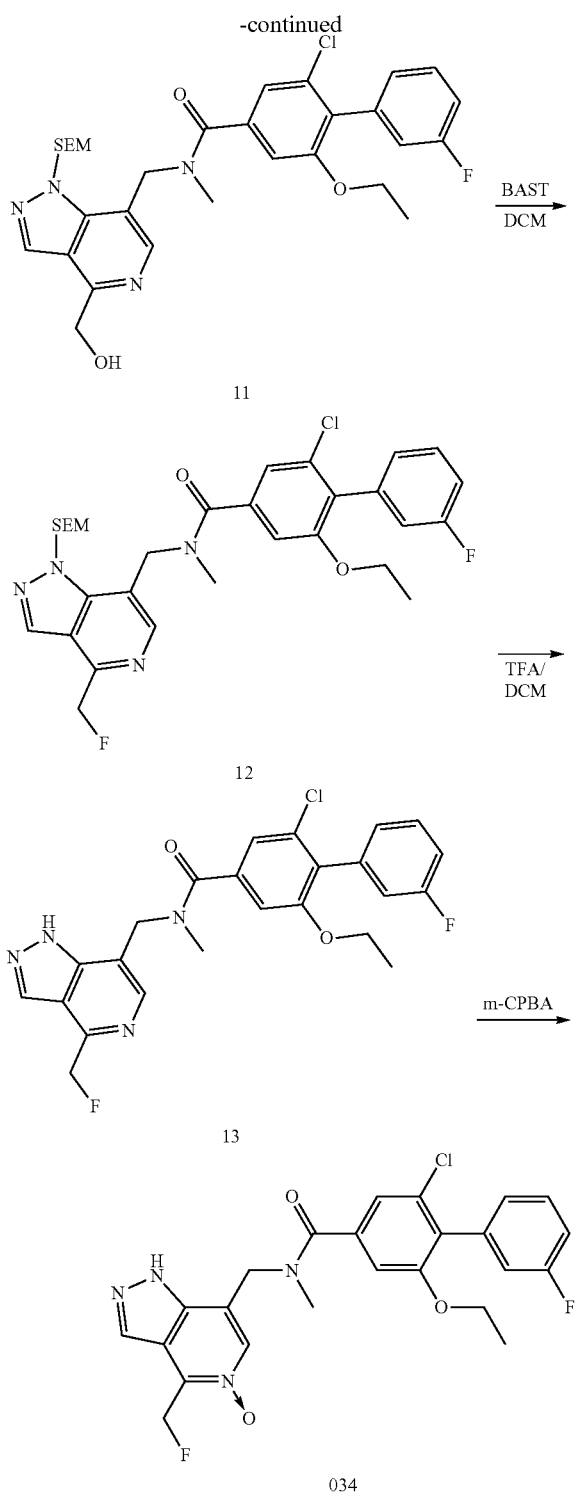

To a solution of Compound 1 (10 g, 45.46 mmol, 1 eq) in THF (100 mL) in 250 mL 3-necked round-bottom flask was added EtOH (4.19 g, 90.91 mmol, 2 eq) and KOH (7.65 g, 136.37 mmol, 3 eq). The reaction mixture was stirred at 30° C. for 12 h. TLC (Petroleum ether:Ethyl acetate=10/1) indicated Compound 1 was consumed completely and one new spot formed. The reaction mixture was poured into water (200 mL) and extracted by ethyl acetate (200 mL×3), the combined organic phase was dried and concentrated under vacuum to give a residue. The residue was purified by column chromatography (SiO$_2$, Petroleum ether/Ethyl acetate=10/1), the purified solution was concentrated under vacuum to give Compound 2 (9 g, 36.58 mmol, 80.47% yield) as an orange oil.

To a solution of Compound 2 (9 g, 36.58 mmol, 1 eq) in MeOH (100 mL) in glass bottle (1 L) was added Pd(OAc)$_2$ (821.18 mg, 3.66 mmol, 0.1 eq), DPPF (4.06 g, 7.32 mmol, 0.2 eq) and TEA (11.10 g, 109.73 mmol, 15.27 mL, 3 eq) stirred at 80° C. for 12 hr under CO(50 psi). The reaction mixture was filtered and concentrated under vacuum to give a residue. The residue was purified by column chromatography (SiO$_2$, Petroleum ether/Ethyl acetate=10/1 to 5/1), the purified solution was concentrated under vacuum to give Compound 3 (3.1 g, 15.88 mmol, 43.42% yield) as an orange oil. LCMS: Rt=0.366 min, m/z=196.2 (M+H)$^+$ 1H NMR (400 MHz, DMSO-d6) δ=7.37 (dd, J=1.7, 8.2 Hz, 1H), 7.29-7.25 (m, 1H), 6.64 (d, J=8.3 Hz, 1H), 5.58 (s, 2H), 4.06-4.02 (m, 2H), 3.76-3.71 (m, 3H), 1.35 (t, J=6.9 Hz, 3H)

To a solution of Compound 3 (500 mg, 2.56 mmol, 1 eq) in MeCN (5 mL) in 100 mL round-bottom flask was added NCS (342.02 mg, 2.56 mmol, 1 eq), the mixture was stirred at 20° C. for 12 hr. The mixture was stirred at 50° C. for 1 hr. The reaction mixture was poured into water (20 mL) and extracted by ethyl acetate (20 mL×3), the combined organic phase was dried and concentrated under vacuum to give a crude product. The residue was purified by column chromatography (SiO$_2$, Petroleum ether/Ethyl acetate=5/1), the purified solution was concentrated under vacuum to give Compound 4 (540 mg, 2.35 mmol, 91.80% yield) as a black brown oil. LCMS: Rt=0.396 min, m/z=230.1 (M+H)$^+$ 1H NMR (400 MHz, CHLOROFORM-d) δ=7.65 (d, J=1.3 Hz, 1H), 7.35 (d, J=1.3 Hz, 1H), 4.61 (br s, 2H), 4.14 (q, J=7.0 Hz, 2H), 3.87 (s, 3H), 1.46 (t, J=7.0 Hz, 3H)

To a solution of Compound 4 (710 mg, 3.09 mmol, 1 eq) and CuBr (886.96 mg, 6.18 mmol, 188.31 uL, 2 eq) in ACN (8 mL) in 50 mL round-bottom flask was added isoamyl nitrite (724.32 mg, 6.18 mmol, 832.55 uL, 2 eq), the mixture was stirred at 50° C. for 1 hr. TLC (Petroleum ether:Ethyl acetate=5:1) indicated many new spots formed. The reaction was messy according to TLC (Petroleum ether:Ethyl acetate=5:1). The reaction mixture was diluted with H$_2$O 20 mL and extracted with EtOAc 60 mL (20 mL×3). The combined organic layers were dried over Na$_2$SO$_4$, filtered and concentrated under reduced pressure to give a residue. The residue was purified by column chromatography (SiO$_2$, Petroleum ether/Ethyl acetate=5/1), the purified solution was concentrated under vacuum to give Compound 5 (540 mg, 1.84 mmol, 59.50% yield) as a yellow oil. 1H NMR (400 MHz, DMSO-d6) δ=7.69-7.64 (m, 1H), 7.47-7.43 (m, 1H), 4.22 (q, J=6.9 Hz, 2H), 3.87 (s, 3H), 1.41-1.36 (m, 3H)

To a solution of Compound 5 (360 mg, 1.23 mmol, 1 eq) in dioxane (4 mL) in glass bottle (40 mL) was added Compound 6 (257.40 mg, 1.84 mmol, 1.5 eq), K$_2$CO$_3$ (338.99 mg, 2.45 mmol, 2 eq) and Pd(dppf)Cl$_2$·CH$_2$Cl$_2$ (50.08 mg, 61.32 umol, 0.05 eq), then the mixture was stirred at 100° C. for 12 hr under N$_2$. The reaction mixture as filtered, the reaction mixture was poured into water (20 mL) and extracted by ethyl acetate (20 mL×3), the combined organic phase was dried and concentrated under vacuum to give a residue. The residue was purified by column chromatography (SiO$_2$, Petroleum ether/Ethyl acetate=5/1), the purified solution was concentrated under vacuum to give Compound 7 (300 mg, 971.72 umol, 79.23% yield) as an off-white oil. 1H NMR (400 MHz, CHLOROFORM-d) δ=7.77 (d, J=1.5 Hz, 1H), 7.52 (d, J=1.5 Hz, 1H), 7.43-7.37

(m, 1H), 7.09-7.07 (m, 1H), 7.07-7.05 (m, 1H), 7.04-6.99 (m, 1H), 4.06 (q, J=6.9 Hz, 2H), 3.96 (s, 3H), 1.27-1.24 (m, 3H)

The mixture of Compound 7 (300 mg, 971.72 umol, 1 eq) in MeOH (4 mL) in 100 mL round-bottom flask was added LiOH·H$_2$O (122.33 mg, 2.92 mmol, 3 eq) and H$_2$O (1 mL) then the mixture solution was stirred at 20° C. for 1 hr. The organic solvents was evaporated under vacuum, the resulting mixture was acidified by 1N HCl to pH 4, then the mixture was filtered, and washed by water (10 mL), the filter cake was dried under vacuum to give Compound 8 (280 mg, 950.10 umol, 97.78% yield) as a light-yellow solid which was used directly in the next step. LCMS: Rt=0.441 min, m/z=293.0 (M+H)$^+$ To a solution of Compound 8 (280 mg, 950.10 umol, 1 eq) in DCM (3 mL) in 100 mL round-bottom flask was added EDCI (273.20 mg, 1.43 mmol, 1.5 eq), DMAP (11.61 mg, 95.01 umol, 0.1 eq) and Compound 9 333.00 mg, 950.10 umol, 1 eq). The mixture was stirred at 20° C. for 1 hr. The reaction mixture was concentrated on vacuum to give residue. The residue was purified by column chromatography (SiO$_2$, Petroleum ether/Ethyl acetate=0/1), the purified solution was concentrated under vacuum to give Compound 10 (380 mg, 605.89 umol, 63.77% yield) as a yellow oil. LCMS: Rt=0.612 min, m/z=627.5 (M+H)$^+$ To a 100 mL round-bottom flask solution of Compound 10 380 mg, 605.89 umol, 1 eq) in MeOH (5 mL) was added LiBH4 (65.99 mg, 3.03 mmol, 5 eq) under 0° C. slowly. The mixture was stirred at 20° C. for 1 hr. The reaction mixture was poured into saturated NH$_4$Cl aqueous (20 mL) and extracted by extracted by ethyl acetate (20 mL×3), the combined organic phase was dried and concentrated under vacuum to give a residue. The residue was purified by column chromatography (SiO$_2$, Petroleum ether/Ethyl acetate=0/1 and Dichloromethane:Methanol=10/1), the purified solution was concentrated under vacuum to give Compound 11 (260 mg, 433.94 umol, 71.62% yield) was obtained as a yellow oil. LCMS: Rt=0.463 min, m/z=599.6 (M+H)$^+$ To a solution of Compound 11 (260 mg, 433.94 umol, 1 eq) in DCM (10 mL) in 100 mL round-bottom flask was added BAST (192.01 mg, 867.87 umol, 190.11 uL, 2 eq) slowly at 0° C. under N$_2$, the mixture was stirred at 0° C. for 30 min under N$_2$. The reaction mixture was poured into saturated NaHCO$_3$ aqueous (20 mL) and extracted by DCM (20 mL×3), the combined organic phase was dried and concentrated under vacuum to give a residue. The residue was purified by prep-TLC (SiO$_2$, Petroleum ether/Ethyl acetate=0/1),the purified solution was concentrated under vacuum to give Compound 12 (75 mg, 124.76 umol, 28.75% yield) as a yellow oil. LCMS: Rt=0.554 min, m/z=601.5 (M+H)$^+$ To a solution of Compound 12 (75 mg, 124.76 umol, 1 eq) in round-bottom(ed) flask (100 mL) was added TFA (1.23 g, 10.80 mmol, 0.8 mL, 86.61 eq) and DCM (0.4 mL), then the mixture was stirred at 20° C. for 1 hr. The reaction mixture was basified by saturated NaHCO$_3$ aqueous (10 mL), then the reaction mixture was diluted with H$_2$O (10 mL) and extracted with EtOAc (10 mL×3). The combined organic layers were washed with brine, dried over Na$_2$SO$_4$, filtered and concentrated under reduced pressure to give a residue. The residue was purified by prep-HPLC (column: Phenomenex luna C18 150*25 mm*10 um; mobile phase: [water (FA)-ACN];B %: 43%-73%,9 min), the purified solution was lyophilized to give Compound 13 (15 mg, 31.85 umol, 25.53% yield) as a yellow solid. LCMS: Rt=0.412 min, m/z=471.3 (M+H)$^+$ To a solution of Compound 13 (15 mg, 31.85 umol, 1 eq) in DCM (1 mL) in round-bottom flask (100 mL) was added m-CPBA (19.40 mg, 95.56 umol, 85% purity, 3 eq) the mixture was stirred at 20° C. for 1 hr. After the reaction was completed, the mixture was filtered and the cake was dissolved in saturated Na$_2$SO$_3$ solution (10 mL) slowly, the filtrate was concentrated to give a crude product. The residue was purified by prep-HPLC (column: Waters xbridge 150*25 mm 10 um;mobile phase: [water(NH$_4$HCO$_3$)-ACN];B %: 30%-60%,8 min), the purified solution was lyophilized to give Compound 034 (10.4 mg, 21.25 umol, 66.72% yield, 99.5% purity) as a white solid. LCMS: Rt=0.435 min, m/z=487.3(M+H)$^+$1H NMR (400 MHz, CHLOROFORM-d) δ=12.41-12.24 (m, 1H), 8.39 (d, J=3.5 Hz, 1H), 8.14 (s, 1H), 7.44-7.35 (m, 1H), 7.16 (s, 1H), 7.12-7.08 (m, 1H), 7.05 (br d, J=7.9 Hz, 1H), 6.99 (br d, J=9.6 Hz, 1H), 6.95-6.92 (m, 1H), 6.12-5.95 (m, 2H), 4.93-4.84 (m, 2H), 4.00 (q, J=6.9 Hz, 2H), 3.10 (5, 3H), 1.25 (t, J=6.9 Hz, 3H).

Compound 036 was prepared in a similar manner to Scheme 8 and was isolated as a white solid (7 mg, 13.40 umol, 12.98% yield, 95.8% purity). LCMS: Rt=0.517 min, m/z=501.2 (M+H$^+$) $^1$H NMR: (400 MHz, CHLOROFORM-d) δ=8.40 (d, J=3.6 Hz, 1H), 8.17-8.14 (m, 1H), 7.21-7.13 (m, 2H), 7.06-6.99 (m, 2H), 6.89-6.80 (m, 1H), 6.10 (s, 1H), 6.00-5.96 (m, 1H), 4.92 (5, 2H), 3.96-3.90 (m, 1H), 3.03 (d, J=1.5 Hz, 3H), 0.60-0.54 (m, 2H), 0.50-0.43 (m, 2H).

Compound 047 was prepared in a similar manner to Scheme 8 and was obtained as a brown solid (9.3 mg, 19.04 umol, 59.97% yield, 100% purity). LCMS: Rt=0.450 min, m/z=489.2 (M+H)$^+$$^1$H NMR (400 MHz, CHLOROFORM-d) δ=11.94-12.47 (m, 1 H) 8.38 (br s, 1 H) 8.15 (br s, 1 H) 7.13-7.22 (m, 2 H) 7.08 (br d, J=7.13 Hz, 2 H) 6.85 (br t, J=8.76 Hz, 1 H) 5.92-6.14 (m, 2 H) 4.92 (br s, 2 H) 3.87-3.97 (m, 2 H) 3.01 (s, 3 H) 1.20 (br t, J=6.94 Hz, 3 H).

Compound 048 was prepared in a similar manner to Scheme 8 using DAST and was obtained as a yellow solid (5.6 mg, 11.44 umol, 29.66% yield, 98.6% purity). LCMS: Rt=0.541 min, m/z=483.2 (M+H$^+$) $^1$H NMR (400 MHz, CHLOROFORM-d) δ=12.68-12.07 (m, 1H), 8.39 (d, J=3.6 Hz, 1H), 8.14 (s, 1H), 7.45 (d, J=1.4 Hz, 1H), 7.34 (d, J=7.8 Hz, 1H), 7.12 (dd, J=1.4, 7.8 Hz, 1H), 7.03-6.97 (m, 2H), 6.80 (tt, J=2.3, 8.9 Hz, 1H), 6.12-5.95 (m, 2H), 4.90 (s, 2H), 3.82-3.75 (m, 1H), 3.10 (s, 3H), 0.87-0.82 (m, 2H), 0.80-0.74 (m, 2H).

Compound 049 was prepared in a similar manner to Scheme 8 and was obtained as a white solid (3 mg, 6.69 umol, 19.26% yield, 99.342% purity). LCMS: Rt=0.447 min, m/z=446.3 (M+H)$^+$$^1$H NMR (400 MHz, CHLOROFORM-d) δ=8.23 (s, 1H), 8.18 (s, 1H), 7.40-7.37 (m, 2H), 7.33-7.29 (m, 2H), 7.11-7.05 (m, 3H), 4.90 (s, 2H), 4.08 (q, J=7.0 Hz, 2H), 3.12 (s, 3H), 1.39 (t, J=7.0 Hz, 3H).

Compound 050 was prepared in a similar manner to Scheme 8 and was obtained as a white solid (3.0 mg, 6.09 umol, 10.53% yield, 98% purity). LCMS: Rt=0.529 min, m/z=483.1 (M+H$^+$). 1H NMR (400 MHz, CHLOROFORM-d) δ=12.24-12.50 (1H, m), 8.50 (1H, d, J=3.3 Hz), 8.32 (1H, s), 7.40 (1H, dt, J=6.1 and 7.9 Hz), 7.07-7.25 (5H, m), 6.03-6.19 (2H, m), 4.96 (2H, s), 3.89 (1H, dt, J=2.9 and 6.0 Hz), 3.06 (3H, d, J=1.0 Hz), 0.51-0.57 (2H, m), 0.39-0.46 (2H, m).

Compound 052 was prepared in a similar manner to Scheme 8 using DAST and was obtained as a white solid (5.25 mg, 10.57 umol, 20.80% yield, 98.3% purity). LCMS: Rt=0.506 min, m/z=489.3 (M+Na$^+$) $^1$H NMR (400 MHz, CHLOROFORM-d) δ=12.39-12.20 (m, 1H), 8.42-8.38 (m, 1H), 8.15-8.12 (m, 1H), 6.99-6.92 (m, 2H), 6.89-6.81 (m, 3H), 6.09 (s, 1H), 5.98 (s, 1H), 4.88 (s, 2H), 4.11-4.01 (m, 2H), 3.08 (s, 3H), 1.34 (t, J=6.9 Hz, 3H).

Compound 053 was prepared in a similar manner to Scheme 8 and was obtained as a white solid (15 mg, 31.88 umol, 48.30% yield, 100% purity). LCMS: Rt=0.447 min, m/z=446.3 (M+H)⁺ 1H NMR: (400 MHz, CHLOROFORM-d) δ=12.49-12.10 (m, 1H), 8.41 (d, J=3.6 Hz, 1H), 8.22 (s, 1H), 7.44-7.37 (m, 1H), 7.33-7.27 (m, 2H), 7.23-7.18 (m, 1H), 7.16-7.05 (m, 2H), 6.11 (s, 1H), 5.99 (s, 1H), 4.94 (s, 2H), 3.88 (q, J=7.0 Hz, 2H), 3.03 (d, J=1.4 Hz, 3H), 1.18 (t, J=7.1 Hz, 3H).

Scheme 9

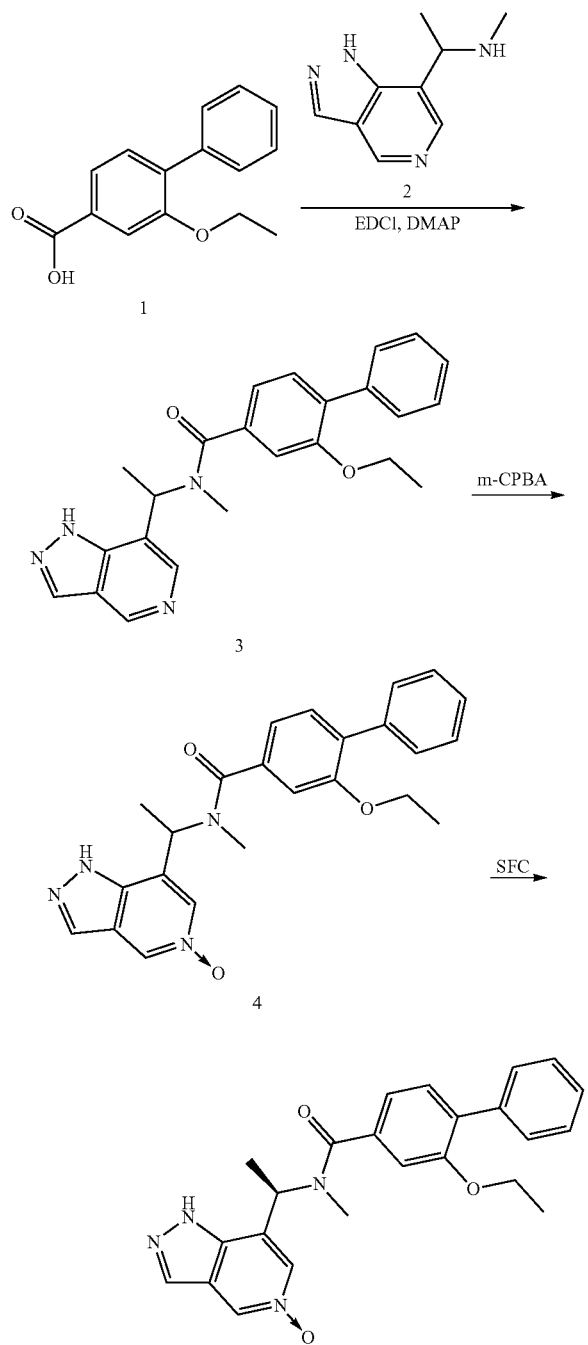

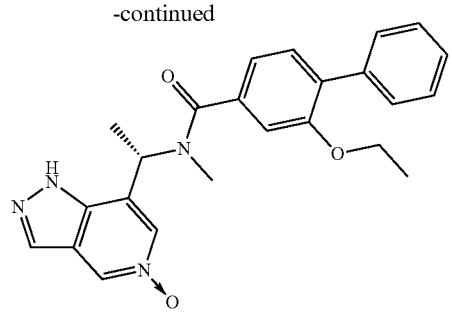

Dissolved Compound 1 (100 mg, 412.76 umol, 1 eq) in DCM (2 mL) in an 8 mL bottle, was added EDCI (118.69 mg, 619.15 umol, 1.5 eq), DMAP (5.04 mg, 41.28 umol, 0.1 eq) and Compound 2 (72.74 mg, 412.76 umol, 1 eq), the reaction mixture was stirred at 20° C. for 1.5 hr by magnetic stirring apparatus. After the reaction was completed, the mixture was concentrated on a rotary evaporator to give a crude product. The crude product was purified by prep-HPLC (column: Phenomenex luna C18 150*25 mm*10 um; mobile phase: [water (FA)-ACN]; B %: 19%-49%, 10 min), After prep-HPLC purification, the eluent was concentrated to remove organic solvents. The residual aqueous solution was lyophilized to give white solid. Compound 3 (85 mg, 212.25 umol, 42.85% yield) was obtained as white solid. LCMS: Rt=0.360 min, m/z=401.8 (M+H⁺).

To a solution of Compound 3 (85 mg, 212.25 umol, 1 eq) in DCM (2 mL) in a 100 mL single-necked round bottom flask was added m-CPBA (129.27 mg, 636.75 umol, 85% purity, 3 eq) slowly at 0° C., the mixture was stirred at 20° C. by magnetic stirrer for 1 hr. After the reaction was completed, the reaction mixture was quenched by Na₂SO₃ (10 mL) and extracted by ethyl acetate (10 mL×3), the combined organic phase was dried and concentrated under vacuum to give a residue. The crude product was purified by prep-HPLC (column: Phenomenex C18 150*25 mm*10 um; mobile phase: [water (NH₄HCO₃)-ACN]; B %: 22%-52%, 8 min). After prep-HPLC purification, the eluent was concentrated to remove organic solvents. The residual aqueous solution was lyophilized to give brown solid. The residual aqueous solution was lyophilized to give white solid. Compound 4 (55 mg, 130.74 umol, 61.60% yield, 99% purity) was obtained as brown solid. LCMS: Rt=0.465 min, m/z=417.3 (M+H⁺)

Compound 4 (55 mg, 132.06 umol, 1 eq) was purified by SFC to give 039 (23.1 mg, 54.91 umol, 41.58% yield, 99% purity) and 040 (24.9 mg, 59.19 umol, 44.82% yield, 99% purity). The product was purified by SFC (column: DAICEL CHIRALCEL OD (250 mm*50 mm, 10 um); mobile phase: [0.1% NH₃H₂O MEOH]; B %: 40%-40%, A6.2; 30 min). After SFC, the eluent was concentrated to remove organic solvents. The residual aqueous solution was lyophilized to give brown solid. 039 (23.1 mg, 54.91 umol, 41.58% yield, 99% purity) was obtained as brown solid. 040 (24.9 mg, 59.19 umol, 44.82% yield, 99% purity) was obtained as brown solid. LCMS of 039: Rt=0.483 min, m/z=417.3 (M+H⁺). ¹H NMR of 039: (400 MHz, CHLOROFORM-d) δ=12.48-12.26 (m, 1H), 8.75 (d, J=1.1 Hz, 1H), 8.23 (s, 1H), 8.16 (s, 1H), 7.59-7.52 (m, 2H), 7.44 (s, 2H), 7.40-7.34 (m, 2H), 7.12-7.07 (m, 2H), 6.44 (br d, J=7.0 Hz, 1H), 4.14-4.02 (m, 2H), 2.89 (s, 3H), 1.83 (d, J=7.1 Hz, 3H), 1.38 (t, J=6.9 Hz, 3H). LCMS of 040: Rt=0.484 min, m/z=417.3 (M+H⁺). ¹H NMR of 040: (400 MHz, CHLOROFORM-d) δ=12.53-12.29 (m, 1H), 8.78 (s, 1H), 8.32-8.12 (m, 2H), 7.56 (d, J=7.3 Hz, 2H), 7.46-7.35 (m, 4H), 7.13-7.07 (m, 2H), 6.51-6.40 (m, 1H), 4.08 (br dd, J=7.1, 14.9 Hz, 2H), 2.89 (s, 3H), 1.84 (d, J=7.1 Hz, 3H), 1.38 (t, J=6.9 Hz, 3H).

Compound 041 and Compound 042 were prepared in a similar manner to the compounds in Scheme 9. Compound 041 was isolated as a brown solid (34.1 mg, 74.61 umol, 42.20% yield, 99% purity). LCMS: Rt=0.512 min, m/z=453.2 (M+H⁺). ¹H NMR: (400 MHz, CHLOROFORM-d) δ=12.33-12.21 (m, 1H), 8.74-8.61 (m, 1H), 8.20-8.04 (m, 2H), 7.27 (d, J=7.6 Hz, 1H), 7.06-6.94 (m, 4H), 6.78-6.68 (m, 1H), 6.34 (br d, J=7.0 Hz, 1H), 4.09-3.93 (m, 2H), 2.78 (s, 3H), 1.74 (d, J=7.3 Hz, 3H), 1.32 (t, J=6.9 Hz, 3H). Compound 042 was isolated as a brown solid (35.7 mg, 78.11 umol, 44.18% yield, 99% purity). LCMS: Rt=0.507 min, m/z=453.2 (M+H⁺). ¹H NMR: (400 MHz, CHLOROFORM-d) δ=12.40-12.20 (m, 1H), 8.69 (br s, 1H), 8.22-8.05 (m, 2H), 7.27 (d, J=7.6 Hz, 1H), 7.05-6.95 (m, 4H), 6.79-6.67 (m, 1H), 6.34 (br d, J=6.9 Hz, 1H), 4.10-3.92 (m, 2H), 2.78 (s, 3H), 1.75 (d, J=7.1 Hz, 4H), 1.32 (t, J=6.9 Hz, 4H).

Compound 043 and Compound 044 were prepared in a similar manner to the compounds in Scheme 9. Compound 043 was isolated as a white solid (6.4 mg, 14.05 umol, 25.34% yield, 99% purity). LCMS: Rt=0.524 min, m/z=451.4 (M+H+). 1H NMR (CHLOROFORM-d): δ8.74 (1H, s), 8.11-8.25 (2H, m), 7.54 (1 H, s), 7.40-7.44 (1H, m), 7.32-7.37 (3H, m), 7.04-7.10 (2H, m), 6.36-6.47 (1H, m), 4.00-4.16 (2H, m), 2.86 (3H, s), 1.82 (3H, d, J=7.1 Hz), 1.38 (3H, t, J=6.9 Hz). Compound 044 was isolated as a white solid (5.2 mg, 11.07 umol, 19.97% yield, 96% purity). LCMS: Rt=0.522 min, m/z=451.2 (M+H+). 1H NMR (CHLOROFORM-d): δ12.35 (1H, br s), 8.74 (1H, d, J=1.1 Hz), 8.12-8.26 (2H, m), 7.54 (1H, s), 7.40-7.44 (1H, m), 7.32-7.38 (3H, m), 7.04-7.11 (2H, m), 6.42 (1H, q, J=7.0 Hz), 3.97-4.16 (2H, m), 2.86 (3H, s), 1.82 (3H, d, J=7.1 Hz), 1.38 (3H, t, J=6.9 Hz m), 6.39-6.62 (1H, m), 3.78 (1H, br d, J=3.0 Hz), 2.84 (3H, s), 1.90 (3H, br d, J=7.1 Hz), 0.80-0.88 (4H, m).

Scheme 10

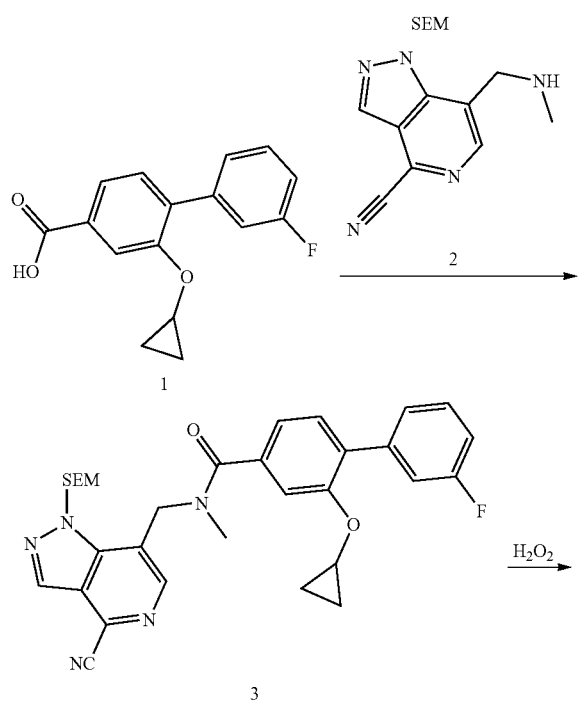

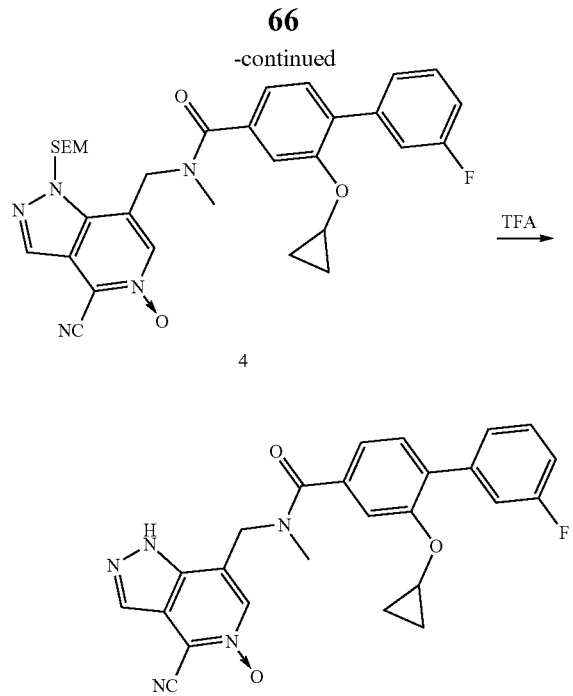

To a solution of Compound 1 (400 mg, 1.26 mmol, 1 eq) and Compound 2 (343.06 mg, 1.26 mmol, 1 eq) in DCM (10 mL) in glass bottle (40 mL) was added EDCI (362.32 mg, 1.89 mmol, 1.5 eq) and DMAP (15.39 mg, 126.00 umol, 0.1 eq). The mixture was stirred at 20° C. for 2 hr. The reaction mixture was concentrated on vacuum to give residue. The crude product was purified by prep-HPLC (column: Phenomenex luna C18 150*25 mm*10 um; mobile phase: [water (FA)-ACN]; B %: 67%-97%, 10 min), the purified solution was concentrated under vacuum to give a Compound 3 (100 mg, 174.91 umol, 13.88% yield) as a white solid. LCMS: Rt=0.589 min, m/z=572.3 (M+H)⁺

To a solution of Compound 3 (60 mg, 104.95 umol, 1 eq) in AcOH (1 mL) in glass bottle (8 mL) was added H₂O₂ (23.80 mg, 209.89 umol, 20.17 uL, 30% purity, 2 eq).The mixture was stirred at 100° C. for 12 hr. The reaction mixture was poured into saturated Na₂SO₃ aqueous (2 mL) and extracted by dichloromethane (2 mL×3), the combined organic phase was dried and concentrated under vacuum to give a residue. The residue purified by prep-TLC (Petroleum ether:Ethyl acetate=1:2), the purified solution was concerned under vacuum to give Compound 4 (45 mg, 76.57 umol, 72.96% yield) as a yellow oil. LCMS: Rt=0.555 min, m/z=588.3 (M+H)⁺

To a solution of Compound 4 (50 mg, 85.08 umol, 1 eq), TFA (1 mL) and DCM (1 mL) DCM (1 mL) in round-bottom flask (100 mL) was stirred at 20° C. for 2 hr. The reaction mixture was concentrated on vacuum to give residue. The residue was purified by Prep-HPLC (column: Phenomenex luna C18 150*25 mm*10 um;mobile phase: [water(FA)-ACN];B %: 39%-69%,9 min), the purified solution was lyophilized to give 051 (1 mg, 2.19 umol, 2.57% yield, 100% purity) as a white solid. LCMS: Rt=0.457 min, m/z=458.2 (M+H)⁺1H NMR: (400 MHz, CHLOROFORM-d) δ=8.23 (s, 1H), 8.19 (s, 1H), 7.45 (s, 1H), 7.39-7.34 (m, 2H), 7.24-7.18 (m, 2H), 7.14-7.10 (m, 1H), 7.08-7.02 (m, 1H), 4.92 (s, 2H), 3.82-3.75 (m, 1H), 3.14 (s, 3H), 0.83 (br t, J=5.5 Hz, 2H), 0.80-0.75 (m, 2H).

Scheme 11

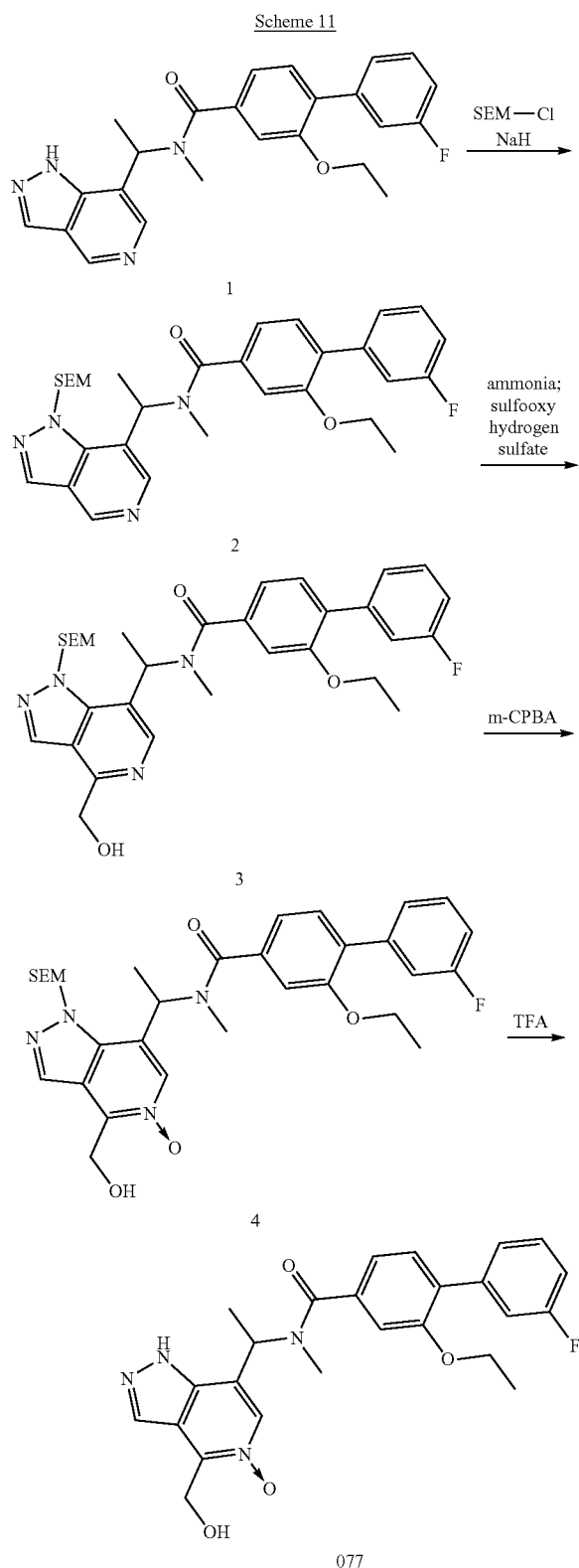

20° C. for 1 h. The mixture was poured into saturated NH₄Cl (50 mL) solution, and extracted with EtOAc (50 mL×3), the combined organic phase was washed with brine (50 mL), dried over anhydrous Na₂SO₄, and concentrated to give a crude product. The crude product was purified by column chromatography (SiO2, Petroleum ether/Ethyl acetate=0/1 to 1/1). Compound 2 (45 mg, 82.01 umol, 11.44% yield) as a colorless oil. LCMS: Rt=0.451 min, m/z=549.2 (M+H⁺)

To a solution of compound 2 (45 mg, 82.01 umol) in MeOH (1 mL) and H₂O (0.1 mL) in a 8 mL glass bottle was added ammonia; sulfooxy hydrogen sulfate (61.76 mg, 270.63 umol, 58.82 uL), the mixture was stirred at 60° C. for 1.5 h. The reaction mixture was concentrated under vacuum to give residue. The residue was purified by prep-TLC (SiO2, DCM:MeOH=10:1). Compound 3 (18 mg, 31.10 umol, 37.92% yield) as a colorless oil. LCMS: Rt=0.445 min, m/z=579.2 (M+H⁺)

To a solution of compound 3 (18.00 mg, 31.10 umol) in DCM (1 mL) was added m-CPBA (12.63 mg, 62.20 umol, 85% purity) at 25° C., the mixture was stirred at 25° C. for 2 hr.

The mixture was poured into sat.Na₂SO₃ aq. (20 mL) and stirred for 0.25 h. Then extracted with EtOAc (20 mL×3). The combined organic layers were dried over Na₂SO₄, filtered and concentrated to give the crude product. The crude product was purified by prep-TLC (DCM:MeOH=10:1). Compound 4 (8 mg, 12.91 umol, 41.52% yield, 96% purity) was obtained as white oil. LCMS: Rt=0.601 min, m/z=595.4 (M+H⁺)

To a solution of compound 4 (8 mg, 13.45 umol) in DCM (5 mL) was added TFA (749.27 mg, 6.57 mmol, 486.54 uL), the mixture was stirred at 25° C. for 1 hr. The mixture was concentrated to give a crude product. The residue was purified by preparative HPLC (column: Phenomenex luna C18 150*25 mm*10 um; mobile phase: [water (FA)-ACN]; B %: 32%-62%, 9 min) and lyophilized. Compound 077 (0.99 mg, 1.94 umol, 14.39% yield, 90.8% purity) was obtained as white solid. LCMS: Rt=0.489 min, m/z=465.4 (M+H⁺). ¹H NMR (400 MHz, CHLOROFORM-d) δ=12.69-12.13 (m, 1H), 8.26 (s, 1H), 8.20 (s, 1H), 7.35 (d, J=7.6 Hz, 2H), 7.32-7.27 (m, 2H), 7.04 (s, 3H), 6.41 (br d, J=6.7 Hz, 1H), 5.16 (s, 2H), 4.12-4.02 (m, 2H), 3.72 (d, J=7.1 Hz, 1H), 2.85 (s, 3H), 1.82 (d, J=7.1 Hz, 3H), 1.27-1.23 (m, 3H).

Scheme 12

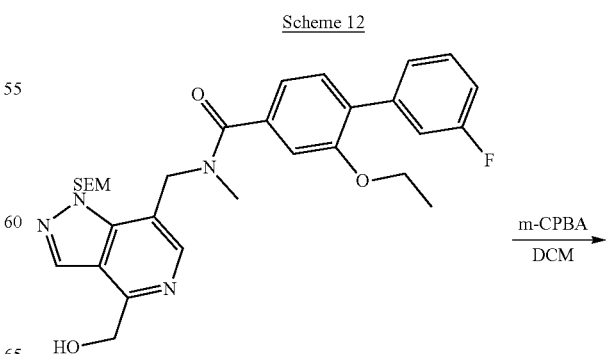

To a solution of compound 1 (300 mg, 716.91 umol) in THF (5 mL) in a 10 mL glass bottle was added SEM-Cl (143.43 mg, 860.29 umol, 152.26 uL) at 0° C., the mixture was stirred at 0° C. for 1 h. Then was added NaH (43.01 mg, 1.08 mmol, 60% purity) dropwise, the mixture was stirred at

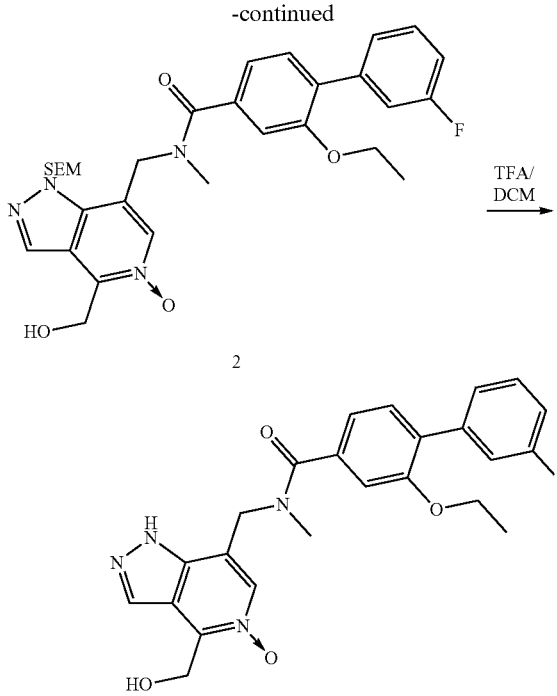

To a solution of Compound 1 (80 mg, 141.66 umol, 1 eq) in DCM (3 mL) was added m-CPBA (57.52 mg, 283.33 umol, 85% purity, 2 eq) at 0° C. The reaction mixture was stirred at 25° C. for 2 h. The mixture was poured into sat.Na$_2$SO$_3$.aq. (20 mL) and stirred for 0.25 h. Then extracted with EtOAc (20 mL×3). The combined organic layers were dried over Na$_2$SO$_4$, filtered and concentrated to give the crude product. The crude product was purified by Prep-TLC (PE:EA=0:1) to give the product (Rf=0.05). Compound 2 (50 mg, 78.01 umol, 55.06% yield, 90.6% purity) was obtained as light brown oil. LCMS: Rt=0.588 min, m/z=581.3 (M+H)$^+$.

To a solution of Compound 2 (40 mg, 68.88 umol, 1 eq) in DCM (2 mL) was added TFA (3.08 g, 27.01 mmol, 2 mL, 392.17 eq). The reaction mixture was stirred at 25° C. for 1 hr. The reaction mixture was concentrated directly to give crude product. The crude product was purified by prep-HPLC (column: YMC-Actus Triart C18 150*30 mm*7 um; mobile phase: [water (FA)-ACN]; B %: 30%-60%, 10 min). 078 (17.2 mg, 37.34 umol, 54.21% yield, 97.8% purity) was obtained as light-yellow solid. LCMS: Rt=0.484 min, m/z=451.1 (M+H)$^+$. 1H NMR (400 MHz, DMSO-d6) δppm 1.22-1.32 (m, 3 H) 3.07 (s, 3 H) 3.32 (br s, 2 H) 4.09-4.17 (m, 1 H) 4.91 (br s, 1 H) 4.95 (br d, J=5.38 Hz, 2 H) 5.93 (t, J=5.50 Hz, 1 H) 7.12-7.27 (m, 3 H) 7.31-7.50 (m, 4 H) 8.02 (br d, J=3.18 Hz, 1 H) 8.51 (br s, 1 H).

Example 2: THP-1 Cell-based NLRP3 Activation Assay

THP-1 cells are cultured in complete media (CM) until they reach logarithmic growth and achieve a viability>90%. CM is composed of RPMI-1640(+Glutamax)/10% fetal bovine serum/55 μM β-mercaptoethanol/pen/strep. Cells are spun down and resuspended to 1,000,000 cells/mL in CM containing either 20 nM or 500 nM PMA. 150,000 cells (150 μL) are then added to each well of a 96-well TC plate and incubated for either 24 hr or 3 hr, respectively, in a standard cell culture incubator (37° C.; 5% CO$_2$). After this incubation, the plate is tilted and media carefully removed. 200 μL of CM containing 100 ng/mL LPS is then added to the wells and the cells incubated an additional 3 hrs. The media is again removed and replaced with Opti-Mem medium containing pre-determined dilutions of test compounds in replicate wells. After a 30 min incubation, 10 μM nigericin (final concentration) in Opti-Mem medium with the corresponding concentration of compound is added to the wells for an additional 1 hr. Positive control wells contain 10 μM nigericin in Opti-Mem in the absence of test compound, while negative control wells contain Opti-Mem only. Supernatants are then transferred to a fresh 96-well plate for storage and assayed for IL-1β(human; DuoSet; R&D) and for TNFα(human; DuoSet; R&D) levels and relative pyroptosis using a CytoTox 96 Kit (do not freeze prior to testing; Promega). Once supernatants are removed, the relative viability of adherent cells in the 96-well TC plate are determined using a CellTiter-Glo® luminescent cell viability assay (Promega).

Table 4 below provides IC$_{50}$ data for the compounds disclosed herein where "+" is indicative of an IC$_{50}$ value of <50 uM, "++" is indicative of an IC$_{50}$ value of <10 uM, and "+++" is indicative of an IC$_{50}$ value of <1 uM.

TABLE 4

| No. | IC$_{50}$ |
|---|---|
| 001 | +++ |
| 002 | +++ |
| 003 | +++ |
| 004 | +++ |
| 005 | +++ |
| 006 | ++ |
| 007 | ++ |
| 008 | +++ |
| 009 | ++ |
| 010 | +++ |
| 011 | ++ |
| 012 | ++ |
| 013 | ++ |
| 014 | +++ |
| 015 | + |
| 016 | +++ |
| 017 | ++ |
| 018 | + |
| 019 | ++ |
| 020 | ++ |
| 021 | ++ |
| 022 | +++ |
| 023 | ++ |
| 024 | ++ |
| 025 | ++ |
| 026 | ++ |
| 027 | ++ |
| 028 | +++ |
| 029 | ++ |
| 030 | ++ |
| 031 | ++ |
| 032 | ++ |
| 033 | +++ |
| 034 | ++ |
| 035 | +++ |
| 036 | ++ |
| 037 | ++ |
| 038 | +++ |
| 040 | ++ |
| 042 | +++ |
| 043 | +++ |
| 045 | +++ |
| 046 | ++ |
| 047 | ++ |
| 048 | +++ |
| 049 | ++ |
| 050 | ++ |

TABLE 4-continued

| No. | IC$_{50}$ |
|---|---|
| 051 | ++ |
| 052 | +++ |
| 053 | ++ |
| 054 | +++ |
| 055 | +++ |
| 056 | +++ |
| 057 | + |
| 058 | ++ |
| 059 | +++ |
| 060 | ++ |
| 061 | ++ |
| 062 | +++ |
| 063 | +++ |
| 064 | +++ |
| 065 | +++ |
| 066 | ++ |
| 067 | +++ |
| 068 | ++ |
| 069 | +++ |
| 070 | +++ |
| 071 | + |
| 072 | ++ |
| 073 | + |
| 074 | +++ |
| 075 | +++ |
| 076 | ++ |
| 077 | +++ |
| 078 | +++ |

Example 3: Metabolic Stability of N-Oxides

The stability of the N-oxide compounds provided herein was studied compared to analogs not having N-oxide. These data show that the metabolic stability in the Human Liver Microsome Stability Assay (HLM) of the compounds provided herein is unexpectedly and dramatically extended compared to that comparator compounds shown in the table below. This enhanced metabolic stability corresponds to an extended half-life and duration of action when dosed in vivo. The results are shown in Table 5 below.

TABLE 5

| Structure | No. | HLM t$_{1/2}$ (min) |
|---|---|---|
| [structure] | 001 | >145 |
| [structure] | A | 3.7 |
| [structure] | B | 2 |
| [structure] | 004 | >145 |
| [structure] | C | 4 |
| [structure] | D | 1.5 |

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A method of treating inflammaging in a subject in need thereof comprising administering to the subject a therapeutically effective amount of a compound of Formula I:

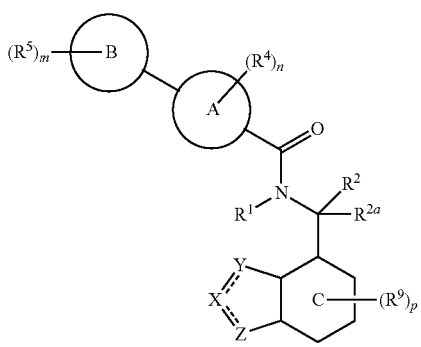

(I)

or a pharmaceutically acceptable salt thereof;
wherein the inflammaging is associated with cardiovascular disease, cancer arthritis, cataracts, osteoporosis, type 2 diabetes, hypertension, or Alzheimer's disease; and wherein ═ is an optional double bond;

X, Y, and Z are each independently selected from the group consisting of NH, NR$^3$, N, CH, and CR$^3$, provided at least one of X, Y, or Z are CH or CR$^3$;

Ring A is selected from the group consisting of $C_{6-10}$ aryl, 5-6 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

Ring C is pyridine N-oxide;

R$^1$ is selected from the group consisting of H, $C_{3-6}$ cycloalkyl, and $C_{1-6}$ alkyl;

R$^2$ and R$^{2a}$ are each independently selected from the group consisting of H, $C_{1-6}$ alkyl, $C_{1-6}$ alkoxy, and $C_{3-6}$ cycloalkyl;

alternatively, R$^2$ and R$^{2a}$, together with the atom to which they are attached form $C_{3-6}$ cycloalkyl or 3-6 membered heterocycloalkyl;

each R$^3$ is independently $C_{1-6}$ alkyl and $C_{3-6}$ cycloalkyl;

each R$^4$ is independently selected from the group consisting of $C_{1-6}$ alkyl, $C_{2-6}$ alkynyl, halo, OH, OR$^6$, NH$_2$, NH(C$_{1-6}$ alkyl), N(C$_{1-6}$ alkyl)$_2$, NHCOR$^6$, CN, $C_{1-6}$ haloalkyl, $C_{3-7}$ cycloalkyl, 3-7 membered heterocycloalkyl, and COR$^6$;

each R$^5$ is independently selected from the group consisting of $C_{1-6}$ alkyl, $C_{1-6}$ haloalkyl, $C_{1-6}$ alkyl-OH, $C_{2-6}$ alkynyl, halo, OH, OR$^7$, NH$_2$, NH(C$_{1-6}$ alkyl), N(C$_{1-6}$ alkyl)$_2$, NHCOR$^7$, CN, $C_{3-7}$ cycloalkyl, 3-7 membered heterocycloalkyl, COR$^7$, and SO$_2$R$^7$;

each R$^6$ is independently selected from the group consisting of $C_{1-6}$ alkyl, $C_{1-6}$ haloalkyl, $C_{0-6}$ alkyl-$C_{6-10}$ aryl, $C_{0-6}$ alkyl-5-10 membered heteroaryl, $C_{1-6}$ alkoxy, $C_{0-6}$ alkyl-$C_{3-6}$ cycloalkyl, $C_{0-6}$ alkyl-3-10 membered heterocycloalkyl, halo, NH$_2$, NH(C$_{1-6}$ alkyl), and N(C$_{1-6}$ alkyl)$_2$;

each R$^7$ is independently selected from the group consisting of $C_{1-6}$ alkyl, $C_{1-6}$ haloalkyl, $C_{0-6}$ alkyl-$C_{6-10}$ aryl, $C_{0-6}$ alkyl-5-10 membered heteroaryl, $C_{1-6}$ alkoxy, $C_{3-6}$ cycloalkyl, halo, NH$_2$, NH(C$_{1-6}$ alkyl), and N(C$_{1-6}$ alkyl)$_2$;

each R$^9$ is independently selected from the group consisting of $C_{1-6}$ alkyl, $C_{1-6}$ haloalkyl, $C_{1-6}$ alkoxy, $C_{1-6}$ alkyl-OH, $C_{3-6}$ cycloalkyl, halo, CN, OH, NH$_2$, NH(C$_{1-6}$ alkyl), and N(C$_{1-6}$ alkyl)$_2$;

m is 0, 1, 2, or 3;

n is 1, 2, or 3; and p is 0, 1, 2, or 3.

2. The method of claim 1, wherein the compound of Formula I is a compound of Formula Ia:

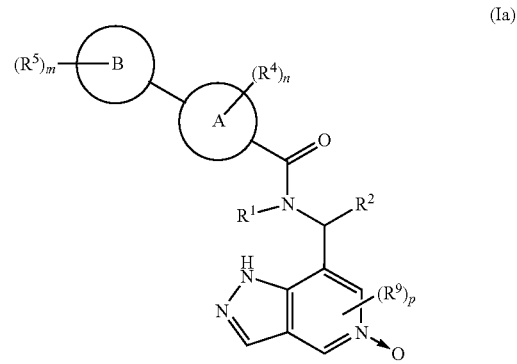

(Ia)

or a pharmaceutically acceptable salt thereof.

3. The method of claim 1, wherein the compound of Formula I is a compound of Formula Ib:

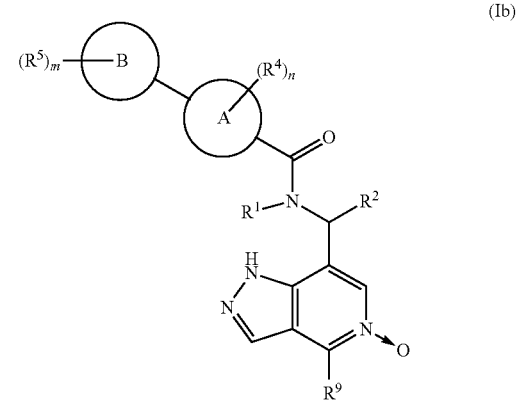

(Ib)

or a pharmaceutically acceptable salt thereof.

4. The method of claim 1, wherein the compound of Formula I is a compound of Formula Ic:

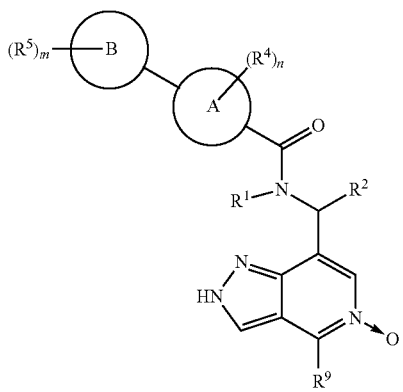

or a pharmaceutically acceptable salt thereof.

5. The method of claim 1, wherein Ring A is $C_{6-10}$ aryl.
6. The method of claim 1, wherein Ring A is phenyl.
7. The method of claim 1, wherein Ring B is phenyl or 5-6 membered heteroaryl.
8. The method of claim 1, wherein Ring B is phenyl.
9. The method of claim 1, wherein
$R^1$ is $C_{1-6}$ alkyl;
$R^2$ is selected from the group consisting of H, $C_{1-6}$ alkyl, $C_{1-6}$ alkoxy, and $C_{3-6}$ cycloalkyl;
$R^{2a}$ is H;
each $R^4$ is independently selected from the group consisting of $C_{1-6}$ alkyl, halo, and $OR^6$;
each $R^5$ is independently selected from the group consisting of $C_{1-6}$ haloalkyl, halo, CN, and $COR^7$;
each $R^6$ is independently selected from the group consisting of $C_{1-6}$ alkyl, $C_{1-6}$ haloalkyl, $C_{3-6}$ cycloalkyl, and 3-6 membered heterocycloalkyl;
each $R^7$ is independently selected from the group consisting of $C_{1-6}$ alkyl, $C_{1-6}$ haloalkyl, $C_{3-6}$ cycloalkyl, and $NH(C_{1-6}$ alkyl);
each $R^9$ is independently selected from the group consisting of $C_{1-6}$ alkyl, $C_{1-6}$ haloalkyl, $C_{1-6}$ alkoxy, $C_{1-6}$ alkyl-OH, $C_{3-6}$ cycloalkyl, and CN;
m is 0, 1, or 2; and
n is 1 or 2.

10. The method of claim 1, wherein
$R^1$ is $C_{1-6}$ alkyl;
$R^2$ is selected from the group consisting of H, $C_{1-6}$ alkyl, $C_{1-6}$ alkoxy, and $C_{3-6}$ cycloalkyl;
each $R^4$ is independently selected from the group consisting of $C_{1-6}$ alkyl, halo, and $OR^6$;
each $R^5$ is independently selected from the group consisting of $C_{1-6}$ haloalkyl, halo, CN, and $COR^7$;
each $R^6$ is independently selected from the group consisting of $C_{1-6}$ alkyl, $C_{1-6}$ haloalkyl, $C_{3-6}$ cycloalkyl, and 3-6 membered heterocycloalkyl;
each $R^7$ is independently selected from the group consisting of $C_{1-6}$ alkyl, $C_{1-6}$ haloalkyl, $C_{3-6}$ cycloalkyl, and $NH(C_{1-6}$ alkyl);
each $R^9$ is independently selected from the group consisting of $C_{1-6}$ alkyl, $C_{1-6}$ haloalkyl, $C_{1-6}$ alkoxy, $C_{1-6}$ alkyl-OH, $C_{3-6}$ cycloalkyl, and CN;
m is 0, 1, or 2; and
n is 1 or 2.

11. The method of claim 1, wherein $R^1$ is $C_{1-3}$ alkyl.
12. The method of claim 1, wherein $R^2$ is H.
13. The method of claim 1, wherein each $R^4$ is independently selected from the group consisting of $C_{1-6}$ alkyl, halo, and $OR^6$.
14. The method of claim 1, wherein each $R^4$ is independently selected from the group consisting of O(ethyl), O(cyclopropyl), O(oxetanyl), and $O(C_{1-3}$ haloalkyl).
15. The method of claim 1, wherein each $R^5$ is independently selected from the group consisting of $C_{1-6}$ haloalkyl, halo, CN, and $COR^7$.
16. The method of claim 1, wherein each $R^5$ is independently selected from the group consisting of $C_{1-6}$ haloalkyl, halo, CN, and $CONH(C_{1-6}$ alkyl).
17. The method of claim 1, wherein each $R^9$ is independently $C_{1-6}$ alkyl.
18. The method of claim 1, wherein m is 1 or 2.
19. The method of claim 1, wherein n is 1 or 2.
20. The method of claim 1, wherein p is 0 or 1.
21. The method of claim 2, wherein
Ring A is phenyl;
Ring B is phenyl or thienyl;
$R^1$ is $C_{1-3}$ alkyl;
$R^2$ is selected from the group consisting of H, $C_{1-6}$ alkyl, $C_{1-6}$ alkoxy, and $C_{3-6}$ cycloalkyl;
each $R^4$ is independently selected from the group consisting of $C_{1-6}$ alkyl, halo, and $OR^6$;
each $R^5$ is independently selected from the group consisting of $C_{1-6}$ haloalkyl, halo, CN, and $COR^7$;
each $R^6$ is independently selected from the group consisting of $C_{1-3}$ alkyl, $C_{1-3}$ haloalkyl, $C_{3-6}$ cycloalkyl, and 3-6 membered heterocycloalkyl;
each $R^7$ is independently selected from the group consisting of $C_{1-6}$ alkyl, $C_{1-6}$ haloalkyl, $C_{3-6}$ cycloalkyl, and $NH(C_{1-6}$ alkyl);
each $R^9$ is independently selected from the group consisting of $C_{1-3}$ alkyl, $C_{1-3}$ haloalkyl, $C_{1-3}$ alkoxy, $C_{1-6}$ alkyl-OH, $C_{3-6}$ cycloalkyl, and CN;
m is 1 or 2;
n is 1 or 2; and
p is 0 or 1.

22. The method of claim 1, wherein
X is N;
Y and Z are each independently selected from the group consisting of NH and CH.

23. The method of claim 1, wherein the compound of Formula I has one of the following core structures:

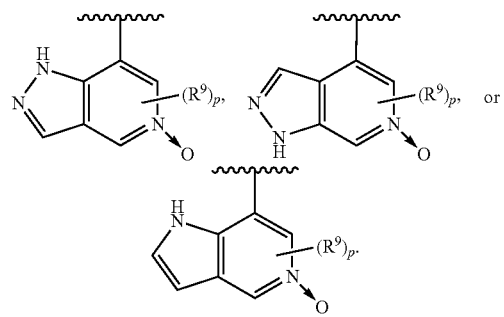

24. The method of claim 1, wherein the compound of Formula I has the following core structure:
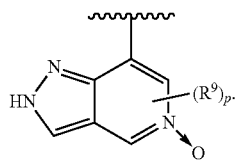
25. The method of claim 1, wherein the compound of Formula I is selected from the group consisting of
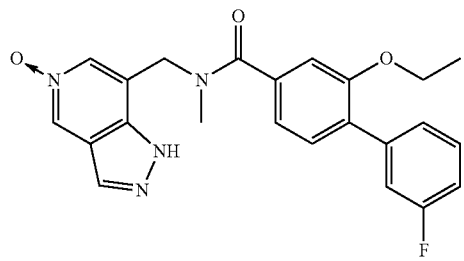 [SMILES: CCOc1cc(C(=O)N(C)Cc2c[n+]([O-])cc3cn[nH]c23)ccc1-c1cccc(F)c1]
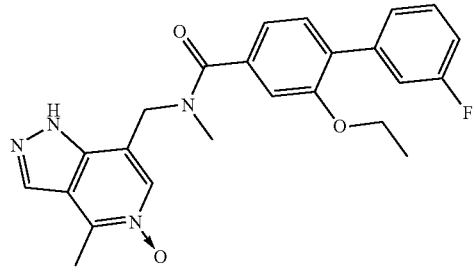
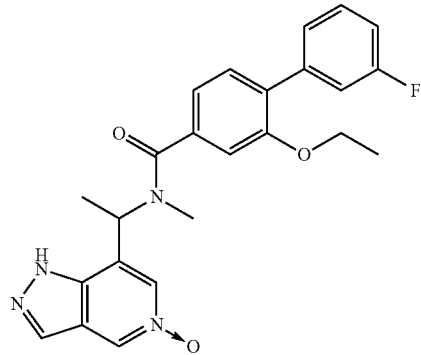
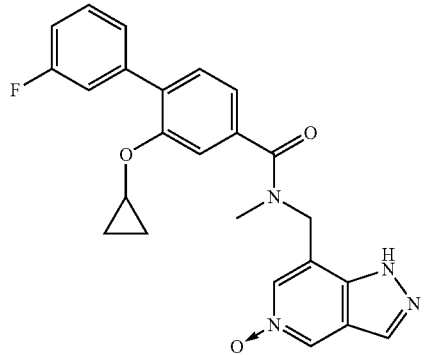 [SMILES: CN(Cc1c[n+]([O-])cc2cn[nH]c12)C(=O)c1ccc(-c2cccc(F)c2)c(OC2CC2)c1]
-continued
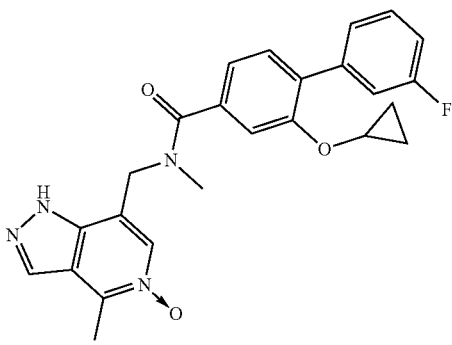
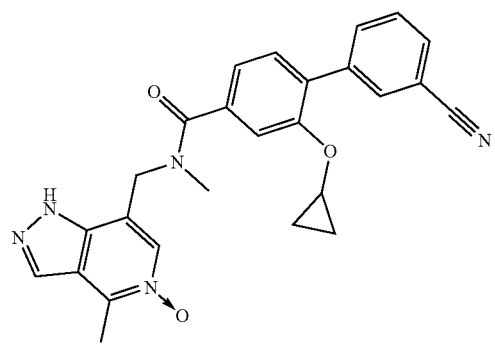
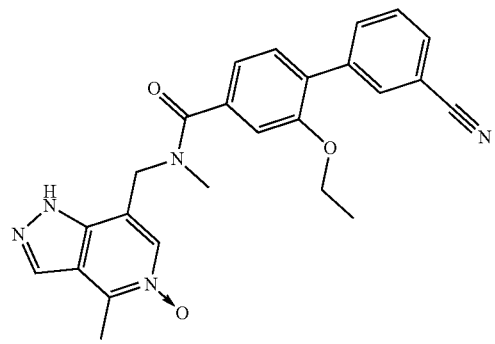
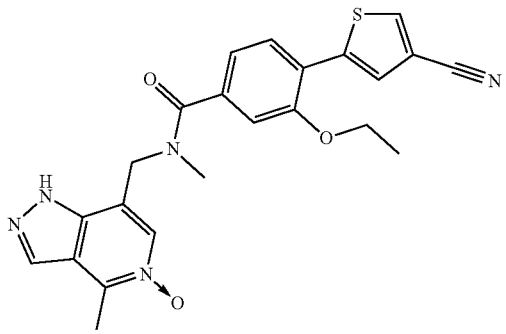
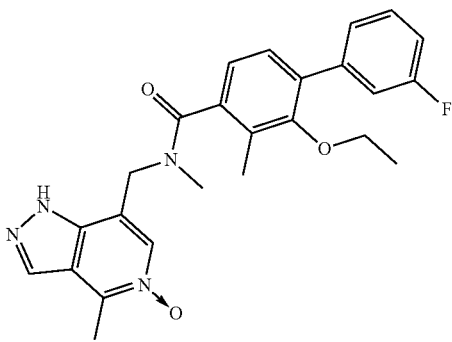

79
-continued
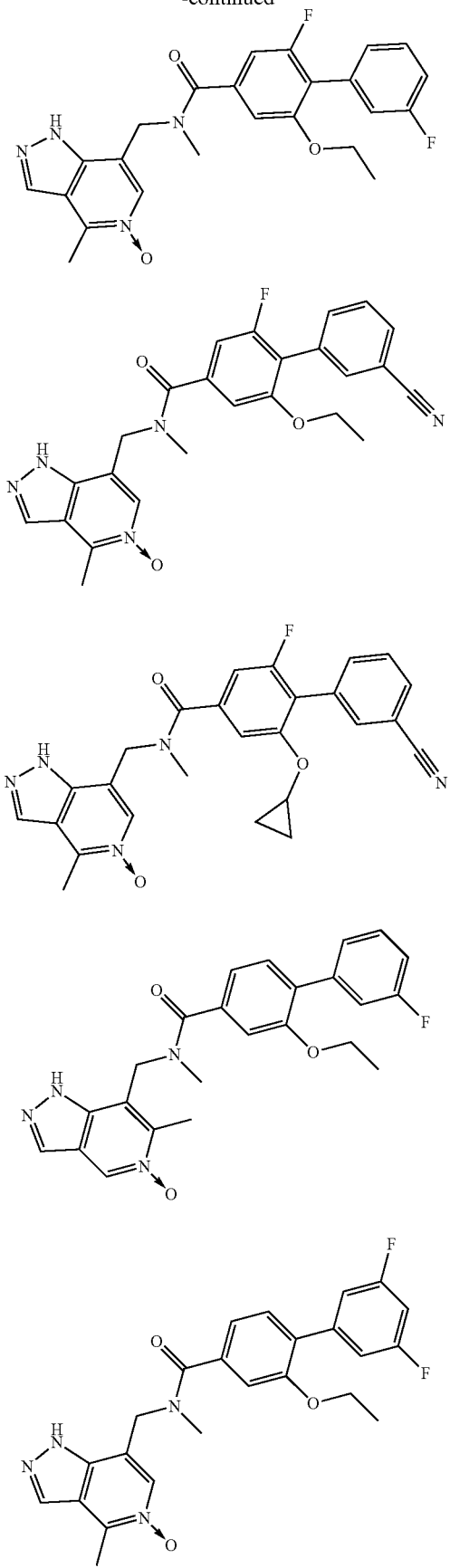
80
-continued
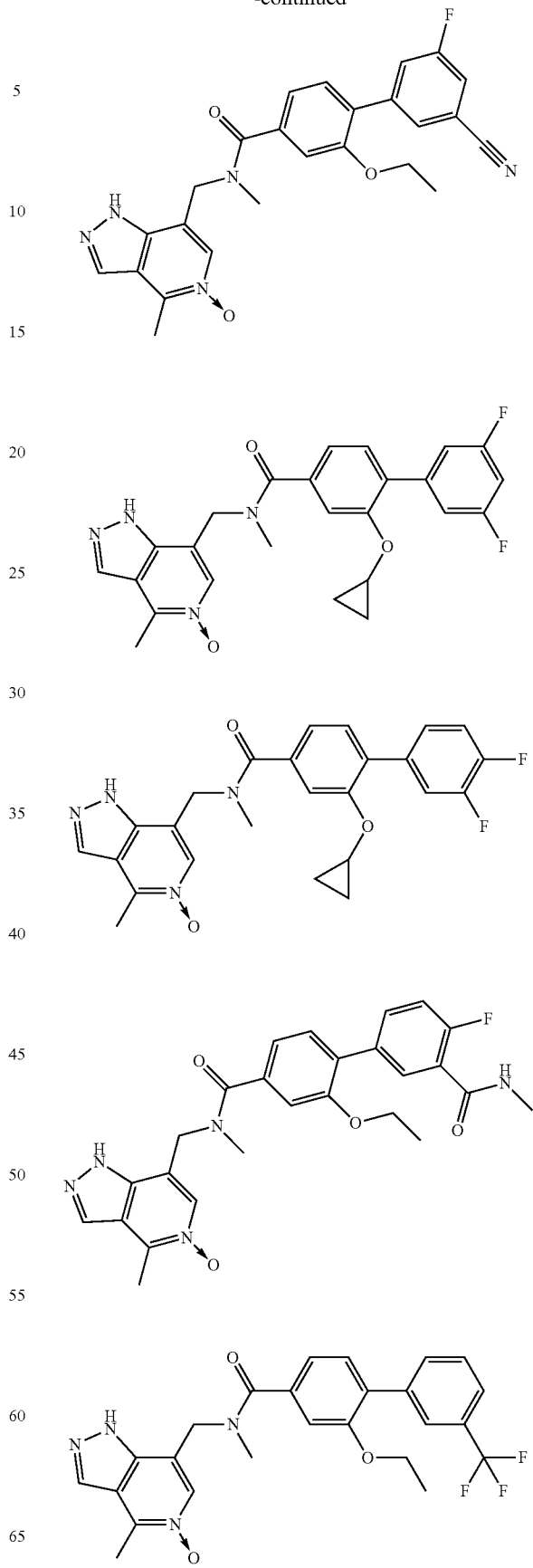

81
-continued
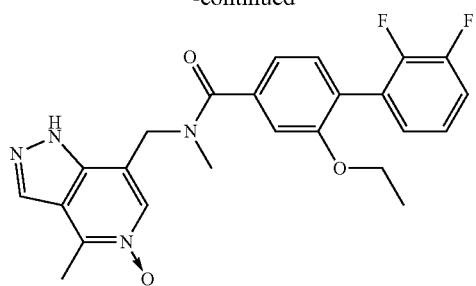
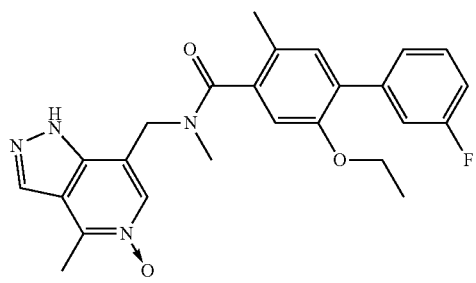
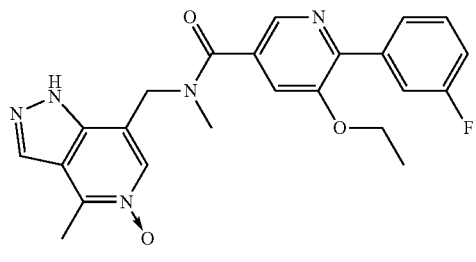
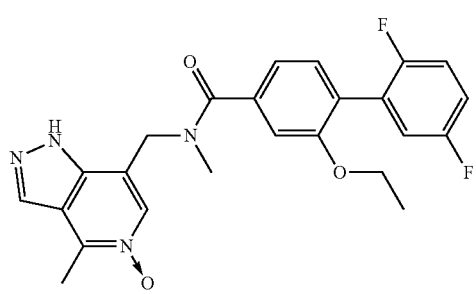
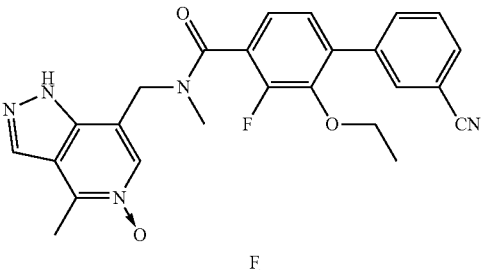
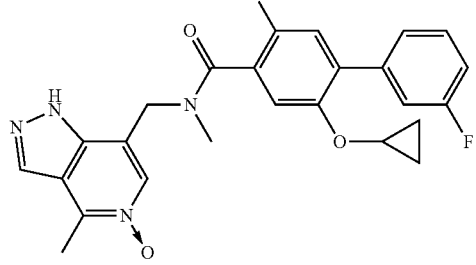
82
-continued
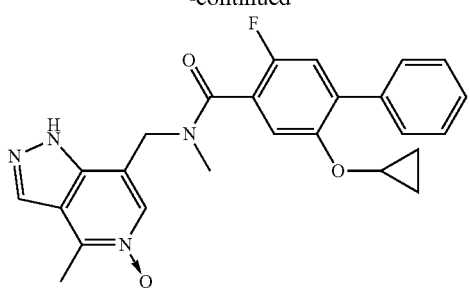
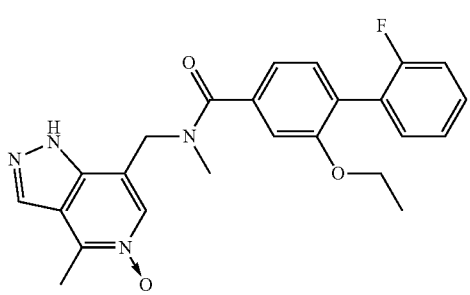
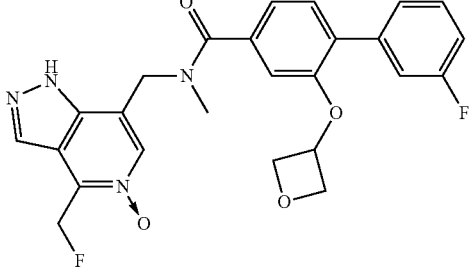
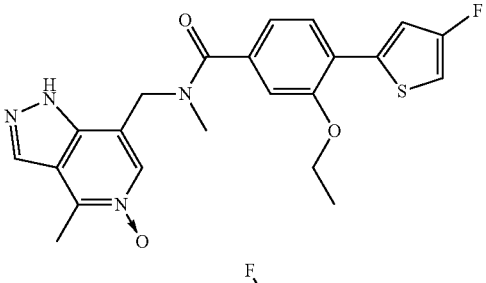
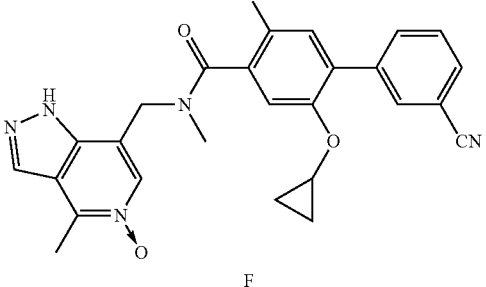
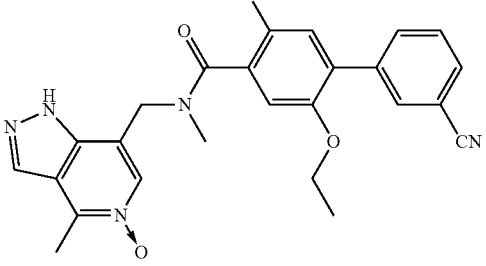

83
-continued
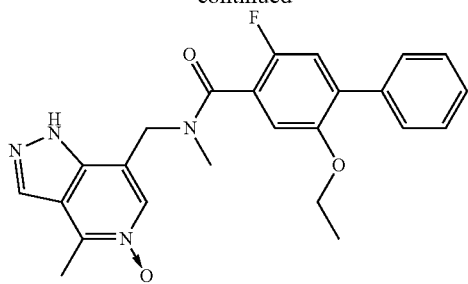
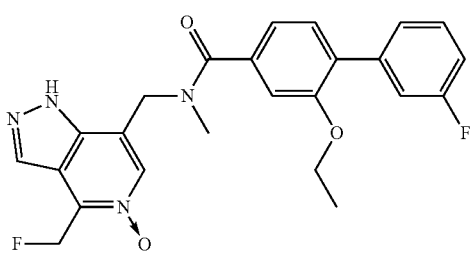
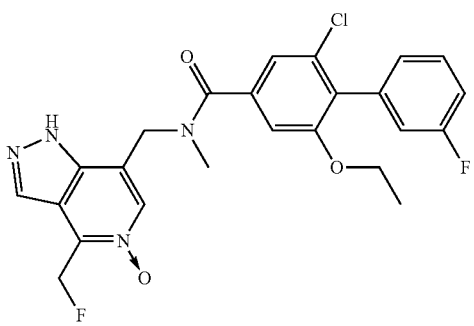
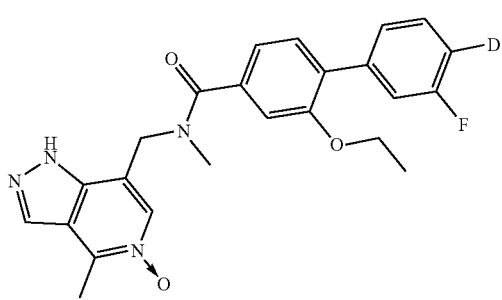
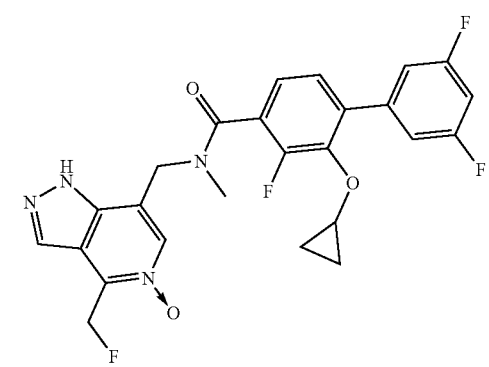
84
-continued
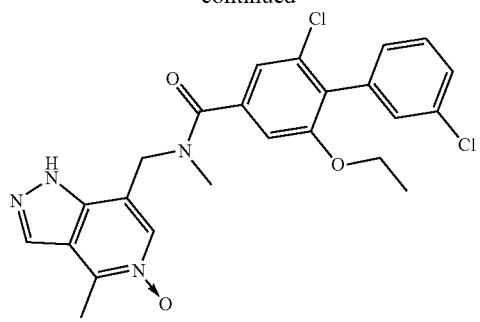
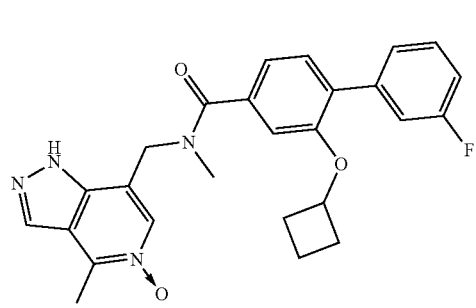
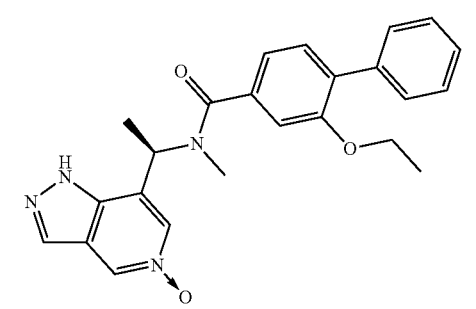
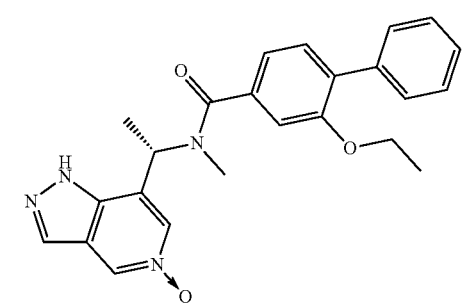
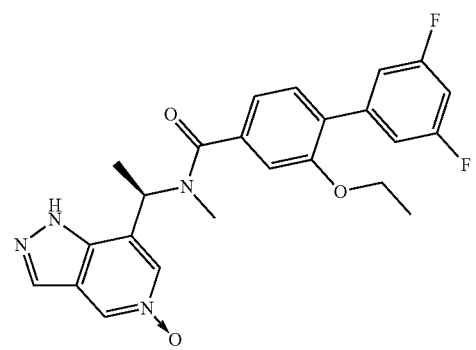

85
-continued
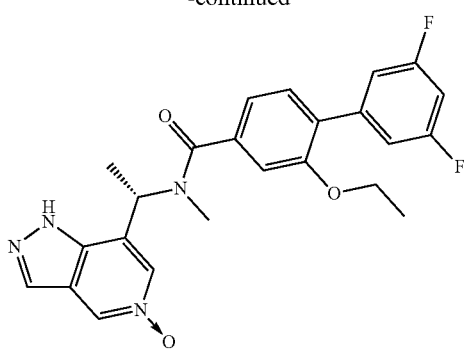
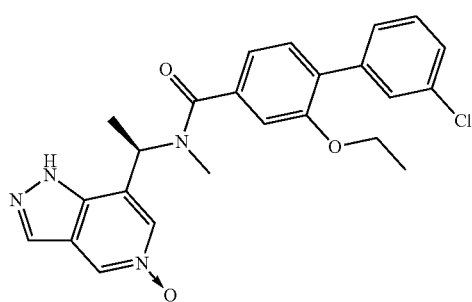
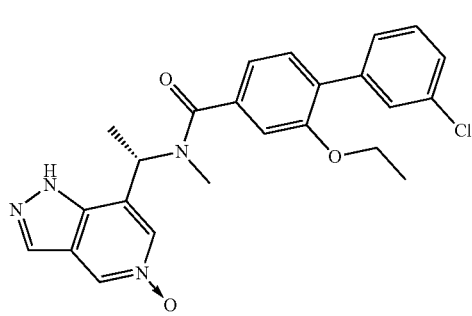
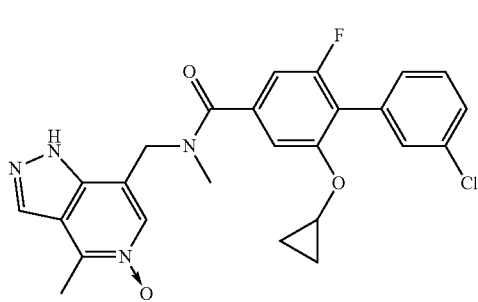
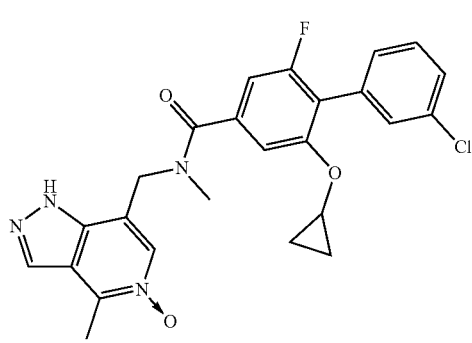
86
-continued
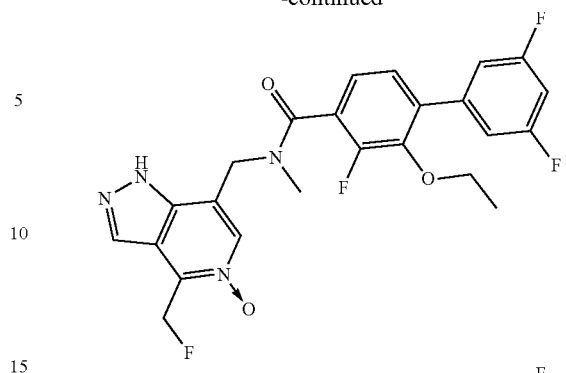
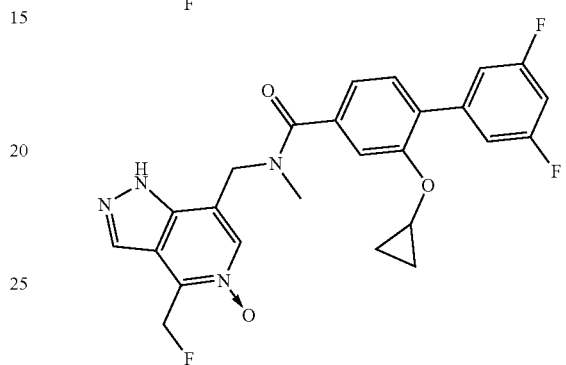
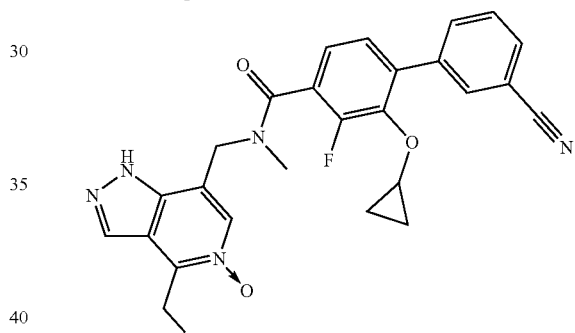
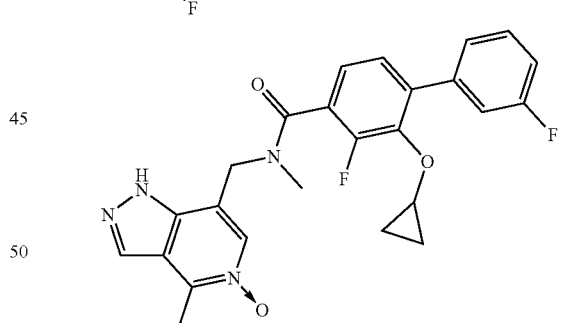
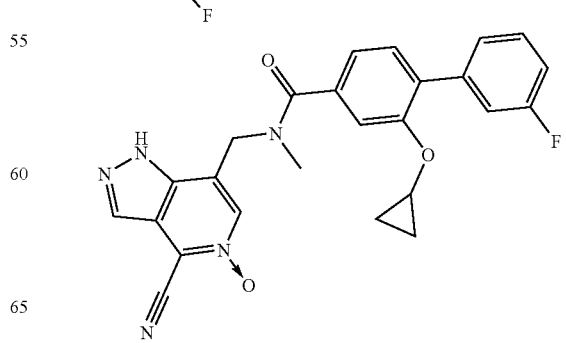

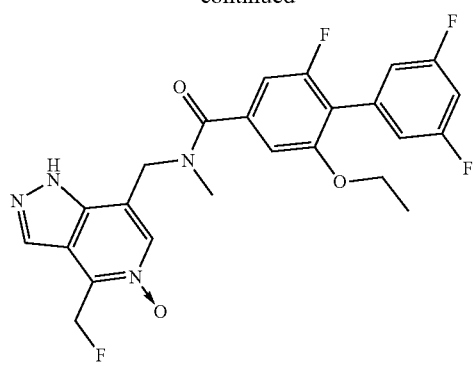
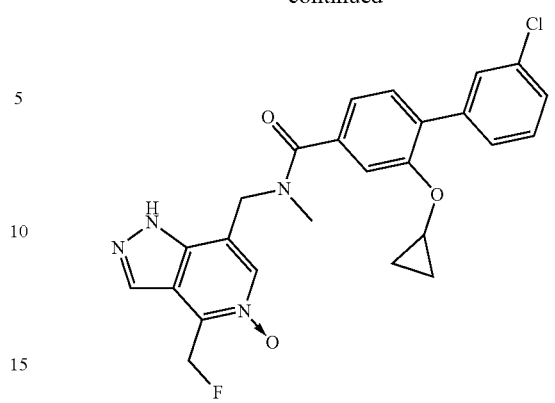
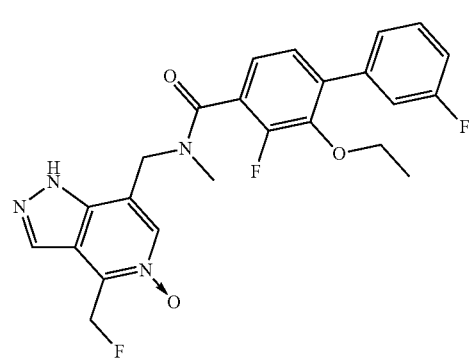
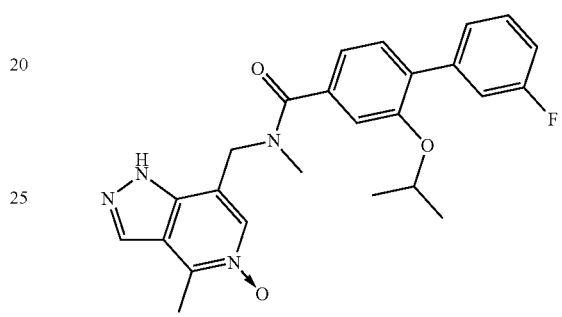
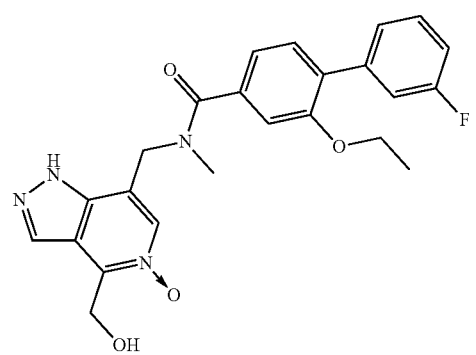
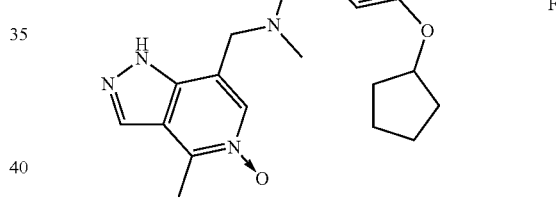
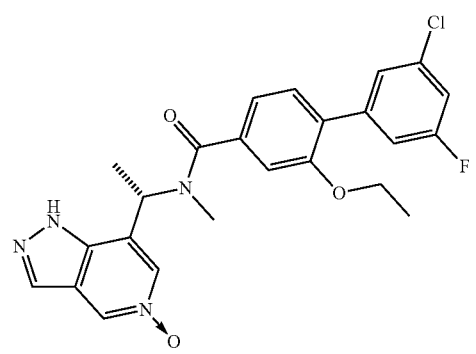
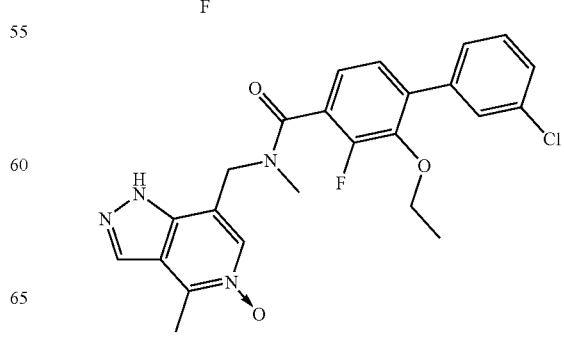

89
-continued
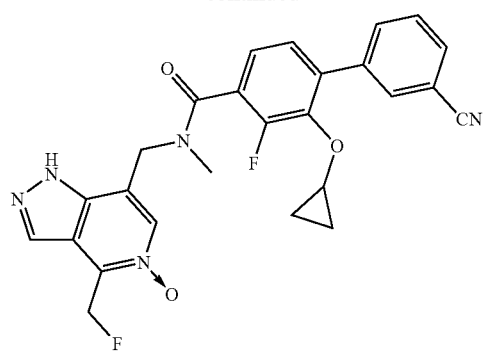
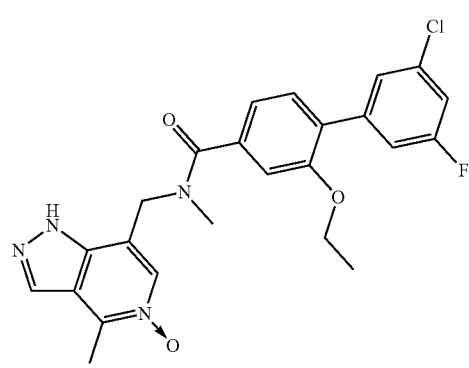
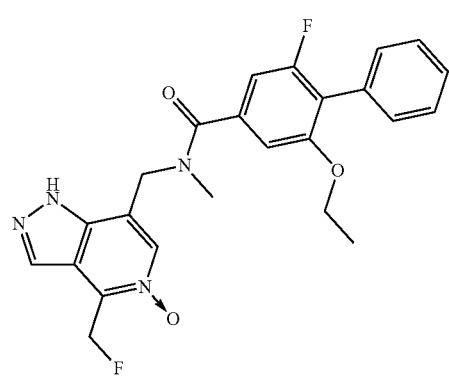
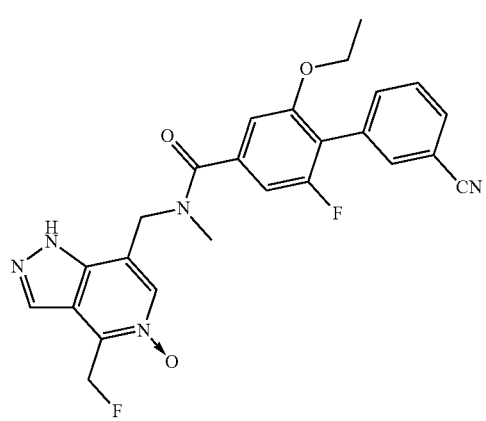
90
-continued
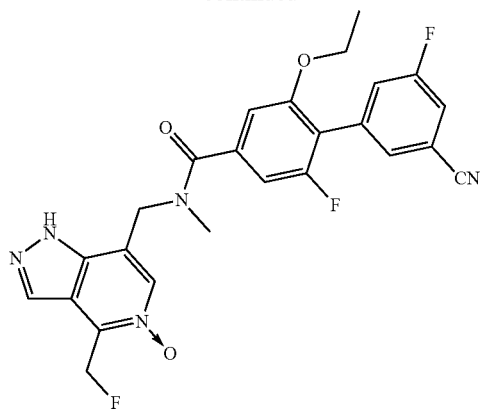
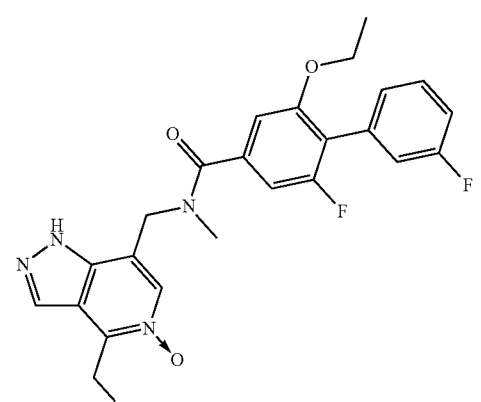
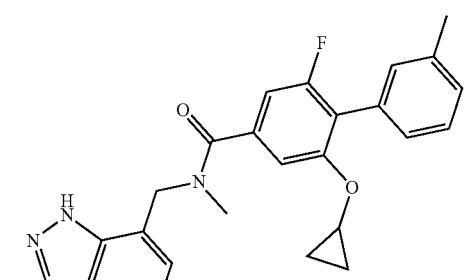
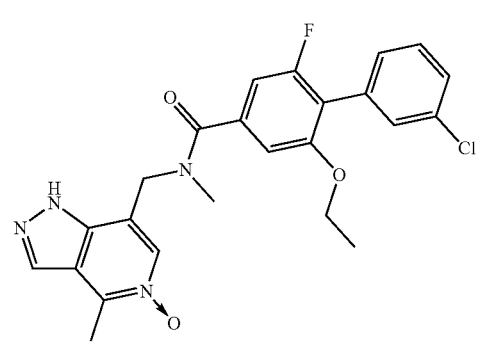

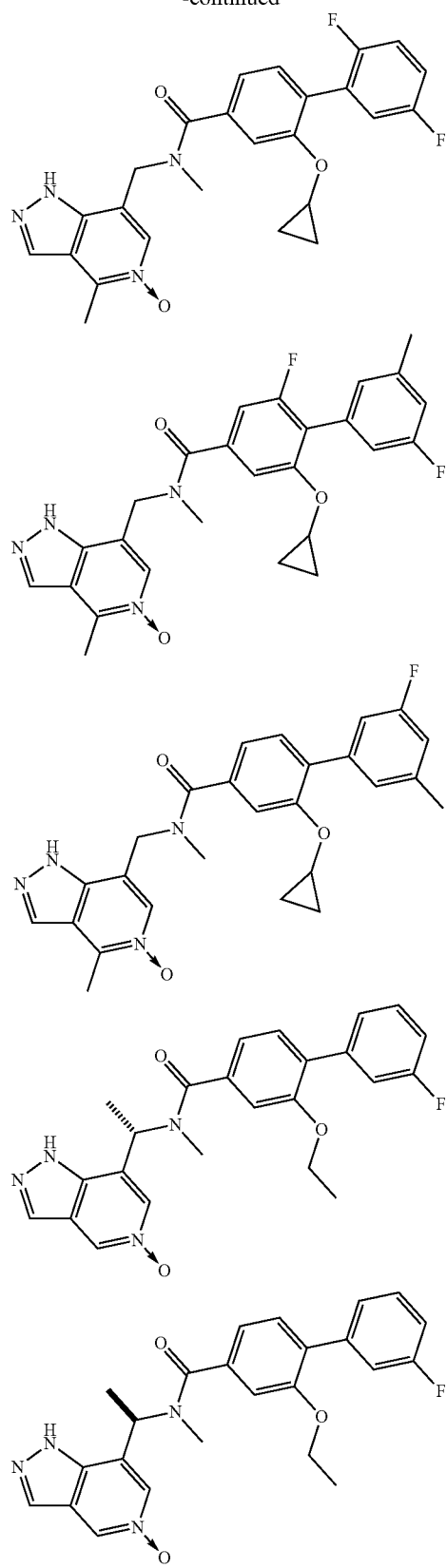
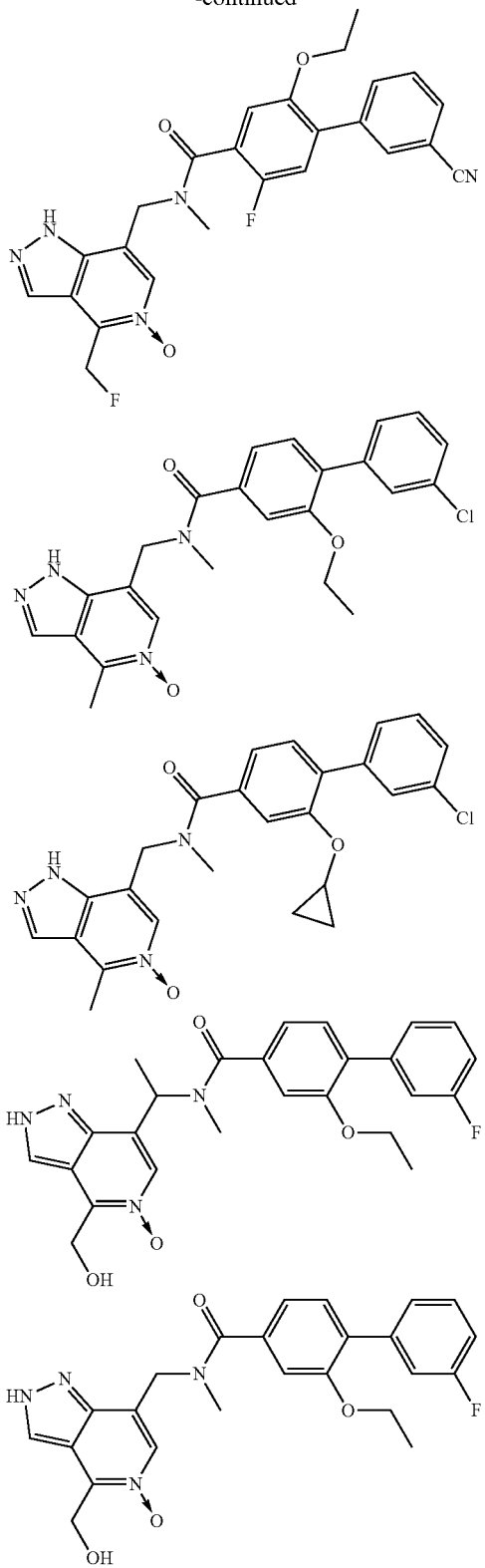
or a pharmaceutically acceptable salt thereof.
* * * * *